US012070276B2

(12) United States Patent
Calloway et al.

(10) Patent No.: US 12,070,276 B2
(45) Date of Patent: Aug. 27, 2024

(54) SURGICAL OBJECT TRACKING IN VISIBLE LIGHT VIA FIDUCIAL SEEDING AND SYNTHETIC IMAGE REGISTRATION

(71) Applicant: GLOBUS MEDICAL, INC., Audubon, PA (US)

(72) Inventors: Thomas Calloway, Pelham, NH (US); Norbert Johnson, North Andover, MA (US)

(73) Assignee: Globus Medical Inc., Exton, PA (US)

( * ) Notice: Subject to any disclaimer, the term of this patent is extended or adjusted under 35 U.S.C. 154(b) by 571 days.

(21) Appl. No.: 16/896,553

(22) Filed: Jun. 9, 2020

(65) Prior Publication Data

US 2021/0378756 A1 Dec. 9, 2021

(51) Int. Cl.

| | |
|---|---|
| ***A61B 34/20*** | (2016.01) |
| ***A61B 34/10*** | (2016.01) |
| ***A61B 34/30*** | (2016.01) |
| ***A61B 34/37*** | (2016.01) |
| ***A61B 90/00*** | (2016.01) |
| ***B25J 9/00*** | (2006.01) |
| ***G06T 7/38*** | (2017.01) |

(52) U.S. Cl.

CPC .............. *A61B 34/20* (2016.02); *A61B 34/10* (2016.02); *A61B 34/37* (2016.02); *A61B 90/361* (2016.02); *B25J 9/0021* (2013.01); *G06T 7/38* (2017.01); *A61B 2034/107* (2016.02); *A61B 2034/2057* (2016.02); *A61B 2034/301* (2016.02)

(58) Field of Classification Search

None

See application file for complete search history.

(56) References Cited

U.S. PATENT DOCUMENTS

| | | | |
|---|---|---|---|
| 4,150,293 | A | 4/1979 | Franke |
| 5,246,010 | A | 9/1993 | Gazzara et al. |
| 5,354,314 | A | 10/1994 | Hardy et al. |
| 5,397,323 | A | 3/1995 | Taylor et al. |
| 5,598,453 | A | 1/1997 | Baba et al. |
| 5,772,594 | A | 6/1998 | Barrick |
| 5,791,908 | A | 8/1998 | Gillio |
| 5,820,559 | A | 10/1998 | Ng et al. |
| 5,825,982 | A | 10/1998 | Wright et al. |
| 5,887,121 | A | 3/1999 | Funda et al. |
| 5,911,449 | A | 6/1999 | Daniele et al. |
| 5,951,475 | A | 9/1999 | Gueziec et al. |
| 5,987,960 | A | 11/1999 | Messner et al. |
| 6,006,126 | A | 12/1999 | Cosman |

(Continued)

OTHER PUBLICATIONS

US 8,231,638 B2, 07/2012, Swarup et al. (withdrawn)

(Continued)

*Primary Examiner* — Joel Lamprecht
*Assistant Examiner* — Ashish S Jasani

(57) ABSTRACT

A camera tracking system is disclosed for computer assisted navigation during surgery. The camera tracking system includes a camera bar, first and second tracking cameras, and a third tracking camera. The first and second tracking cameras are attached at spaced apart locations on the camera bar. The third tracking camera is attached at a location on the camera bar that is between locations of the first and second tracking cameras and spaced apart a distance from a line extending through centers of the first and second tracking cameras.

11 Claims, 24 Drawing Sheets

1900
1930
D2
D1
1910
1920
1940

(56) References Cited

U.S. PATENT DOCUMENTS 6,012,216 A 1/2000 Esteves et al.
6,031,888 A 2/2000 Ivan et al.
6,033,415 A 3/2000 Mittelstadt et al.
6,080,181 A 6/2000 Jensen et al.
6,106,511 A 8/2000 Jensen
6,122,541 A 9/2000 Cosman et al.
6,144,875 A 11/2000 Schweikard et al.
6,157,853 A 12/2000 Blume et al.
6,167,145 A 12/2000 Foley et al.
6,167,292 A 12/2000 Badano et al.
6,201,984 B1 3/2001 Funda et al.
6,203,196 B1 3/2001 Meyer et al.
6,205,411 B1 3/2001 DiGioia, III et al.
6,212,419 B1 4/2001 Blume et al.
6,231,565 B1 5/2001 Tovey et al.
6,236,875 B1 5/2001 Bucholz et al.
6,246,900 B1 6/2001 Cosman et al.
6,301,495 B1 10/2001 Gueziec et al.
6,306,126 B1 10/2001 Montezuma
6,312,435 B1 11/2001 Wallace et al.
6,314,311 B1 11/2001 Williams et al.
6,320,929 B1 11/2001 Von Der Haar
6,322,567 B1 11/2001 Mittelstadt et al.
6,325,808 B1 12/2001 Bernard et al.
6,340,363 B1 1/2002 Bolger et al.
6,377,011 B1 4/2002 Ben-Ur
6,379,302 B1 4/2002 Kessman et al.
6,402,762 B2 6/2002 Hunter et al.
6,424,885 B1 7/2002 Niemeyer et al.
6,447,503 B1 9/2002 Wynne et al.
6,451,027 B1 9/2002 Cooper et al.
6,477,400 B1 11/2002 Barrick
6,484,049 B1 11/2002 Seeley et al.
6,487,267 B1 11/2002 Wolter
6,490,467 B1 12/2002 Bucholz et al.
6,490,475 B1 12/2002 Seeley et al.
6,499,488 B1 12/2002 Hunter et al.
6,501,981 B1 12/2002 Schweikard et al.
6,507,751 B2 1/2003 Blume et al.
6,535,756 B1 3/2003 Simon et al.
6,560,354 B1 5/2003 Maurer, Jr. et al.
6,565,554 B1 5/2003 Niemeyer
6,587,750 B2 7/2003 Gerbi et al.
6,614,453 B1 9/2003 Suri et al.
6,614,871 B1 9/2003 Kobiki et al.
6,619,840 B2 9/2003 Rasche et al.
6,636,757 B1 10/2003 Jascob et al.
6,645,196 B1 11/2003 Nixon et al.
6,666,579 B2 12/2003 Jensen
6,669,635 B2 12/2003 Kessman et al.
6,701,173 B2 3/2004 Nowinski et al.
6,757,068 B2 6/2004 Foxlin
6,782,287 B2 8/2004 Grzeszczuk et al.
6,783,524 B2 8/2004 Anderson et al.
6,786,896 B1 9/2004 Madhani et al.
6,788,018 B1 9/2004 Blumenkranz
6,804,581 B2 10/2004 Wang et al.
6,823,207 B1 11/2004 Jensen et al.
6,827,351 B2 12/2004 Graziani et al.
6,837,892 B2 1/2005 Shoham
6,839,612 B2 1/2005 Sanchez et al.
6,856,826 B2 2/2005 Seeley et al.
6,856,827 B2 2/2005 Seeley et al.
6,879,880 B2 4/2005 Nowlin et al.
6,892,090 B2 5/2005 Verard et al.
6,920,347 B2 7/2005 Simon et al.
6,922,632 B2 7/2005 Foxlin
6,968,224 B2 11/2005 Kessman et al.
6,978,166 B2 12/2005 Foley et al.
6,988,009 B2 1/2006 Grimm et al.
6,991,627 B2 1/2006 Madhani et al.
6,996,487 B2 2/2006 Jutras et al.
6,999,852 B2 2/2006 Green
7,007,699 B2 3/2006 Martinelli et al.
7,016,457 B1 3/2006 Senzig et al.
7,043,961 B2 5/2006 Pandey et al.
7,062,006 B1 6/2006 Pelc et al.
7,063,705 B2 6/2006 Young et al.
7,072,707 B2 7/2006 Galloway, Jr. et al.
7,083,615 B2 8/2006 Peterson et al.
7,097,640 B2 8/2006 Wang et al.
7,099,428 B2 8/2006 Clinthorne et al.
7,108,421 B2 9/2006 Gregerson et al.
7,130,676 B2 10/2006 Barrick
7,139,418 B2 11/2006 Abovitz et al.
7,139,601 B2 11/2006 Bucholz et al.
7,155,316 B2 12/2006 Sutherland et al.
7,164,968 B2 1/2007 Treat et al.
7,167,738 B2 1/2007 Schweikard et al.
7,169,141 B2 1/2007 Brock et al.
7,172,627 B2 2/2007 Fiere et al.
7,194,120 B2 3/2007 Wicker et al.
7,197,107 B2 3/2007 Arai et al.
7,231,014 B2 6/2007 Levy
7,231,063 B2 6/2007 Naimark et al.
7,239,940 B2 7/2007 Wang et al.
7,248,914 B2 7/2007 Hastings et al.
7,301,648 B2 11/2007 Foxlin
7,302,288 B1 11/2007 Schellenberg
7,313,430 B2 12/2007 Urquhart et al.
7,318,805 B2 1/2008 Schweikard et al.
7,318,827 B2 1/2008 Leitner et al.
7,319,897 B2 1/2008 Leitner et al.
7,324,623 B2 1/2008 Heuscher et al.
7,327,865 B2 2/2008 Fu et al.
7,331,967 B2 2/2008 Lee et al.
7,333,642 B2 2/2008 Green
7,339,341 B2 3/2008 Oleynikov et al.
7,366,562 B2 4/2008 Dukesherer et al.
7,379,790 B2 5/2008 Toth et al.
7,386,365 B2 6/2008 Nixon
7,422,592 B2 9/2008 Morley et al.
7,435,216 B2 10/2008 Kwon et al.
7,440,793 B2 10/2008 Chauhan et al.
7,460,637 B2 12/2008 Clinthorne et al.
7,466,303 B2 12/2008 Yi et al.
7,493,153 B2 2/2009 Ahmed et al.
7,505,617 B2 3/2009 Fu et al.
7,533,892 B2 5/2009 Schena et al.
7,542,791 B2 6/2009 Mire et al.
7,555,331 B2 6/2009 Viswanathan
7,567,834 B2 7/2009 Clayton et al.
7,594,912 B2 9/2009 Cooper et al.
7,606,613 B2 10/2009 Simon et al.
7,607,440 B2 10/2009 Coste-Maniere et al.
7,623,902 B2 11/2009 Pacheco
7,630,752 B2 12/2009 Viswanathan
7,630,753 B2 12/2009 Simon et al.
7,643,862 B2 1/2010 Schoenefeld
7,660,623 B2 2/2010 Hunter et al.
7,661,881 B2 2/2010 Gregerson et al.
7,683,331 B2 3/2010 Chang
7,683,332 B2 3/2010 Chang
7,689,320 B2 3/2010 Prisco et al.
7,691,098 B2 4/2010 Wallace et al.
7,702,379 B2 4/2010 Avinash et al.
7,702,477 B2 4/2010 Tuemmler et al.
7,711,083 B2 5/2010 Heigl et al.
7,711,406 B2 5/2010 Kuhn et al.
7,720,523 B2 5/2010 Omernick et al.
7,725,253 B2 5/2010 Foxlin
7,726,171 B2 6/2010 Langlotz et al.
7,742,801 B2 6/2010 Neubauer et al.
7,751,865 B2 7/2010 Jascob et al.
7,760,849 B2 7/2010 Zhang
7,762,825 B2 7/2010 Burbank et al.
7,763,015 B2 7/2010 Cooper et al.
7,787,699 B2 8/2010 Mahesh et al.
7,796,728 B2 9/2010 Bergfjord
7,813,838 B2 10/2010 Sommer
7,818,044 B2 10/2010 Dukesherer et al.
7,819,859 B2 10/2010 Prisco et al.
7,824,401 B2 11/2010 Manzo et al.
7,831,294 B2 11/2010 Viswanathan

(56) References Cited

U.S. PATENT DOCUMENTS 7,834,484 B2 11/2010 Sartor
7,835,557 B2 11/2010 Kendrick et al.
7,835,778 B2 11/2010 Foley et al.
7,835,784 B2 11/2010 Mire et al.
7,840,253 B2 11/2010 Tremblay et al.
7,840,256 B2 11/2010 Lakin et al.
7,843,158 B2 11/2010 Prisco
7,844,320 B2 11/2010 Shahidi
7,853,305 B2 12/2010 Simon et al.
7,853,313 B2 12/2010 Thompson
7,865,269 B2 1/2011 Prisco et al.
D631,966 S 2/2011 Perloff et al.
7,879,045 B2 2/2011 Gielen et al.
7,881,767 B2 2/2011 Strommer et al.
7,881,770 B2 2/2011 Melkent et al.
7,886,743 B2 2/2011 Cooper et al.
RE42,194 E 3/2011 Foley et al.
RE42,226 E 3/2011 Foley et al.
7,900,524 B2 3/2011 Calloway et al.
7,907,166 B2 3/2011 Lamprecht et al.
7,909,122 B2 3/2011 Schena et al.
7,925,653 B2 4/2011 Saptharishi
7,930,065 B2 4/2011 Larkin et al.
7,935,130 B2 5/2011 Willliams
7,940,999 B2 5/2011 Liao et al.
7,945,012 B2 5/2011 Ye et al.
7,945,021 B2 5/2011 Shapiro et al.
7,953,470 B2 5/2011 Vetter et al.
7,954,397 B2 6/2011 Choi et al.
7,971,341 B2 7/2011 Dukesherer et al.
7,974,674 B2 7/2011 Hauck et al.
7,974,677 B2 7/2011 Mire et al.
7,974,681 B2 7/2011 Wallace et al.
7,979,157 B2 7/2011 Anvari
7,983,733 B2 7/2011 Viswanathan
7,988,215 B2 8/2011 Seibold
7,996,110 B2 8/2011 Lipow et al.
8,004,229 B2 8/2011 Nowlin et al.
8,010,177 B2 8/2011 Csavoy et al.
8,019,045 B2 9/2011 Kato
8,021,310 B2 9/2011 Sanborn et al.
8,035,685 B2 10/2011 Jensen
8,046,054 B2 10/2011 Kim et al.
8,046,057 B2 10/2011 Clarke
8,052,688 B2 11/2011 Wolf, II
8,054,184 B2 11/2011 Cline et al.
8,054,752 B2 11/2011 Druke et al.
8,057,397 B2 11/2011 Li et al.
8,057,407 B2 11/2011 Martinelli et al.
8,062,288 B2 11/2011 Cooper et al.
8,062,375 B2 11/2011 Glerum et al.
8,066,524 B2 11/2011 Burbank et al.
8,073,335 B2 12/2011 Labonville et al.
8,079,950 B2 12/2011 Stern et al.
8,086,299 B2 12/2011 Adler et al.
8,092,370 B2 1/2012 Roberts et al.
8,098,914 B2 1/2012 Liao et al.
8,100,950 B2 1/2012 St. Clair et al.
8,105,320 B2 1/2012 Manzo
8,108,025 B2 1/2012 Csavoy et al.
8,109,877 B2 2/2012 Moctezuma de la Barrera et al.
8,112,292 B2 2/2012 Simon
8,116,430 B1 2/2012 Shapiro et al.
8,120,301 B2 2/2012 Goldberg et al.
8,121,249 B2 2/2012 Wang et al.
8,123,675 B2 2/2012 Funda et al.
8,133,229 B1 3/2012 Bonutti
8,142,420 B2 3/2012 Schena
8,147,494 B2 4/2012 Leitner et al.
8,150,494 B2 4/2012 Simon et al.
8,150,497 B2 4/2012 Gielen et al.
8,150,498 B2 4/2012 Gielen et al.
8,165,658 B2 4/2012 Waynik et al.
8,170,313 B2 5/2012 Kendrick et al.
8,179,073 B2 5/2012 Farritor et al.
8,182,476 B2 5/2012 Julian et al.
8,184,880 B2 5/2012 Zhao et al.
8,202,278 B2 6/2012 Orban, III et al.
8,208,708 B2 6/2012 Homan et al.
8,208,988 B2 6/2012 Jensen
8,219,177 B2 7/2012 Smith et al.
8,219,178 B2 7/2012 Smith et al.
8,220,468 B2 7/2012 Cooper et al.
8,224,024 B2 7/2012 Foxlin et al.
8,224,484 B2 7/2012 Swarup et al.
8,225,798 B2 7/2012 Baldwin et al.
8,228,368 B2 7/2012 Zhao et al.
8,231,610 B2 7/2012 Jo et al.
8,263,933 B2 7/2012 Hartmann et al.
8,239,001 B2 8/2012 Verard et al.
8,241,271 B2 8/2012 Millman et al.
8,248,413 B2 8/2012 Gattani et al.
8,256,319 B2 9/2012 Cooper et al.
8,271,069 B2 9/2012 Jascob et al.
8,271,130 B2 9/2012 Hourtash
8,281,670 B2 10/2012 Larkin et al.
8,282,653 B2 10/2012 Nelson et al.
8,301,226 B2 10/2012 Csavoy et al.
8,311,611 B2 11/2012 Csavoy et al.
8,320,991 B2 11/2012 Jascob et al.
8,332,012 B2 12/2012 Kienzle, III
8,333,755 B2 12/2012 Cooper et al.
8,335,552 B2 12/2012 Stiles
8,335,557 B2 12/2012 Maschke
8,348,931 B2 1/2013 Cooper et al.
8,353,963 B2 1/2013 Glerum
8,358,818 B2 1/2013 Miga et al.
8,359,730 B2 1/2013 Burg et al.
8,374,673 B2 2/2013 Adcox et al.
8,374,723 B2 2/2013 Zhao et al.
8,379,791 B2 2/2013 Forthmann et al.
8,386,019 B2 2/2013 Camus et al.
8,392,022 B2 3/2013 Ortmaier et al.
8,394,099 B2 3/2013 Patwardhan
8,395,342 B2 3/2013 Prisco
8,398,634 B2 3/2013 Manzo et al.
8,400,094 B2 3/2013 Schena
8,414,957 B2 4/2013 Enzerink et al.
8,418,073 B2 4/2013 Mohr et al.
8,450,694 B2 5/2013 Baviera et al.
8,452,447 B2 5/2013 Nixon
RE44,305 E 6/2013 Foley et al.
8,462,911 B2 6/2013 Vesel et al.
8,465,476 B2 6/2013 Rogers et al.
8,465,771 B2 6/2013 Wan et al.
8,467,851 B2 6/2013 Mire et al.
8,467,852 B2 6/2013 Csavoy et al.
8,469,947 B2 6/2013 Devengenzo et al.
RE44,392 E 7/2013 Hynes
8,483,434 B2 7/2013 Buehner et al.
8,483,800 B2 7/2013 Jensen et al.
8,486,532 B2 7/2013 Enzerink et al.
8,489,235 B2 7/2013 Moll et al.
8,500,722 B2 8/2013 Cooper
8,500,728 B2 8/2013 Newton et al.
8,504,201 B2 8/2013 Moll et al.
8,506,555 B2 8/2013 Ruiz Morales
8,506,556 B2 8/2013 Schena
8,508,173 B2 8/2013 Goldberg et al.
8,512,318 B2 8/2013 Tovey et al.
8,515,576 B2 8/2013 Lipow et al.
8,518,120 B2 8/2013 Glerum et al.
8,521,331 B2 8/2013 Itkowitz
8,526,688 B2 9/2013 Groszmann et al.
8,526,700 B2 9/2013 Isaacs
8,527,094 B2 9/2013 Kumar et al.
8,528,440 B2 9/2013 Morley et al.
8,532,741 B2 9/2013 Heruth et al.
8,541,970 B2 9/2013 Nowlin et al.
8,548,563 B2 10/2013 Simon et al.
8,549,732 B2 10/2013 Burg et al.
8,551,114 B2 10/2013 Ramos de la Pena
8,551,116 B2 10/2013 Julian et al.
8,556,807 B2 10/2013 Scott et al.

(56) References Cited

U.S. PATENT DOCUMENTS 8,556,979 B2 10/2013 Glerum et al.
8,560,118 B2 10/2013 Green et al.
8,561,473 B2 10/2013 Blumenkranz
8,562,594 B2 10/2013 Cooper et al.
8,571,638 B2 10/2013 Shoham
8,571,710 B2 10/2013 Coste-Maniere et al.
8,573,465 B2 11/2013 Shelton, IV
8,574,303 B2 11/2013 Sharkey et al.
8,585,420 B2 11/2013 Burbank et al.
8,594,841 B2 11/2013 Zhao et al.
8,597,198 B2 12/2013 Sanborn et al.
8,600,478 B2 12/2013 Verard et al.
8,603,077 B2 12/2013 Cooper et al.
8,611,985 B2 12/2013 Lavallee et al.
8,613,230 B2 12/2013 Blumenkranz et al.
8,624,537 B2 1/2014 Nowlin et al.
8,630,389 B2 1/2014 Kato
8,634,897 B2 1/2014 Simon et al.
8,634,957 B2 1/2014 Toth et al.
8,638,056 B2 1/2014 Goldberg et al.
8,638,057 B2 1/2014 Goldberg et al.
8,639,000 B2 1/2014 Zhao et al.
8,641,726 B2 2/2014 Bonutti
8,644,907 B2 2/2014 Hartmann et al.
8,657,809 B2 2/2014 Schoepp
8,660,635 B2 2/2014 Simon et al.
8,666,544 B2 3/2014 Moll et al.
8,675,939 B2 3/2014 Moctezuma de la Barrera
8,678,647 B2 3/2014 Gregerson et al.
8,679,125 B2 3/2014 Smith et al.
8,679,183 B2 3/2014 Glerum et al.
8,682,413 B2 3/2014 Lloyd
8,684,253 B2 4/2014 Giordano et al.
8,685,098 B2 4/2014 Glerum et al.
8,693,730 B2 4/2014 Umasuthan et al.
8,694,075 B2 4/2014 Groszmann et al.
8,696,458 B2 4/2014 Foxlin et al.
8,700,123 B2 4/2014 Okamura et al.
8,706,086 B2 4/2014 Glerum
8,706,185 B2 4/2014 Foley et al.
8,706,301 B2 4/2014 Zhao et al.
8,717,430 B2 5/2014 Simon et al.
8,727,618 B2 5/2014 Maschke et al.
8,734,432 B2 5/2014 Tuma et al.
8,738,115 B2 5/2014 Amberg et al.
8,738,181 B2 5/2014 Greer et al.
8,740,882 B2 6/2014 Jun et al.
8,746,252 B2 6/2014 McGrogan et al.
8,749,189 B2 6/2014 Nowlin et al.
8,749,190 B2 6/2014 Nowlin et al.
8,761,930 B2 6/2014 Nixon
8,764,448 B2 7/2014 Yang et al.
8,771,170 B2 7/2014 Mesallum et al.
8,781,186 B2 7/2014 Clements et al.
8,781,630 B2 7/2014 Banks et al.
8,784,385 B2 7/2014 Boyden et al.
8,786,241 B2 7/2014 Nowlin et al.
8,787,520 B2 7/2014 Baba
8,792,704 B2 7/2014 Isaacs
8,798,231 B2 8/2014 Notohara et al.
8,800,838 B2 8/2014 Shelton, IV
8,808,164 B2 8/2014 Hoffman et al.
8,812,077 B2 8/2014 Dempsey
8,814,793 B2 8/2014 Brabrand
8,816,628 B2 8/2014 Nowlin et al.
8,818,105 B2 8/2014 Myronenko et al.
8,820,605 B2 9/2014 Shelton, IV
8,821,511 B2 9/2014 Von Jako et al.
8,823,308 B2 9/2014 Nowlin et al.
8,827,996 B2 9/2014 Scott et al.
8,828,024 B2 9/2014 Farritor et al.
8,830,224 B2 9/2014 Zhao et al.
8,834,489 B2 9/2014 Cooper et al.
8,834,490 B2 9/2014 Bonutti
8,838,270 B2 9/2014 Druke et al.
8,844,789 B2 9/2014 Shelton, IV et al.
8,855,822 B2 10/2014 Bartol et al.
8,858,598 B2 10/2014 Seifert et al.
8,860,753 B2 10/2014 Bhandarkar et al.
8,864,751 B2 10/2014 Prisco et al.
8,864,798 B2 10/2014 Weiman et al.
8,864,833 B2 10/2014 Glerum et al.
8,867,703 B2 10/2014 Shapiro et al.
8,870,880 B2 10/2014 Himmelberger et al.
8,876,866 B2 11/2014 Zappacosta et al.
8,880,223 B2 11/2014 Raj et al.
8,882,803 B2 11/2014 Iott et al.
8,888,821 B2 11/2014 Rezach et al.
8,888,853 B2 11/2014 Glerum et al.
8,888,854 B2 11/2014 Glerum et al.
8,894,652 B2 11/2014 Seifert et al.
8,894,688 B2 11/2014 Suh
8,894,691 B2 11/2014 Iott et al.
8,906,069 B2 12/2014 Hansell et al.
8,964,934 B2 2/2015 Ein-Gal
8,992,580 B2 3/2015 Bar et al.
8,996,169 B2 3/2015 Lightcap et al.
9,001,963 B2 4/2015 Sowards-Emmerd et al.
9,002,076 B2 4/2015 Khadem et al.
9,044,190 B2 6/2015 Rubner et al.
9,107,683 B2 8/2015 Hourtash et al.
9,125,556 B2 9/2015 Zehavi et al.
9,131,986 B2 9/2015 Greer et al.
9,215,968 B2 12/2015 Schostek et al.
9,308,050 B2 4/2016 Kostrzewski et al.
9,380,984 B2 7/2016 Li et al.
9,393,039 B2 7/2016 Lechner et al.
9,398,886 B2 7/2016 Gregerson et al.
9,398,890 B2 7/2016 Dong et al.
9,414,859 B2 8/2016 Ballard et al.
9,420,975 B2 8/2016 Gutfleisch et al.
9,492,235 B2 11/2016 Hourtash et al.
9,592,096 B2 3/2017 Maillet et al.
9,750,465 B2 9/2017 Engel et al.
9,757,203 B2 9/2017 Hourtash et al.
9,795,354 B2 10/2017 Menegaz et al.
9,814,535 B2 11/2017 Bar et al.
9,820,783 B2 11/2017 Donner et al.
9,833,265 B2 11/2017 Donner et al.
9,848,922 B2 12/2017 Tohmeh et al.
9,925,011 B2 3/2018 Gombert et al.
9,931,025 B1 4/2018 Graetzel et al.
10,034,717 B2 7/2018 Miller et al.
10,949,986 B1 * 3/2021 Colmenares .......... A61B 34/20
2001/0036302 A1 11/2001 Miller
2002/0035321 A1 3/2002 Bucholz et al.
2004/0068172 A1 4/2004 Nowinski et al.
2004/0076259 A1 4/2004 Jensen et al.
2005/0096502 A1 5/2005 Khalili
2005/0143651 A1 6/2005 Verard et al.
2005/0171558 A1 8/2005 Abovitz et al.
2006/0100610 A1 5/2006 Wallace et al.
2006/0173329 A1 8/2006 Marquart et al.
2006/0184396 A1 8/2006 Dennis et al.
2006/0241416 A1 10/2006 Marquart et al.
2006/0291612 A1 12/2006 Nishide et al.
2007/0015987 A1 1/2007 Benlloch Baviera et al.
2007/0021738 A1 1/2007 Hasser et al.
2007/0038059 A1 2/2007 Sheffer et al.
2007/0073133 A1 3/2007 Schoenefeld
2007/0156121 A1 7/2007 Millman et al.
2007/0156157 A1 7/2007 Nahum et al.
2007/0167712 A1 7/2007 Keglovich et al.
2007/0233238 A1 10/2007 Huynh et al.
2008/0004523 A1 1/2008 Jensen
2008/0013809 A1 1/2008 Zhu et al.
2008/0033283 A1 2/2008 Dellaca et al.
2008/0046122 A1 2/2008 Manzo et al.
2008/0082109 A1 4/2008 Moll et al.
2008/0108912 A1 5/2008 Node-Langlois
2008/0108991 A1 5/2008 Von Jako
2008/0109012 A1 5/2008 Falco et al.
2008/0144906 A1 6/2008 Allred et al.
2008/0161680 A1 7/2008 Von Jako et al.

(56) References Cited

U.S. PATENT DOCUMENTS

2008/0161682 A1 7/2008 Kendrick et al.
2008/0177203 A1 7/2008 von Jako
2008/0214922 A1 9/2008 Hartmann et al.
2008/0228068 A1 9/2008 Viswanathan et al.
2008/0228196 A1 9/2008 Wang et al.
2008/0235052 A1 9/2008 Node-Langlois et al.
2008/0269596 A1 10/2008 Revie et al.
2008/0287771 A1 11/2008 Anderson
2008/0287781 A1 11/2008 Revie et al.
2008/0300477 A1 12/2008 Lloyd et al.
2008/0300478 A1 12/2008 Zuhars et al.
2008/0302950 A1 12/2008 Park et al.
2008/0306490 A1 12/2008 Lakin et al.
2008/0319311 A1 12/2008 Hamadeh
2009/0012509 A1 1/2009 Csavoy et al.
2009/0030428 A1 1/2009 Omori et al.
2009/0080737 A1 3/2009 Battle et al.
2009/0185655 A1 7/2009 Koken et al.
2009/0198121 A1 8/2009 Hoheisel
2009/0216113 A1 8/2009 Meier et al.
2009/0228019 A1 9/2009 Gross et al.
2009/0259123 A1 10/2009 Navab et al.
2009/0259230 A1 10/2009 Khadem et al.
2009/0264899 A1 10/2009 Appenrodt et al.
2009/0281417 A1 11/2009 Hartmann et al.
2010/0022874 A1 1/2010 Wang et al.
2010/0039506 A1 2/2010 Sarvestani et al.
2010/0125286 A1 5/2010 Wang et al.
2010/0130986 A1 5/2010 Mailloux et al.
2010/0228117 A1 9/2010 Hartmann
2010/0228265 A1 9/2010 Prisco
2010/0249571 A1 9/2010 Jensen et al.
2010/0274120 A1 10/2010 Heuscher
2010/0280363 A1 11/2010 Skarda et al.
2010/0331858 A1 12/2010 Simaan et al.
2011/0022229 A1 1/2011 Jang et al.
2011/0077504 A1 3/2011 Fischer et al.
2011/0098553 A1 4/2011 Robbins et al.
2011/0137152 A1 6/2011 Li
2011/0213384 A1 9/2011 Jeong
2011/0224684 A1 9/2011 Larkin et al.
2011/0224685 A1 9/2011 Larkin et al.
2011/0224686 A1 9/2011 Larkin et al.
2011/0224687 A1 9/2011 Larkin et al.
2011/0224688 A1 9/2011 Larkin et al.
2011/0224689 A1 9/2011 Larkin et al.
2011/0224825 A1 9/2011 Larkin et al.
2011/0230967 A1 9/2011 O'Halloran et al.
2011/0238080 A1 9/2011 Ranjit et al.
2011/0276058 A1 11/2011 Choi et al.
2011/0282189 A1 11/2011 Graumann
2011/0286573 A1 11/2011 Schretter et al.
2011/0295062 A1 12/2011 Gratacos Solsona et al.
2011/0295370 A1 12/2011 Suh et al.
2011/0306986 A1 12/2011 Lee et al.
2012/0035507 A1 2/2012 George et al.
2012/0046668 A1 2/2012 Gantes
2012/0051498 A1 3/2012 Koishi
2012/0053597 A1 3/2012 Anvari et al.
2012/0059248 A1 3/2012 Holsing et al.
2012/0071753 A1 3/2012 Hunter et al.
2012/0108954 A1 5/2012 Schulhauser et al.
2012/0136372 A1 5/2012 Amat Girbau et al.
2012/0143084 A1 6/2012 Shoham
2012/0184839 A1 7/2012 Woerlein
2012/0197182 A1 8/2012 Millman et al.
2012/0226145 A1 9/2012 Chang et al.
2012/0235909 A1 9/2012 Birkenbach et al.
2012/0245596 A1 9/2012 Meenink
2012/0253332 A1 10/2012 Moll
2012/0253360 A1 10/2012 White et al.
2012/0256092 A1 10/2012 Zingerman
2012/0294498 A1 11/2012 Popovic
2012/0296203 A1 11/2012 Hartmann et al.
2013/0006267 A1 1/2013 Odermatt et al.
2013/0016889 A1 1/2013 Myronenko et al.
2013/0030571 A1 1/2013 Ruiz Morales et al.
2013/0035583 A1 2/2013 Park et al.
2013/0060146 A1 3/2013 Yang et al.
2013/0060337 A1 3/2013 Petersheim et al.
2013/0094742 A1 4/2013 Feilkas
2013/0096574 A1 4/2013 Kang et al.
2013/0113791 A1 5/2013 Isaacs et al.
2013/0116706 A1 5/2013 Lee et al.
2013/0131695 A1 5/2013 Scarfogliero et al.
2013/0144307 A1 6/2013 Jeong et al.
2013/0158542 A1 6/2013 Manzo et al.
2013/0165937 A1 6/2013 Patwardhan
2013/0178867 A1 7/2013 Farritor et al.
2013/0178868 A1 7/2013 Roh
2013/0178870 A1 7/2013 Schena
2013/0204271 A1 8/2013 Brisson et al.
2013/0211419 A1 8/2013 Jensen
2013/0211420 A1 8/2013 Jensen
2013/0218142 A1 8/2013 Tuma et al.
2013/0223702 A1 8/2013 Holsing et al.
2013/0225942 A1 8/2013 Holsing et al.
2013/0225943 A1 8/2013 Holsing et al.
2013/0231556 A1 9/2013 Holsing et al.
2013/0237995 A1 9/2013 Lee et al.
2013/0245375 A1 9/2013 DiMaio et al.
2013/0261640 A1 10/2013 Kim et al.
2013/0272488 A1 10/2013 Bailey et al.
2013/0272489 A1 10/2013 Dickman et al.
2013/0274761 A1 10/2013 Devengenzo et al.
2013/0281821 A1 10/2013 Liu et al.
2013/0296884 A1 11/2013 Taylor et al.
2013/0303887 A1 11/2013 Holsing et al.
2013/0307955 A1 11/2013 Deitz et al.
2013/0317521 A1 11/2013 Choi et al.
2013/0325033 A1 12/2013 Schena et al.
2013/0325035 A1 12/2013 Hauck et al.
2013/0331686 A1 12/2013 Freysinger et al.
2013/0331858 A1 12/2013 Devengenzo et al.
2013/0331861 A1 12/2013 Yoon
2013/0342578 A1 12/2013 Isaacs
2013/0345717 A1 12/2013 Markvicka et al.
2013/0345757 A1 12/2013 Stad
2014/0001235 A1 1/2014 Shelton, IV
2014/0012131 A1 1/2014 Heruth et al.
2014/0031664 A1 1/2014 Kang et al.
2014/0046128 A1 2/2014 Lee et al.
2014/0046132 A1 2/2014 Hoeg et al.
2014/0046340 A1 2/2014 Wilson et al.
2014/0049629 A1 2/2014 Siewerdsen et al.
2014/0058406 A1 2/2014 Tsekos
2014/0073914 A1 3/2014 Lavallee et al.
2014/0080086 A1 3/2014 Chen
2014/0081128 A1 3/2014 Verard et al.
2014/0088612 A1 3/2014 Bartol et al.
2014/0094694 A1 4/2014 Moctezuma de la Barrera
2014/0094851 A1 4/2014 Gordon
2014/0096369 A1 4/2014 Matsumoto et al.
2014/0100587 A1 4/2014 Farritor et al.
2014/0121676 A1 5/2014 Kostrzewski et al.
2014/0128882 A1 5/2014 Kwak et al.
2014/0135796 A1 5/2014 Simon et al.
2014/0142591 A1 5/2014 Alvarez et al.
2014/0142592 A1 5/2014 Moon et al.
2014/0148692 A1 5/2014 Hartmann et al.
2014/0163581 A1 6/2014 Devengenzo et al.
2014/0171781 A1 6/2014 Stiles
2014/0171900 A1 6/2014 Stiles
2014/0171965 A1 6/2014 Loh et al.
2014/0180308 A1 6/2014 von Grunberg
2014/0180309 A1 6/2014 Seeber et al.
2014/0187915 A1 7/2014 Yaroshenko et al.
2014/0188132 A1 7/2014 Kang
2014/0194699 A1 7/2014 Roh et al.
2014/0130810 A1 8/2014 Azizian et al.
2014/0221819 A1 8/2014 Sarment
2014/0222023 A1 8/2014 Kim et al.
2014/0228631 A1 8/2014 Kwak et al.
2014/0234804 A1 8/2014 Huang et al.

(56) References Cited

U.S. PATENT DOCUMENTS

2014/0257328 A1 9/2014 Kim et al.
2014/0257329 A1 9/2014 Jang et al.
2014/0257330 A1 9/2014 Choi et al.
2014/0275760 A1 9/2014 Lee et al.
2014/0275985 A1 9/2014 Walker et al.
2014/0276931 A1 9/2014 Parihar et al.
2014/0276940 A1 9/2014 Seo
2014/0276944 A1 9/2014 Farritor et al.
2014/0288413 A1 9/2014 Hwang et al.
2014/0299648 A1 10/2014 Shelton, IV et al.
2014/0303434 A1 10/2014 Farritor et al.
2014/0303643 A1 10/2014 Ha et al.
2014/0305995 A1 10/2014 Shelton, IV et al.
2014/0309659 A1 10/2014 Roh et al.
2014/0316436 A1 10/2014 Bar et al.
2014/0323803 A1 10/2014 Hoffman et al.
2014/0324070 A1 10/2014 Min et al.
2014/0330288 A1 11/2014 Date et al.
2014/0364720 A1 12/2014 Darrow et al.
2014/0371577 A1 12/2014 Maillet et al.
2015/0039034 A1 2/2015 Frankel et al.
2015/0085970 A1 3/2015 Bouhnik et al.
2015/0146847 A1 5/2015 Liu
2015/0150524 A1 6/2015 Yorkston et al.
2015/0196261 A1 7/2015 Funk
2015/0213633 A1 7/2015 Chang et al.
2015/0335480 A1 11/2015 Alvarez et al.
2015/0342647 A1 12/2015 Frankel et al.
2016/0005194 A1 1/2016 Schretter et al.
2016/0166329 A1 6/2016 Langan et al.
2016/0235480 A1 8/2016 Scholl et al.
2016/0249990 A1 9/2016 Glozman et al.
2016/0302871 A1 10/2016 Gregerson et al.
2016/0320322 A1 11/2016 Suzuki
2016/0331335 A1 11/2016 Gregerson et al.
2017/0135770 A1 5/2017 Scholl et al.
2017/0143284 A1 5/2017 Sehnert et al.
2017/0143426 A1 5/2017 Isaacs et al.
2017/0156816 A1 6/2017 Ibrahim
2017/0202629 A1 7/2017 Maillet et al.
2017/0215825 A1 8/2017 Johnson et al.
2017/0215826 A1 8/2017 Johnson et al.
2017/0215827 A1 8/2017 Johnson et al.
2017/0231710 A1 8/2017 Scholl et al.
2017/0258426 A1 9/2017 Risher-Kelly et al.
2017/0258526 A1* 9/2017 Lang ...................... A61B 34/74
2017/0273748 A1 9/2017 Hourtash et al.
2017/0296277 A1 10/2017 Hourtash et al.
2017/0360493 A1 12/2017 Zucher et al.
2018/0064496 A1* 3/2018 Hladio ................. A61B 5/6847
2018/0325610 A1* 11/2018 Cameron ............. A61B 5/1072
2019/0105514 A1 4/2019 Amstutz et al.

OTHER PUBLICATIONS

Ouellete et al. ("A Simple Operator for Very Precise Estimation of Ellipses," (May 28, 2007), Fourth Canadian Conference on Computer and Robot Vision (CRV '07). (Year: 2007).*

Crawford et al., "Ensuring navigation integrity using robotics in spine surgery," (Apr. 15, 2019), Journal of Robotic Surgery (2020) 14:177-183. (Year: 2019).*

* cited by examiner

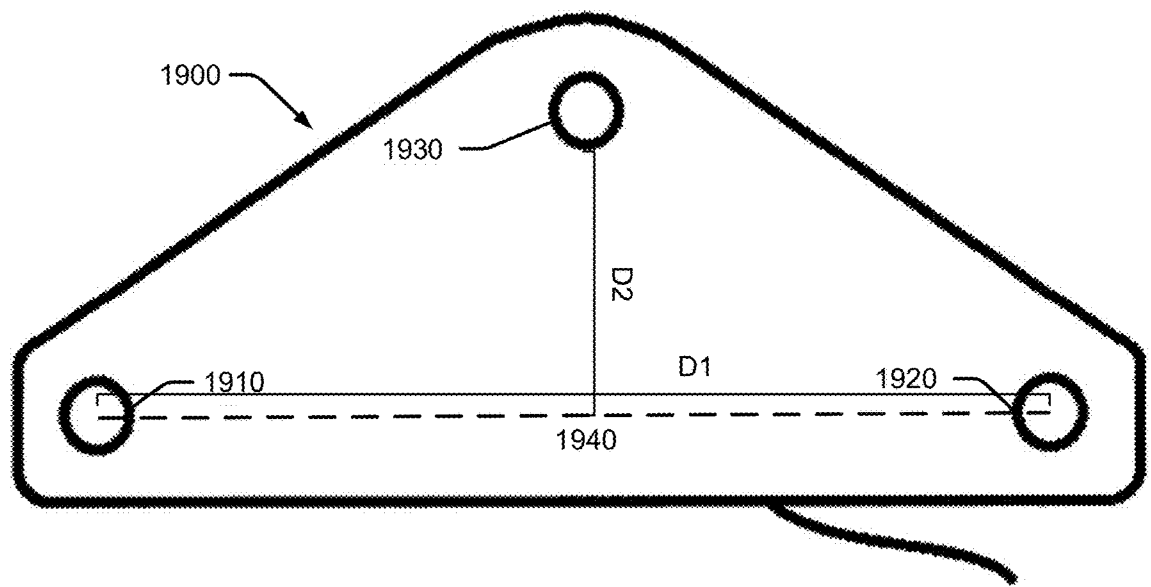
*Figure 19*
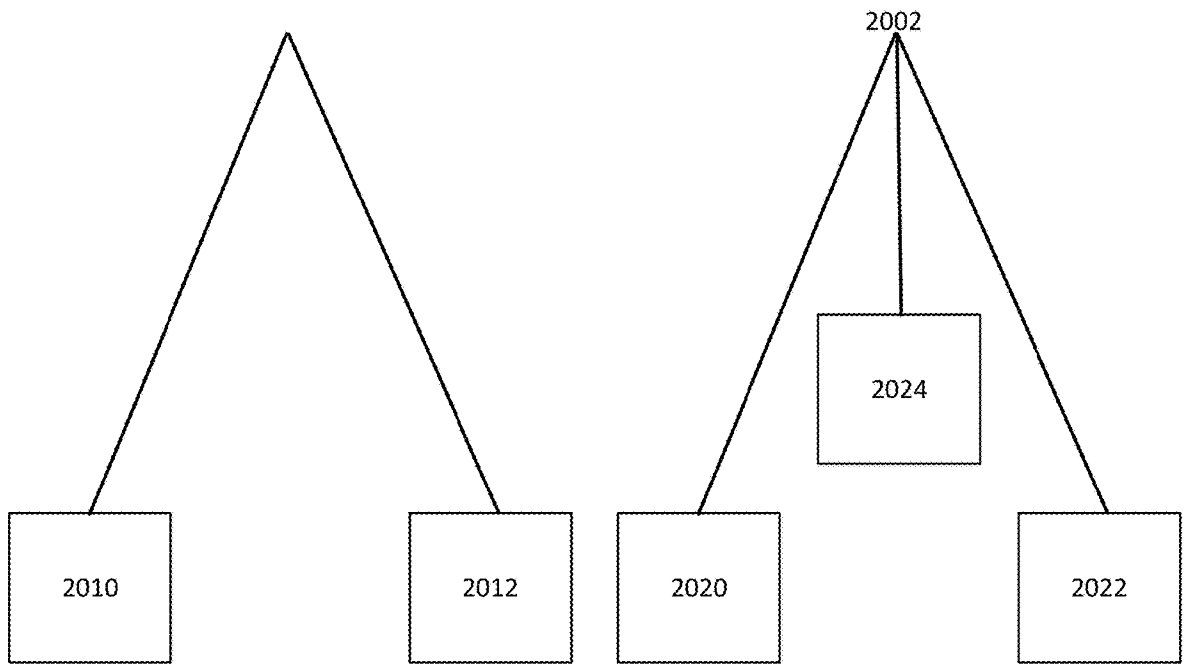
*Figure 20a*
*Figure 20b*

Left Camera Perspective

Right Camera Perspective

SURGICAL OBJECT TRACKING IN VISIBLE LIGHT VIA FIDUCIAL SEEDING AND SYNTHETIC IMAGE REGISTRATION

FIELD

The present disclosure relates to medical devices and systems, and more particularly, camera tracking systems used for computer assisted navigation during surgery.

BACKGROUND

Computer assisted navigation during surgery can provide a surgeon with computerized visualization of the present pose of a surgical tool relative to medical images of a patient's anatomy. Camera tracking systems for computer assisted navigation use one or more stereo camera systems to track a set of fiducials attached to a surgical tool which is being positioned by a surgeon or other user during surgery. The set of fiducials, also referred to as a dynamic reference array, allows the camera tracking system to determine a pose of the surgical tool relative to anatomical structure within a medical image and relative to a patient for display to the surgeon. The surgeon can thereby use the real-time pose feedback to navigate the surgical tool during a surgical procedure.

Navigated surgery procedures using existing navigation systems are prone to events triggering intermittent pauses when tracked objects are moved outside a tracking area of the camera system or become obstructed from camera view by intervening personnel and/or equipment. There is also a need to improve the tracking accuracy of navigation systems.

SUMMARY

Some embodiments are directed to a camera tracking system for computer assisted navigation during surgery is provided. The camera tracking system can include a camera bar, first and second tracking cameras, and a third tracking camera. The first and second tracking cameras can be attached at spaced apart locations on the camera bar. The third tracking camera can be attached at a location on the camera bar that is between locations of the first and second tracking cameras and spaced apart a distance from a line extending through centers of the first and second tracking cameras.

Some other embodiments are directed to a surgical tool tracking array. The surgical tool tracking array can include a multifaced reference array, a plurality of different optically coded patterns, and a tool holder. The multifaced reference array can have a plurality of planar faces. The plurality of different optically coded patterns can each be on a different one of the planar faces. The tool holder can be configured to couple a portion of a surgical tool to the surgical tool tracking array.

Still some other embodiments are directed to a surgical system that includes a camera tracking system, a surgical robot, and at least one controller.

The camera tracking system can include a camera bar, first and second tracking cameras, a third tracking camera, and at least one processor. The first and second tracking cameras can be attached at spaced apart locations on the camera bar. The third tracking camera can be attached at a location on the camera bar that is between locations of the first and second tracking cameras and spaced apart a distance from a line extending through centers of the first and second tracking cameras. The at least one processor can be operative to determine pose of a set of physical objects in three dimensional space based on triangulating locations of the objects imaged in video streams from the first, second, and third tracking cameras to locations of the first, second and third tracking cameras spaced apart in the three dimensional space.

The surgical robot can include a robot base, a robot arm, and at least one motor. The robot arm can be connected to the robot base, and be configured to connect to an end effector which guides movement of a surgical tool. The at least one motor can be operatively connected to move the robot arm relative to the robot base.

The at least one controller can be connected to the at least one motor and be configured to determine a pose of the end effector relative to a planned pose of the end effector while guiding movement of the surgical tool to operate on a patient. Additionally, the at least one controller can also be configured to generate steering information based on comparison of the planned pose and the determined pose of the end effector, wherein the steering information indicates where the end effector needs to be moved to become aligned with the planned pose so the surgical tool will be guided by the end effector along a planned trajectory toward the patient.

Other surgical systems, camera tracking systems, and surgical tool tracking array according to embodiments will be or become apparent to one with skill in the art upon review of the following drawings and detailed description. It is intended that all such surgical systems, camera tracking systems, and surgical tool tracking array be included within this description, be within the scope of the present disclosure, and be protected by the accompanying claims. Moreover, it is intended that all embodiments disclosed herein can be implemented separately or combined in any way and/or combination.

BRIEF DESCRIPTION OF THE DRAWINGS

The accompanying drawings, which are included to provide a further understanding of the disclosure and are incorporated in a constitute a part of this application, illustrate certain non-limiting embodiments of inventive concepts. In the drawings:

FIG. 19 illustrates an example configuration of a surgical tool tracking array with a camera bar having three stereo tracking cameras configured in accordance with some embodiments of the present disclosure;

FIG. 20*a* illustrates a single point stereo camera triangulation using two tracking cameras;

FIG. 20*b* illustrates a single point triangulation using three tracking cameras in accordance with some embodiments of the present disclosure;

DETAILED DESCRIPTION

Inventive concepts will now be described more fully hereinafter with reference to the accompanying drawings, in which examples of embodiments of inventive concepts are shown. Inventive concepts may, however, be embodied in many different forms and should not be construed as limited to the embodiments set forth herein. Rather, these embodiments are provided so that this disclosure will be thorough and complete, and will fully convey the scope of various present inventive concepts to those skilled in the art. It should also be noted that these embodiments are not mutually exclusive. Components from one embodiment may be tacitly assumed to be present or used in another embodiment.

Various embodiments disclosed herein are directed to improvements in computer assisted navigation during surgery. An extended reality (XR) headset is operatively connected to the surgical system and configured to provide an interactive environment through which a surgeon, assistant, and/or other personnel can view and select among patient images, view and select among computer generated surgery navigation information, and/or control surgical equipment in the operating room. As will be explained below, the XR headset may be configured to augment a real-world scene with computer generated XR images. The XR headset may be configured to provide an augmented reality (AR) viewing environment by displaying the computer generated XR images on a see-through display screen that allows light from the real-world scene to pass therethrough for combined viewing by the user. Alternatively, the XR headset may be configured to provide a virtual reality (VR) viewing environment by preventing or substantially preventing light from the real-world scene from being directly viewed by the user while the user is viewing the computer generated AR images on a display screen. An XR headset can be configured to provide both AR and VR viewing environments. In one embodiment, both AR and VR viewing environments are provided by lateral bands of substantially differing opacity arranged between the see-through display screen and the real-world scene, so that a VR viewing environment is provided for XR images aligned with a high opacity band and an AR viewing environment is provided for XR images aligned with the low opacity band. In another embodiment, both AR and VR viewing environments are provided by computer adjustable control of an opacity filter that variably constrains how much light from the real-world scene passes through a see-through display screen for combining with the XR images viewed by the user. Thus, the XR headset can also be referred to as an AR headset or a VR headset.

Figure 1:
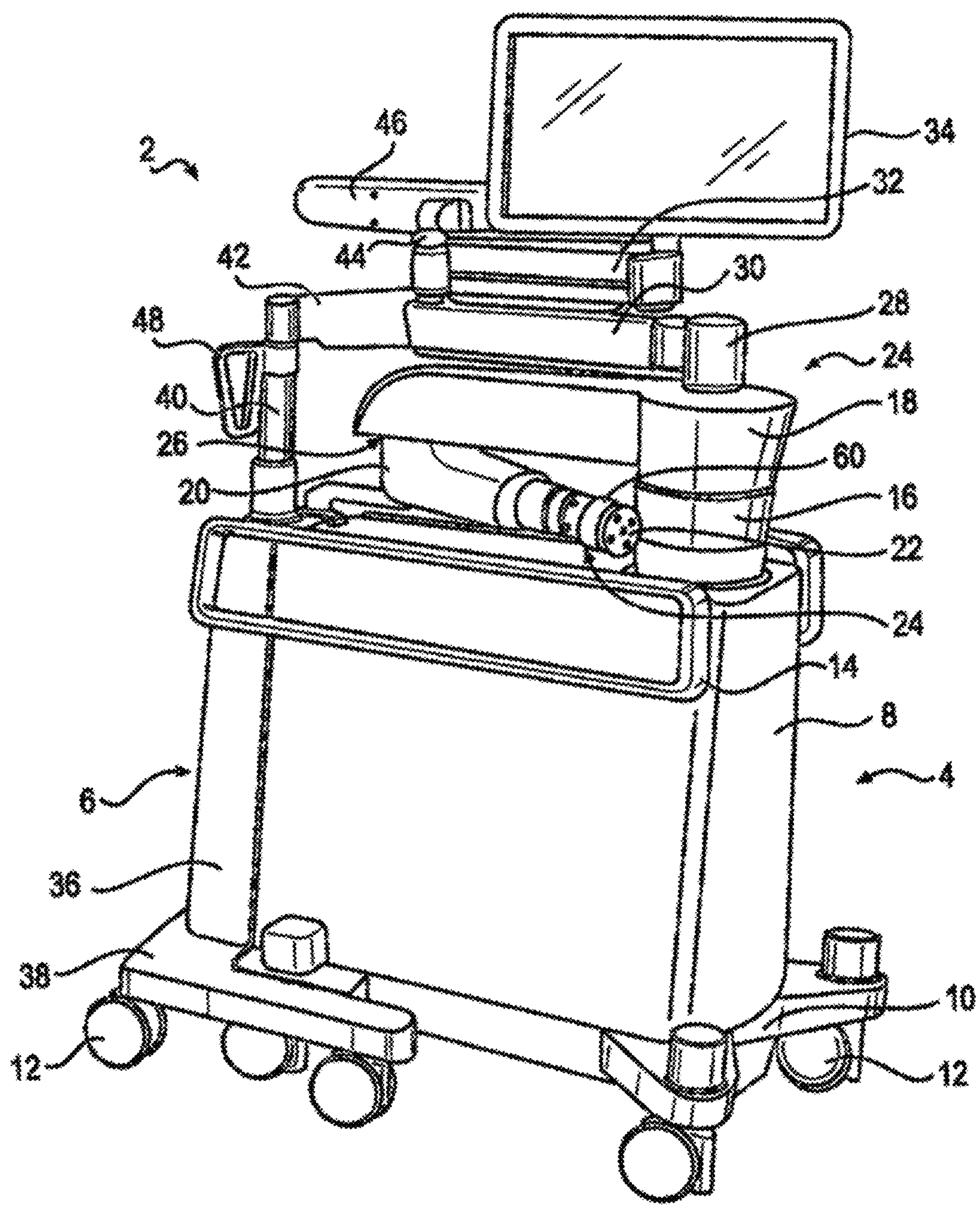
FIG. 1 illustrates an embodiment of a surgical system according to some embodiments of the present disclosure.

FIG. 1 illustrates an embodiment of a surgical system 2 according to some embodiments of the present disclosure. Prior to performance of an orthopedic or other surgical procedure, a three-dimensional ("3D") image scan may be taken of a planned surgical area of a patient using, e.g., the C-Arm imaging device 104 of FIG. 10 or O-Arm imaging device 106 of FIG. 11, or from another medical imaging device such as a computed tomography (CT) image or MRI. This scan can be taken pre-operatively (e.g. few weeks before procedure, most common) or intra-operatively. However, any known 3D or 2D image scan may be used in accordance with various embodiments of the surgical system 2. The image scan is sent to a computer platform in communication with the surgical system 2, such as the computer platform 910 of the surgical system 900 (FIG. 9) which may include the camera tracking system component 6, the surgical robot 4 (e.g., robot 2 in FIG. 1), imaging devices (e.g., C-Arm 104, O-Arm 106, etc.), and an image database 950 for storing image scans of patients. A surgeon reviewing the image scan(s) on a display device of the computer platform 910 (FIG. 9) generates a surgical plan defining a target pose for a surgical tool to be used during a surgical procedure on an anatomical structure of the patient. Example surgical tools, also referred to as tools, can include, without limitation, drills, screw drivers, saws, retractors, and implants such as a screws, spacers, interbody fusion devices, plates, rods, etc. In some embodiments, the surgical plan defining the target plane is planned on the 3D image scan displayed on a display device.

As used herein, the term "pose" refers to the position and/or the rotational angle of one object (e.g., dynamic reference array, end effector, surgical tool, anatomical structure, etc.) relative to another object and/or to a defined coordinate system. A pose may therefore be defined based on only the multidimensional position of one object relative to another object and/or to a defined coordinate system, only on the multidimensional rotational angles of the object relative to another object and/or to a defined coordinate system, or on a combination of the multidimensional position and the multidimensional rotational angles. The term "pose" therefore is used to refer to position, rotational angle, or combination thereof.

The surgical system 2 of FIG. 1 can assist surgeons during medical procedures by, for example, holding tools, aligning tools, using tools, guiding tools, and/or positioning tools for use. In some embodiments, surgical system 2 includes a surgical robot 4 and a camera tracking system component 6. The ability to mechanically couple surgical robot 4 and camera tracking system component 6 can allow for surgical system 2 to maneuver and move as a single unit, and allow surgical system 2 to have a small footprint in an area, allow easier movement through narrow passages and around turns, and allow storage within a smaller area.

A surgical procedure may begin with the surgical system 2 moving from medical storage to a medical procedure room. The surgical system 2 may be maneuvered through doorways, halls, and elevators to reach a medical procedure room. Within the room, the surgical system 2 may be physically separated into two separate and distinct systems, the surgical robot 4 and the camera tracking system component 6. Surgical robot 4 may be positioned adjacent the patient at any suitable location to properly assist medical personnel. Camera tracking system component 6 may be positioned at the base of the patient, at the patient shoulders, or any other location suitable to track the present pose and movement of the pose of tracks portions of the surgical robot 4 and the patient. Surgical robot 4 and camera tracking system component 6 may be powered by an onboard power source and/or plugged into an external wall outlet.

Surgical robot 4 may be used to assist a surgeon by holding and/or using tools during a medical procedure. To properly utilize and hold tools, surgical robot 4 may rely on a plurality of motors, computers, and/or actuators to function properly. Illustrated in FIG. 1, robot body 8 may act as the structure in which the plurality of motors, computers, and/or actuators may be secured within surgical robot 4. Robot body 8 may also provide support for robot telescoping support 16. The size of robot body 8 may provide a solid platform supporting attached components, and may house, conceal, and protect the plurality of motors, computers, and/or actuators that may operate attached components.

Robot base 10 may act as a lower support for surgical robot 4. In some embodiments, robot base 10 may support robot body 8 and may attach robot body 8 to a plurality of powered wheels 12. This attachment to wheels may allow robot body 8 to move in space efficiently. Robot base 10 may run the length and width of robot body 8. Robot base 10 may be about two inches to about 10 inches tall. Robot base 10 may cover, protect, and support powered wheels 12.

In some embodiments, as illustrated in FIG. 1, at least one powered wheel 12 may be attached to robot base 10. Powered wheels 12 may attach to robot base 10 at any location. Each individual powered wheel 12 may rotate about a vertical axis in any direction. A motor may be disposed above, within, or adjacent to powered wheel 12. This motor may allow for surgical system 2 to maneuver into any location and stabilize and/or level surgical system 2. A rod, located within or adjacent to powered wheel 12, may be pressed into a surface by the motor. The rod, not pictured, may be made of any suitable metal to lift surgical system 2. The rod may lift powered wheel 10, which may lift surgical system 2, to any height required to level or otherwise fix the orientation of the surgical system 2 in relation to a patient. The weight of surgical system 2, supported through small contact areas by the rod on each wheel, prevents surgical system 2 from moving during a medical procedure. This rigid positioning may prevent objects and/or people from moving surgical system 2 by accident.

Moving surgical system 2 may be facilitated using robot railing 14. Robot railing 14 provides a person with the ability to move surgical system 2 without grasping robot body 8. As illustrated in FIG. 1, robot railing 14 may run the length of robot body 8, shorter than robot body 8, and/or may run longer the length of robot body 8. Robot railing 14 may further provide protection to robot body 8, preventing objects and or personnel from touching, hitting, or bumping into robot body 8.

Robot body 8 may provide support for a Selective Compliance Articulated Robot Arm, hereafter referred to as a "SCARA." A SCARA 24 may be beneficial to use within the surgical system 2 due to the repeatability and compactness of the robotic arm. The compactness of a SCARA may provide additional space within a medical procedure, which may allow medical professionals to perform medical procedures free of excess clutter and confining areas. SCARA 24 may comprise robot telescoping support 16, robot support arm 18, and/or robot arm 20. Robot telescoping support 16 may be disposed along robot body 8. As illustrated in FIG. 1, robot telescoping support 16 may provide support for the SCARA 24 and display 34. In some embodiments, robot telescoping support 16 may extend and contract in a vertical direction. The body of robot telescoping support 16 may be any width and/or height configured to support the stress and weight placed upon it.

In some embodiments, medical personnel may move SCARA 24 through a command submitted by the medical personnel. The command may originate from input received on display 34, a tablet, and/or an XR headset (e.g., headset 920 in FIG. 9) as will be explained in further detail below. The XR headset may eliminate the need for medical personnel to refer to any other display such as the display 34 or a tablet, which enables the SCARA 24 to be configured without the display 34 and/or the tablet. The command may be generated by the depression of a switch and/or the depression of a plurality of switches, and/or may be generated based on a hand gesture command and/or voice command that is sensed by the XR headset as will be explained in further detail below.

Figure 5:
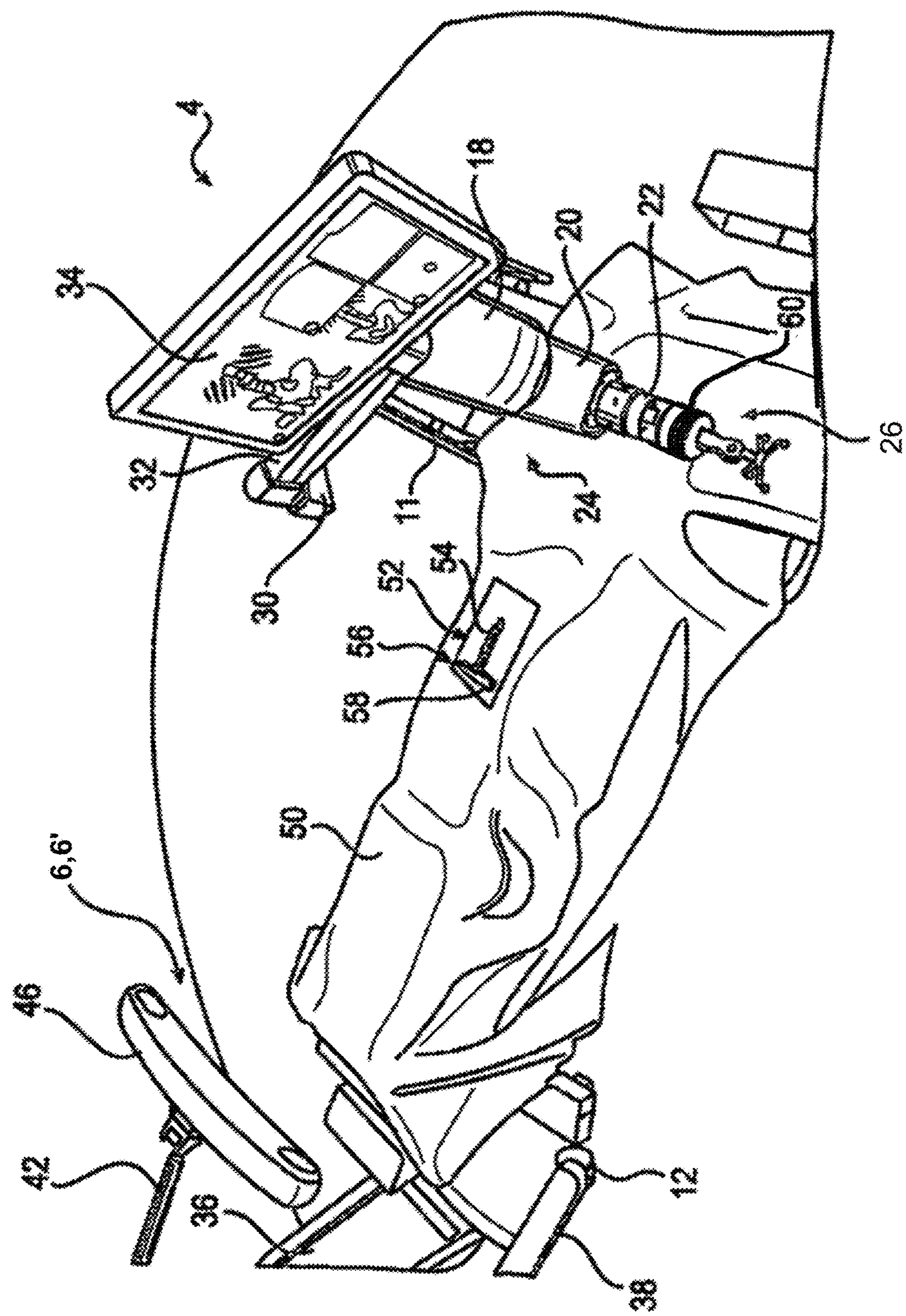
FIG. 5 illustrates a medical operation in which a surgical robot and a camera system are disposed around a patient.

As shown in FIG. 5, an activation assembly 60 may include a switch and/or a plurality of switches. The activation assembly 60 may be operable to transmit a move command to the SCARA 24 allowing an operator to manually manipulate the SCARA 24. When the switch, or plurality of switches, is depressed the medical personnel may have the ability to move SCARA 24 through applied hand movements. Alternatively or additionally, an operator may control movement of the SCARA 24 through hand gesture commands and/or voice commands that are sensed by the XR headset as will be explained in further detail below. Additionally, when the SCARA 24 is not receiving a command to move, the SCARA 24 may lock in place to prevent accidental movement by personnel and/or other objects. By locking in place, the SCARA 24 provides a solid platform through which the end effector 26 can guide a surgical tool during a medical procedure.

Robot support arm 18 can be connected to robot telescoping support 16 by various mechanisms. In some embodiments, best seen in FIGS. 1 and 2, robot support arm 18 rotates in any direction in regard to robot telescoping support 16. Robot support arm 18 may rotate three hundred and sixty degrees around robot telescoping support 16. Robot arm 20 may connect to robot support arm 18 at any suitable location and by various mechanisms that enable rotation in any direction relative to robot support arm 18. In one embodiment, the robot arm 20 can rotate three hundred and sixty degrees relative to the robot support arm 18. This free rotation allows an operator to position robot arm 20 according to a surgical plan.

Figure 4:
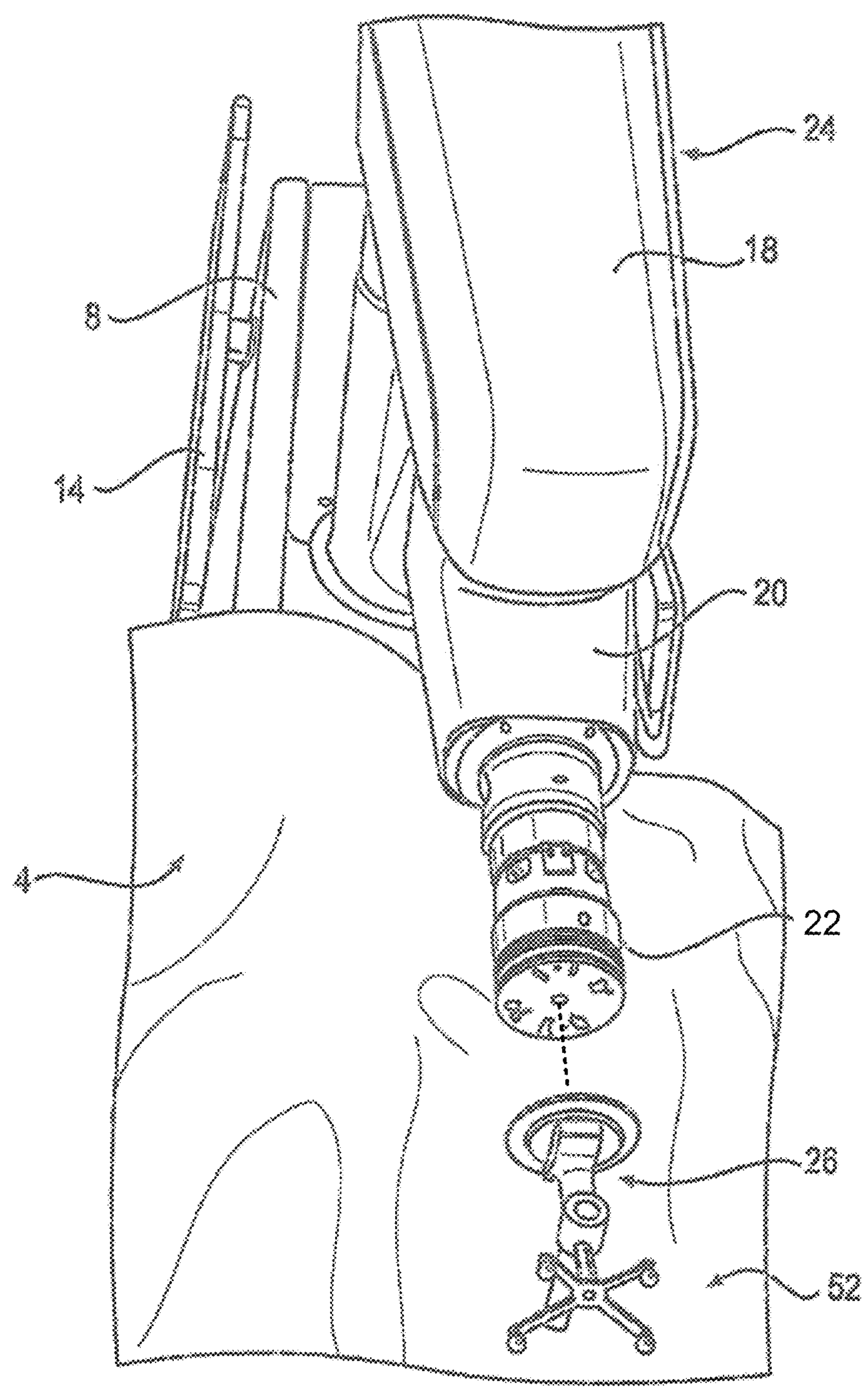
FIG. 4 illustrates an embodiment of an end effector that is connectable to a robot arm and configured according to some embodiments of the present disclosure.

The end effector 26 shown in FIGS. 4 and 5 may attach to robot arm 20 in any suitable location. The end effector 26 can be configured to attach to an end effector coupler 22 of the robot arm 20 positioned by the surgical robot 4. The example end effector 26 includes a tubular guide that guides movement of an inserted surgical tool relative to an anatomical structure on which a surgical procedure is to be performed.

In some embodiments, a dynamic reference array 52 is attached to the end effector 26. Dynamic reference arrays, also referred to as "DRAB" and "reference arrays" herein, can be rigid bodies, markers, or other indicia which may be attached or formed on one or more XR headsets being worn by personnel in the operating room, the end effector, the surgical robot, a surgical tool in a navigated surgical procedure, and an anatomical structure (e.g., bone) of a patient. The computer platform 910 in combination with the camera tracking system component 6 or other 3D localization system are configured to track in real-time the pose (e.g., positions and rotational orientations) of the DRA. The DRA can include fiducials, such as the illustrated arrangement of balls. This tracking of 3D coordinates of the DRA can allow the surgical system 2 to determine the pose of the DRA in any multidimensional space in relation to the target anatomical structure of the patient 50 in FIG. 5.

Figure 2:
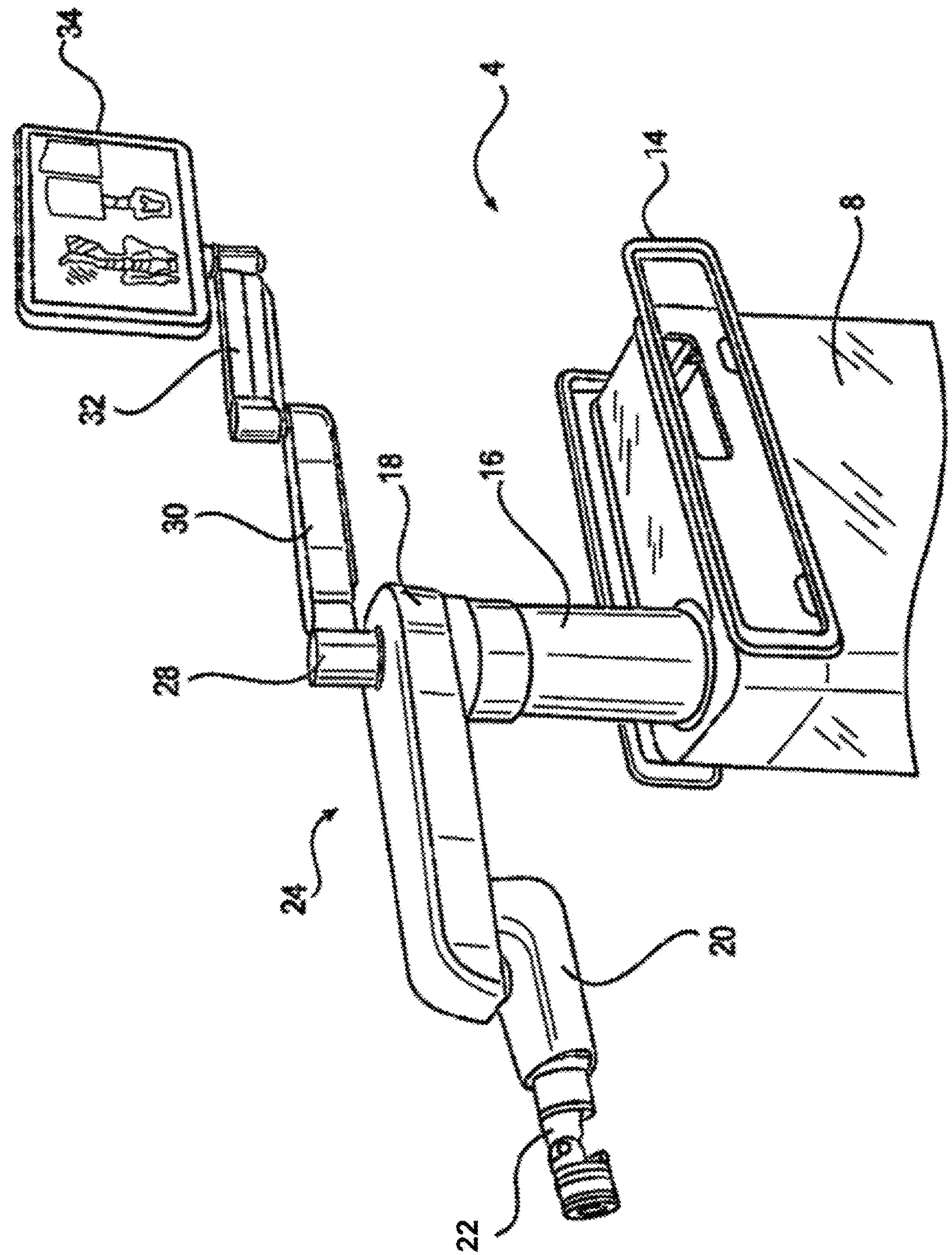
FIG. 2 illustrates a surgical robot component of the surgical system of FIG. 1 according to some embodiments of the present disclosure.

As illustrated in FIG. 1, a light indicator 28 may be positioned on top of the SCARA 24. Light indicator 28 may illuminate as any type of light to indicate "conditions" in which surgical system 2 is currently operating. In some embodiments, the light may be produced by LED bulbs, which may form a ring around light indicator 28. Light indicator 28 may comprise a fully permeable material that can let light shine through the entirety of light indicator 28. Light indicator 28 may be attached to lower display support 30. Lower display support 30, as illustrated in FIG. 2 may allow an operator to maneuver display 34 to any suitable location. Lower display support 30 may attach to light indicator 28 by any suitable mechanism. In some embodiments, lower display support 30 may rotate about light indicator 28 or be rigidly attached thereto. Upper display support 32 may attach to lower display support 30 by any suitable mechanism.

In some embodiments, a tablet may be used in conjunction with display 34 and/or without display 34. The tablet may be disposed on upper display support 32, in place of display 34, and may be removable from upper display support 32 during a medical operation. In addition the tablet may communicate with display 34. The tablet may be able to connect to surgical robot 4 by any suitable wireless and/or wired connection. In some embodiments, the tablet may be able to program and/or control surgical system 2 during a medical operation. When controlling surgical system 2 with the tablet, all input and output commands may be duplicated on display 34. The use of a tablet may allow an operator to manipulate surgical robot 4 without having to move around patient 50 and/or to surgical robot 4.

As will be explained below, in some embodiments a surgeon and/or other personnel can wear XR headsets that may be used in conjunction with display 34 and/or a tablet or the XR head(s) may eliminate the need for use of the display 34 and/or tablet.

Figure 3A:
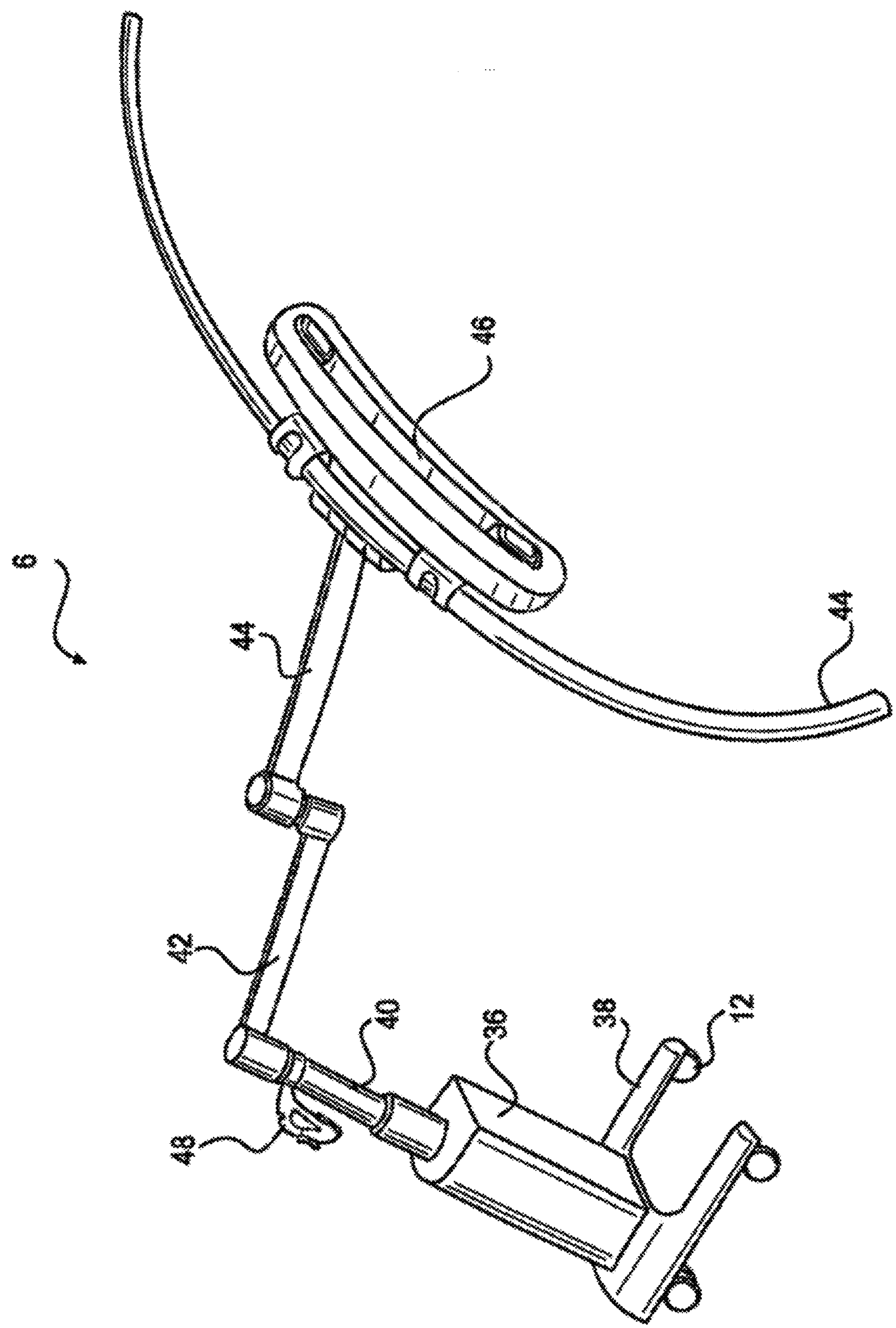
FIG. 3A illustrates a camera tracking system component of the surgical system of FIG. 1 according to some embodiments of the present disclosure.

As illustrated in FIGS. 3A and 5, camera tracking system component 6 works in conjunction with surgical robot 4 through wired or wireless communication networks. Referring to FIGS. 1, 3 and 5, camera tracking system component 6 can include some similar components to the surgical robot 4. For example, camera body 36 may provide the functionality found in robot body 8. Robot body 8 may provide an auxiliary tracking bar upon which cameras 46 are mounted. The structure within robot body 8 may also provide support for the electronics, communication devices, and power supplies used to operate camera tracking system component 6. Camera body 36 may be made of the same material as robot body 8. Camera tracking system component 6 may communicate directly to an XR headset, tablet and/or display 34 by a wireless and/or wired network to enable the XR headset, tablet and/or display 34 to control the functions of camera tracking system component 6.

Camera body 36 is supported by camera base 38. Camera base 38 may function as robot base 10. In the embodiment of FIG. 1, camera base 38 may be wider than robot base 10. The width of camera base 38 may allow for camera tracking system component 6 to connect with surgical robot 4. As illustrated in FIG. 1, the width of camera base 38 may be large enough to fit outside robot base 10. When camera tracking system component 6 and surgical robot 4 are connected, the additional width of camera base 38 may allow surgical system 2 additional maneuverability and support for surgical system 2.

As with robot base 10, a plurality of powered wheels 12 may attach to camera base 38. Powered wheel 12 may allow camera tracking system component 6 to stabilize and level or set fixed orientation in regards to patient 50, similar to the operation of robot base 10 and powered wheels 12. This stabilization may prevent camera tracking system component 6 from moving during a medical procedure and may keep cameras 46 on the auxiliary tracking bar from losing track of a DRA connected to an XR headset and/or the surgical robot 4, and/or losing track of one or more DRAs 52 connected to an anatomical structure 54 and/or tool 58 within a designated area 56 as shown in FIGS. 3A and 5. This stability and maintenance of tracking enhances the ability of surgical robot 4 to operate effectively with camera tracking system component 6. Additionally, the wide camera base 38 may provide additional support to camera tracking system component 6. Specifically, a wide camera base 38 may prevent camera tracking system component 6 from tipping over when cameras 46 is disposed over a patient, as illustrated in FIGS. 3A and 5.

Camera telescoping support 40 may support cameras 46 on the auxiliary tracking bar. In some embodiments, telescoping support 40 moves cameras 46 higher or lower in the vertical direction. Camera handle 48 may be attached to camera telescoping support 40 at any suitable location and configured to allow an operator to move camera tracking system component 6 into a planned position before a medical operation. In some embodiments, camera handle 48 is used to lower and raise camera telescoping support 40. Camera handle 48 may perform the raising and lowering of camera telescoping support 40 through the depression of a button, switch, lever, and/or any combination thereof.

Lower camera support arm 42 may attach to camera telescoping support 40 at any suitable location, in embodiments, as illustrated in FIG. 1, lower camera support arm 42 may rotate three hundred and sixty degrees around telescoping support 40. This free rotation may allow an operator to position cameras 46 in any suitable location. Lower camera support arm 42 may connect to telescoping support 40 by any suitable mechanism. Lower camera support arm 42 may be used to provide support for cameras 46. Cameras 46 may be attached to lower camera support arm 42 by any suitable mechanism. Cameras 46 may pivot in any direction at the attachment area between cameras 46 and lower camera support arm 42. In embodiments a curved rail 44 may be disposed on lower camera support arm 42.

Curved rail 44 may be disposed at any suitable location on lower camera support arm 42. As illustrated in FIG. 3A, curved rail 44 may attach to lower camera support arm 42 by any suitable mechanism. Curved rail 44 may be of any suitable shape, a suitable shape may be a crescent, circular, oval, elliptical, and/or any combination thereof. Cameras 46 may be moveably disposed along curved rail 44. Cameras 46 may attach to curved rail 44 by, for example, rollers, brackets, braces, motors, and/or any combination thereof. Motors and rollers, not illustrated, may be used to move cameras 46 along curved rail 44. As illustrated in FIG. 3A, during a medical procedure, if an object prevents cameras 46 from viewing one or more DRAs being tracked, the motors may responsively move cameras 46 along curved rail 44. This motorized movement may allow cameras 46 to move to a new position that is no longer obstructed by the object without moving camera tracking system component 6. While cameras 46 is obstructed from viewing one or more tracked DRAs, camera tracking system component 6 may send a stop signal to a surgical robot 4, XR headset, display 34, and/or a tablet. The stop signal may prevent SCARA 24 from moving until cameras 46 has reacquired tracked DRAs 52 and/or can warn an operator wearing the XR headset and/or viewing the display 34 and/or the tablet. This SCARA 24 can be configured to respond to receipt of a stop signal by stopping further movement of the base and/or end effector coupler 22 until the camera tracking system can resume tracking of DRAs.

Figure 3C:
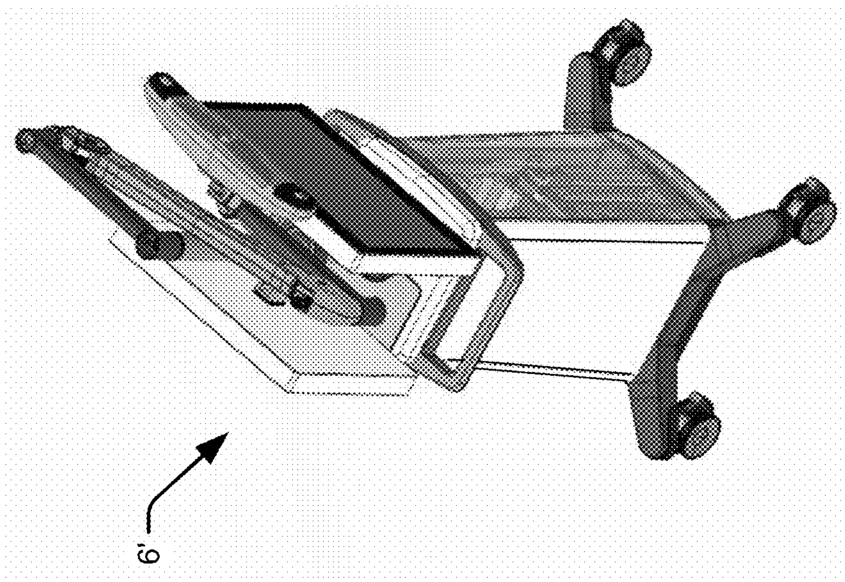
FIGS. 3B and 3C illustrate a front view and isometric view of another camera tracking system component which may be used with the surgical system of FIG. 1 according to some embodiments of the present disclosure.
Figure 3B:
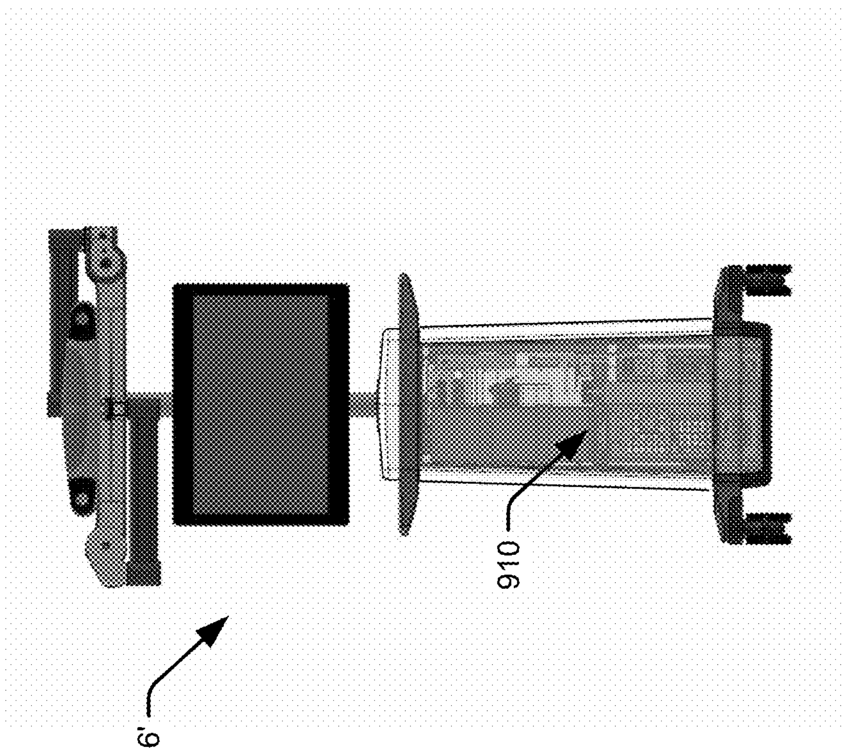

FIGS. 3B and 3C illustrate a front view and isometric view of another camera tracking system component 6' which may be used with the surgical system of FIG. 1 or may be used independent of a surgical robot. For example, the camera tracking system component 6' may be used for providing navigated surgery without use of robotic guidance. One of the differences between the camera tracking system component 6' of FIGS. 3B and 3C and the camera tracking system component 6 of FIG. 3A, is that the camera tracking system component 6' of FIGS. 3B and 3C includes a housing that transports the computer platform 910. The computer platform 910 can be configured to perform camera tracking operations to track DRAs, perform navigated surgery operations that provide surgical navigation information to a display device, e.g., XR headset and/or other display device, and perform other computational operations disclosed herein. The computer platform 910 can therefore include a navigation computer, such as one or more of the navigation computers of FIG. 14.

Figure 6:
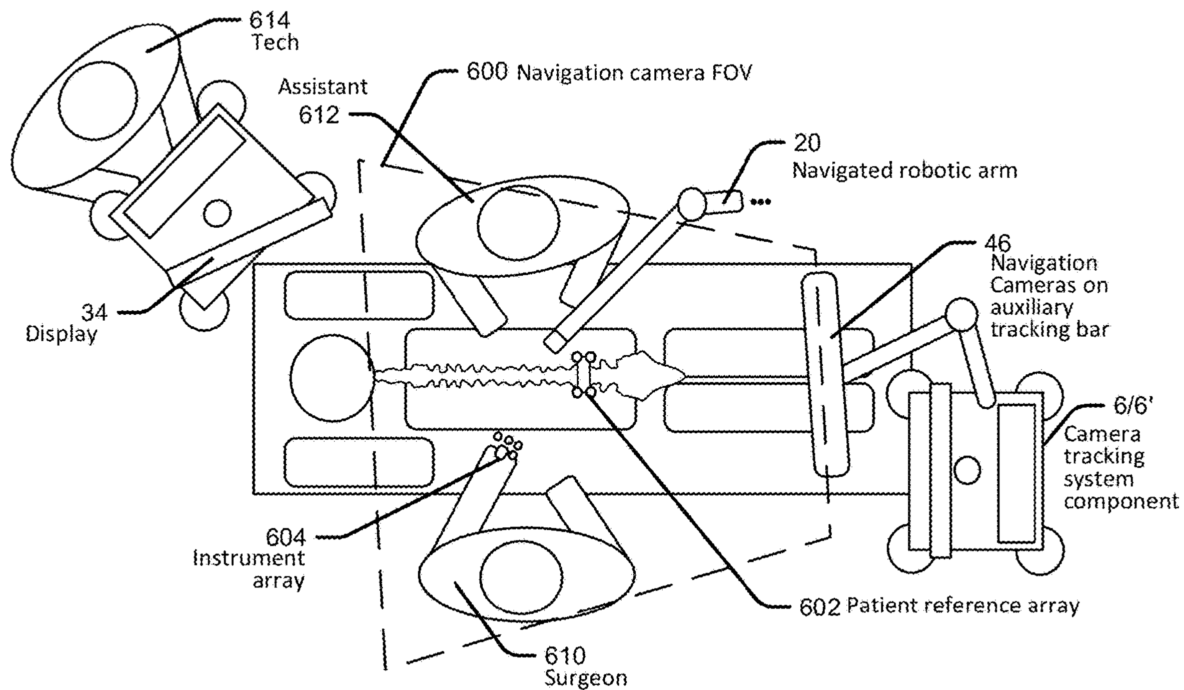
FIG. 6 illustrates a block diagram view of the components of the surgical system of FIG. 5 being used for a medical operation.

FIG. 6 illustrates a block diagram view of the components of the surgical system of FIG. 5 used for the medical operation. Referring to FIG. 6, the tracking cameras 46 on the auxiliary tracking bar has a navigation field-of-view 600 in which the pose (e.g., position and orientation) of the reference array 602 attached to the patient, the reference array 604 attached to the surgical instrument, and the robot arm 20 are tracked. The tracking cameras 46 may be part of the camera tracking system component 6' of FIGS. 3B and 3C, which includes the computer platform 910 configured to perform the operations described below. The reference arrays enable tracking by reflecting light in known patterns, which are decoded to determine their respective poses by the tracking subsystem of the surgical robot 4. If the line-of-sight between the patient reference array 602 and the tracking cameras 46 in the auxiliary tracking bar is blocked (for example, by a medical personnel, instrument, etc.), further navigation of the surgical instrument may not be able to be performed and a responsive notification may temporarily halt further movement of the robot arm 20 and surgical robot 4, display a warning on the display 34, and/or provide an audible warning to medical personnel. The display 34 is accessible to the surgeon 610 and assistant 612 but viewing requires a head to be turned away from the patient and for eye focus to be changed to a different distance and location. The navigation software may be controlled by a tech personnel 614 based on vocal instructions from the surgeon.

Figure 7:
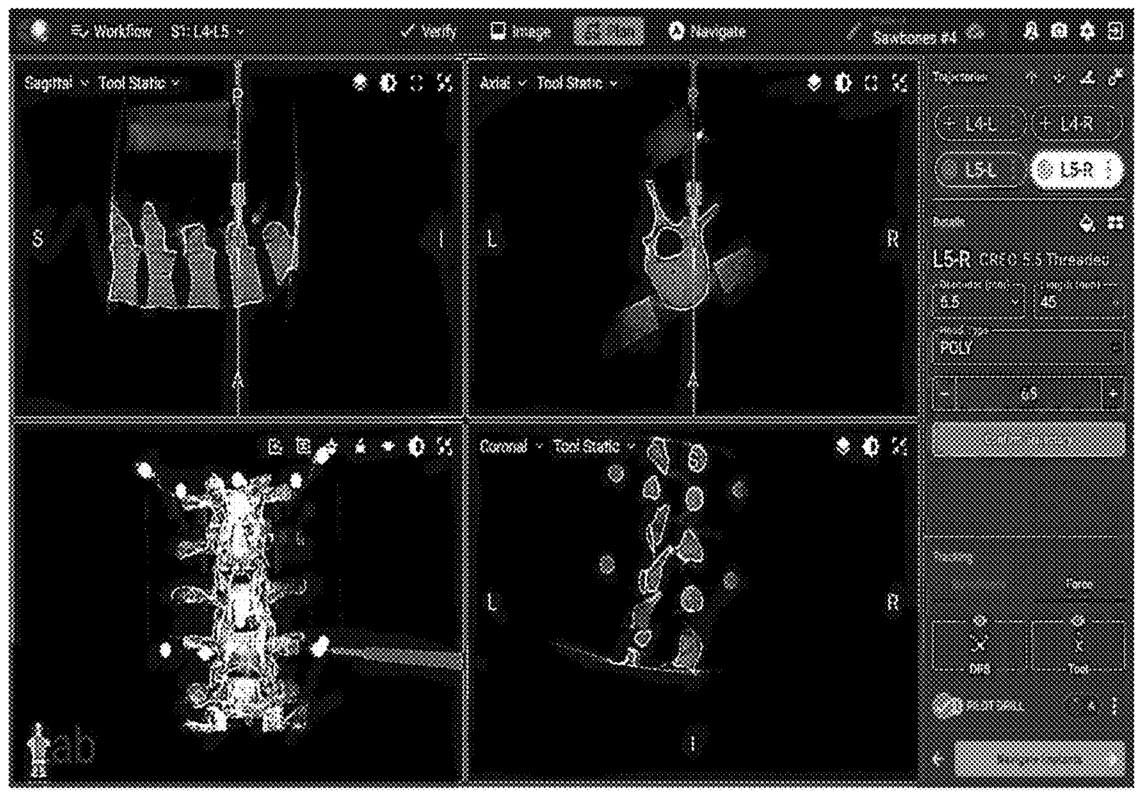
FIG. 7 illustrates various display screens that may be displayed on the display of FIGS. 5 and 6 when using a navigation function of the surgical system.

FIG. 7 illustrates various display screens that may be displayed on the display 34 of FIGS. 5 and 6 by the surgical robot 4 when using a navigation function of the surgical system 2. The display screens can include, without limitation, patient radiographs with overlaid graphical representations of models of instruments that are positioned in the display screens relative to the anatomical structure based on a developed surgical plan and/or based on poses of tracked reference arrays, various user selectable menus for controlling different stages of the surgical procedure and dimension parameters of a virtually projected implant (e.g. length, width, and/or diameter).

For navigated surgery, various processing components (e.g., computer platform 910) and associated software described below are provided that enable pre-operatively planning of a surgical procedure, e.g., implant placement, and electronic transfer of the plan to computer platform 910 to provide navigation information to one or more users during the planned surgical procedure.

For robotic navigation, various processing components (e.g., computer platform 910) and associated software described below are provided that enable pre-operatively planning of a surgical procedure, e.g., implant placement, and electronic transfer of the plan to the surgical robot 4. The surgical robot 4 uses the plan to guide the robot arm 20 and connected end effector 26 to provide a target pose for a surgical tool relative to a patient anatomical structure for a step of the planned surgical procedure.

Various embodiments below are directed to using one or more XR headsets that can be worn by the surgeon 610, the assistant 612, and/or other medical personnel to provide an improved user interface for receiving information from and/or providing control commands to the surgical robot, the camera tracking system component 6/6', and/or other medical equipment in the operating room.

Figure 8:
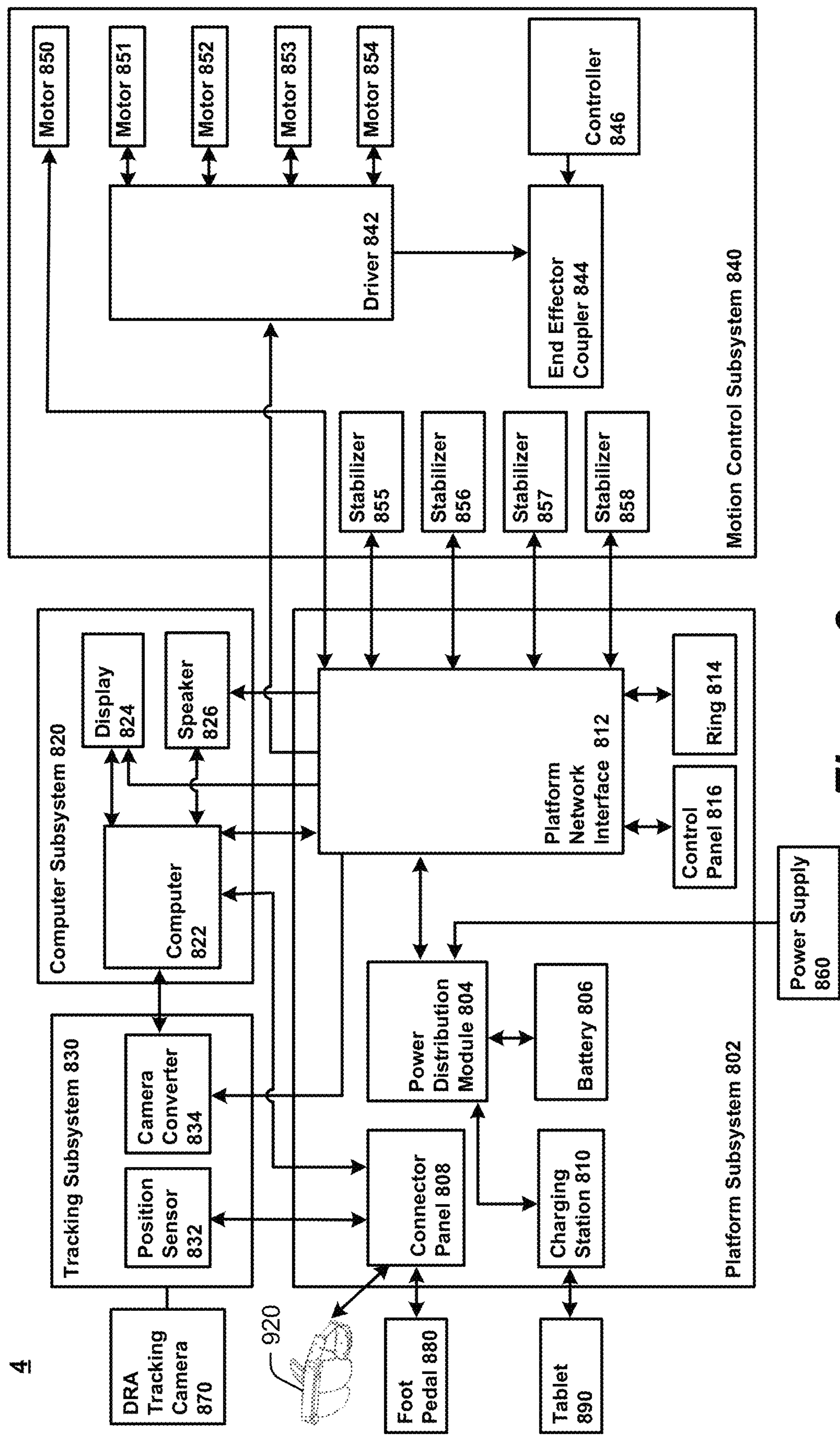
FIG. 8 illustrates a block diagram of some electrical components of a surgical robot according to some embodiments of the present disclosure.

FIG. 8 illustrates a block diagram of some electrical components of the surgical robot 4 according to some embodiments of the present disclosure. Referring to FIG. 8, a load cell (not shown) may be configured to track force applied to end effector coupler 22. In some embodiments the load cell may communicate with a plurality of motors 850, 851, 852, 853, and/or 854. As load cell senses force, information as to the amount of force applied may be distributed from a switch array and/or a plurality of switch arrays to a controller 846. Controller 846 may take the force information from load cell and process it with a switch algorithm. The switch algorithm is used by the controller 846 to control a motor driver 842. The motor driver 842 controls operation of one or more of the motors 850, 851, 852, 853, and 854. Motor driver 842 may direct a specific motor to produce, for example, an equal amount of force measured by load cell through the motor. In some embodiments, the force produced may come from a plurality of motors, e.g., 850-854, as directed by controller 846. Additionally, motor driver 842 may receive input from controller 846. Controller 846 may receive information from load cell as to the direction of force sensed by load cell. Controller 846 may process this information using a motion controller algorithm. The algorithm may be used to provide information to specific motor drivers 842. To replicate the direction of force, controller 846 may activate and/or deactivate certain motor drivers 842. Controller 846 may control one or more motors, e.g. one or more of 850-854, to induce motion of end effector 26 in the direction of force sensed by load cell. This force-controlled motion may allow an operator to move SCARA 24 and end effector 26 effortlessly and/or with very little resistance. Movement of end effector 26 can be performed to position end effector 26 in any suitable pose (i.e., location and angular orientation relative to defined three-dimensional (3D) orthogonal reference axes) for use by medical personnel.

Activation assembly 60, best illustrated in FIG. 5, may form of a bracelet that wraps around end effector coupler 22. The activation assembly 60 may be located on any part of SCARA 24, any part of end effector coupler 22, may be worn by medical personnel (and communicate wirelessly), and/or any combination thereof. Activation assembly 60 may comprise of a primary button and a secondary button.

Depressing primary button may allow an operator to move SCARA 24 and end effector coupler 22. According to one embodiment, once set in place, SCARA 24 and end effector coupler 22 may not move until an operator programs surgical robot 4 to move SCARA 24 and end effector coupler 22, or is moved using primary button. In some examples, it may require the depression of at least two non-adjacent primary activation switches before SCARA 24 and end effector coupler 22 will respond to operator commands. Depression of at least two primary activation switches may prevent the accidental movement of SCARA 24 and end effector coupler 22 during a medical procedure.

Activated by primary button, load cell may measure the force magnitude and/or direction exerted upon end effector coupler 22 by an operator, i.e. medical personnel. This information may be transferred to one or more motors, e.g. one or more of 850-854, within SCARA 24 that may be used to move SCARA 24 and end effector coupler 22. Information as to the magnitude and direction of force measured by load cell may cause the one or more motors, e.g. one or more of 850-854, to move SCARA 24 and end effector coupler 22 in the same direction as sensed by the load cell. This force-controlled movement may allow the operator to move SCARA 24 and end effector coupler 22 easily and without large amounts of exertion due to the motors moving SCARA 24 and end effector coupler 22 at the same time the operator is moving SCARA 24 and end effector coupler 22.

In some examples, a secondary button may be used by an operator as a "selection" device. During a medical operation, surgical robot 4 may notify medical personnel to certain conditions by the XR headset(s) 920, display 34 and/or light indicator 28. The XR headset(s) 920 are each configured to display images on a see-through display screen to form an extended reality image that is overlaid on real-world objects viewable through the see-through display screen. Medical personnel may be prompted by surgical robot 4 to select a function, mode, and/or assesses the condition of surgical system 2. Depressing secondary button a single time may activate certain functions, modes, and/or acknowledge information communicated to medical personnel through the XR headset(s) 920, display 34 and/or light indicator 28. Additionally, depressing the secondary button multiple times in rapid succession may activate additional functions, modes, and/or select information communicated to medical personnel through the XR headset(s) 920, display 34 and/or light indicator 28.

With further reference to FIG. 8, electrical components of the surgical robot 4 include platform subsystem 802, computer subsystem 820, motion control subsystem 840, and tracking subsystem 830. Platform subsystem 802 includes battery 806, power distribution module 804, connector panel 808, and charging station 810. Computer subsystem 820 includes computer 822, display 824, and speaker 826. Motion control subsystem 840 includes driver circuit 842, motors 850, 851, 852, 853, 854, stabilizers 855, 856, 857, 858, end effector connector 844, and controller 846. Tracking subsystem 830 includes position sensor 832 and camera converter 834. Surgical robot 4 may also include a removable foot pedal 880 and removable tablet computer 890.

Input power is supplied to surgical robot 4 via a power source which may be provided to power distribution module 804. Power distribution module 804 receives input power and is configured to generate different power supply voltages that are provided to other modules, components, and subsystems of surgical robot 4. Power distribution module 804 may be configured to provide different voltage supplies to connector panel 808, which may be provided to other components such as computer 822, display 824, speaker 826, driver 842 to, for example, power motors 850-854 and end effector coupler 844, and provided to camera converter 834 and other components for surgical robot 4. Power distribution module 804 may also be connected to battery 806, which serves as temporary power source in the event that power distribution module 804 does not receive power from an input power. At other times, power distribution module 804 may serve to charge battery 806.

Connector panel 808 may serve to connect different devices and components to surgical robot 4 and/or associated components and modules. Connector panel 808 may contain one or more ports that receive lines or connections from different components. For example, connector panel 808 may have a ground terminal port that may ground surgical robot 4 to other equipment, a port to connect foot pedal 880, a port to connect to tracking subsystem 830, which may include position sensor 832, camera converter 834, and DRA tracking cameras 870. Connector panel 808 may also include other ports to allow USB, Ethernet, HDMI communications to other components, such as computer 822. In accordance with some embodiments, the connector panel 808 can include a wired and/or wireless interface for operatively connecting one or more XR headsets 920 to the tracking subsystem 830 and/or the computer subsystem 820.

Control panel 816 may provide various buttons or indicators that control operation of surgical robot 4 and/or provide information from surgical robot 4 for observation by an operator. For example, control panel 816 may include buttons to power on or off surgical robot 4, lift or lower vertical column 16, and lift or lower stabilizers 855-858 that may be designed to engage casters 12 to lock surgical robot 4 from physically moving. Other buttons may stop surgical robot 4 in the event of an emergency, which may remove all motor power and apply mechanical brakes to stop all motion from occurring. Control panel 816 may also have indicators notifying the operator of certain system conditions such as a line power indicator or status of charge for battery 806. In accordance with some embodiments, one or more XR headsets 920 may communicate, e.g. via the connector panel 808, to control operation of the surgical robot 4 and/or to received and display information generated by surgical robot 4 for observation by persons wearing the XR headsets 920.

Computer 822 of computer subsystem 820 includes an operating system and software to operate assigned functions of surgical robot 4. Computer 822 may receive and process information from other components (for example, tracking subsystem 830, platform subsystem 802, and/or motion control subsystem 840) in order to display information to the operator. Further, computer subsystem 820 may provide output through the speaker 826 for the operator. The speaker may be part of the surgical robot, part of an XR headset 920, or within another component of the surgical system 2. The display 824 may correspond to the display 34 shown in FIGS. 1 and 2.

Tracking subsystem 830 may include position sensor 832 and camera converter 834. Tracking subsystem 830 may correspond to the camera tracking system component 6 of FIG. 3. The DRA tracking cameras 870 operate with the position sensor 832 to determine the pose of DRAs 52. This tracking may be conducted in a manner consistent with the present disclosure including the use of infrared or visible light technology that tracks the location of active or passive elements of DRAs 52, such as LEDs or reflective fiducials (also called markers), respectively.

Functional operations of the tracking subsystem 830 and the computer subsystem 820 can be included in the computer platform 910, which can be transported by the camera tracking system component 6' of FIGS. 3A and 3B. The tracking subsystem 830 can be configured to determine the poses, e.g., location and angular orientation of the tracked DRAs. The computer platform 910 can also include a navigation controller that is configured to use the determined poses to provide navigation information to users that guides their movement of tracked tools relative to position-registered patient images and/or tracked anatomical structures during a planned surgical procedure. The computer platform 910 can display information on the display of FIGS. 3B and 3C and/or to one or more XR headsets 920. The computer platform 910, when used with a surgical robot, can be configured to communicate with the computer subsystem 820 and other subsystems of FIG. 8 to control movement of the end effector 26. For example, as will be explained below the computer platform 910 can generate a graphical representation of a patient's anatomical structure, surgical tool, user's hand, etc. with a displayed size, shape, color, and/or pose that is controlled based on the determined pose(s) of one or more the tracked DRAs, and which the graphical representation that is displayed can be dynamically modified to track changes in the determined poses over time.

Motion control subsystem 840 may be configured to physically move vertical column 16, upper arm 18, lower arm 20, or rotate end effector coupler 22. The physical movement may be conducted through the use of one or more motors 850-854. For example, motor 850 may be configured to vertically lift or lower vertical column 16. Motor 851 may be configured to laterally move upper arm 18 around a point of engagement with vertical column 16 as shown in FIG. 2. Motor 852 may be configured to laterally move lower arm 20 around a point of engagement with upper arm 18 as shown in FIG. 2. Motors 853 and 854 may be configured to move end effector coupler 22 to provide translational movement and rotation along in about three-dimensional axes. The computer platform 910 shown in FIG. 9 can provide control input to the controller 846 that guides movement of the end effector coupler 22 to position a passive end effector, which is connected thereto, with a planned pose (i.e., location and angular orientation relative to defined 3D orthogonal reference axes) relative to an anatomical structure that is to be operated on during a planned surgical procedure. Motion control subsystem 840 may be configured to measure position of the end effector coupler 22 and/or the end effector 26 using integrated position sensors (e.g. encoders).

Figure 9:
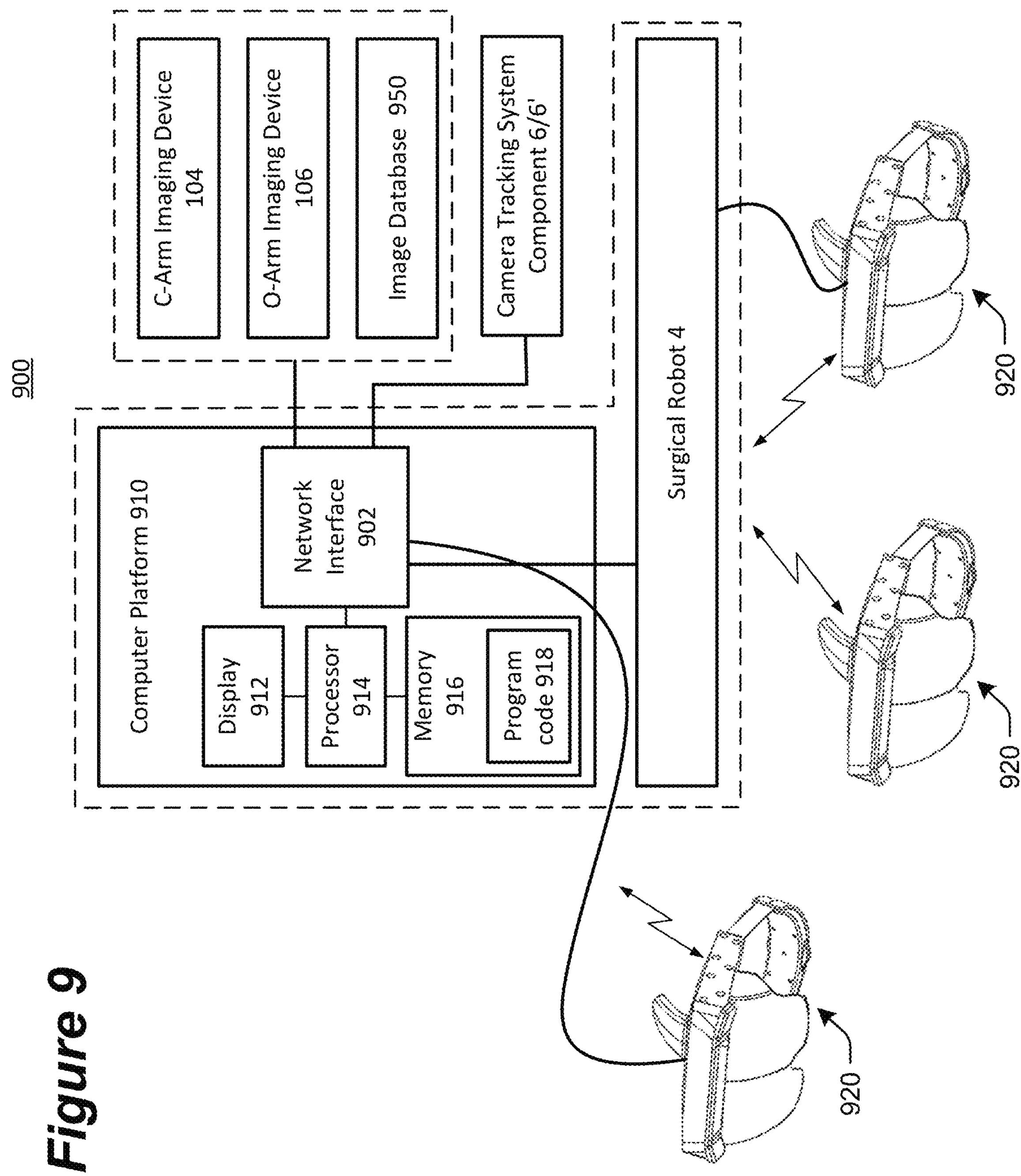
FIG. 9 illustrates a block diagram of components of a surgical system that includes imaging devices connected to a computer platform which can be operationally connected to a camera tracking system and/or surgical robot according to some embodiments of the present disclosure.

FIG. 9 illustrates a block diagram of components of a surgical system that includes imaging devices (e.g., C-Arm 104, O-Arm 106, etc.) connected to a computer platform 910 which can be operationally connected to a camera tracking system component 6 (FIG. 3A) or 6' (FIGS. 3B,3C) and/or to surgical robot 4 according to some embodiments of the present disclosure. Alternatively, at least some operations disclosed herein as being performed by the computer platform 910 may additionally or alternatively be performed by components of a surgical system.

Referring to FIG. 9, the computer platform 910 includes a display 912, at least one processor circuit 914 (also referred to as a processor for brevity), at least one memory circuit 916 (also referred to as a memory for brevity) containing computer readable program code 918, and at least one network interface 902 (also referred to as a network interface for brevity). The display 912 may be part of an XR headset 920 in accordance with some embodiments of the present disclosure. The network interface 902 can be configured to connect to a C-Arm imaging device 104 in FIG.

Figure 11:
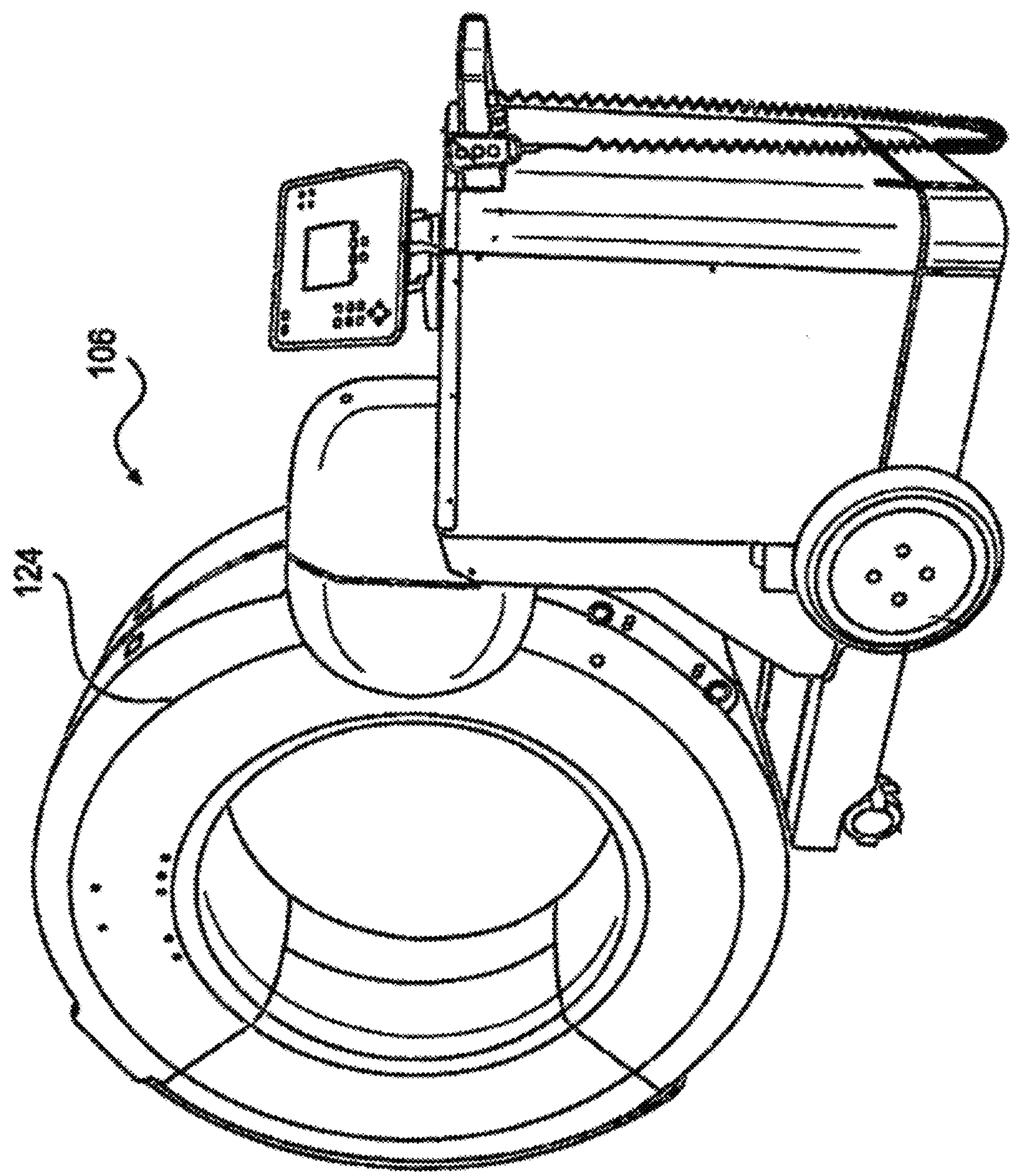
FIG. 11 illustrates an embodiment of an O-Arm imaging device that can be used in combination with the surgical robot in accordance with some embodiments of the present disclosure.

10, an O-Arm imaging device 106 in FIG. 11, another medical imaging device, an image database 950 containing patient medical images, components of the surgical robot 4, and/or other electronic equipment.

When used with a surgical robot 4, the display 912 may correspond to the display 34 of FIG. 2 and/or the tablet 890 of FIG. 8 and/or the XR headset 920 that is operatively connected to the surgical robot 4, the network interface 902 may correspond to the platform network interface 812 of FIG. 8, and the processor 914 may correspond to the computer 822 of FIG. 8. The network interface 902 of the XR headset 920 may be configured to communicate through a wired network, e.g., thin wire ethernet, and/or through wireless RF transceiver link according to one or more wireless communication protocols, e.g., WLAN, 3GPP 4G and/or 5G (New Radio) cellular communication standards, etc.

The processor 914 may include one or more data processing circuits, such as a general purpose and/or special purpose processor, e.g., microprocessor and/or digital signal processor. The processor 914 is configured to execute the computer readable program code 918 in the memory 916 to perform operations, which may include some or all of the operations described herein as being performed for surgery planning, navigated surgery, and/or robotic surgery.

The computer platform 910 can be configured to provide surgery planning functionality. The processor 914 can operate to display on the display device 912 and/or on the XR headset 920 an image of an anatomical structure, e.g., vertebra, that is received from one of the imaging devices 104 and 106 and/or from the image database 950 through the network interface 920. The processor 914 receives an operator's definition of where the anatomical structure shown in one or more images is to have a surgical procedure, e.g., screw placement, such as by the operator touch selecting locations on the display 912 for planned procedures or using a mouse-based cursor to define locations for planned procedures. When the image is displayed in the XR headset 920, the XR headset can be configured to sense in gesture-based commands formed by the wearer and/or sense voice based commands spoken by the wearer, which can be used to control selection among menu items and/or control how objects are displayed on the XR headset 920 as will be explained in further detail below.

The computer platform 910 can be configured to enable anatomy measurement, which can be particularly useful for knee surgery, like measurement of various angles determining center of hip, center of angles, natural landmarks (e.g. transepicondylar line, Whitesides line, posterior condylar line), etc. Some measurements can be automatic while some others can involve human input or assistance. The computer platform 910 may be configured to allow an operator to input a choice of the correct implant for a patient, including choice of size and alignment. The computer platform 910 may be configured to perform automatic or semi-automatic (involving human input) segmentation (image processing) for CT images or other medical images. The surgical plan for a patient may be stored in a cloud-based server, which may correspond to database 950, for retrieval by the surgical robot 4.

During orthopedic surgery, for example, a surgeon may choose which cut to make (e.g. posterior femur, proximal tibia etc.) using a computer screen (e.g. touchscreen) or extended reality (XR) interaction (e.g., hand gesture based commands and/or voice based commands) via, e.g., the XR headset 920. The computer platform 910 can generate navigation information which provides visual guidance to the surgeon for performing the surgical procedure. When used with the surgical robot 4, the computer platform 910 can provide guidance that allows the surgical robot 4 to automatically move the end effector 26 to a target pose so that the surgical tool is aligned with a target location to perform the surgical procedure on an anatomical structure.

In some embodiments, the surgical system 900 can use two DRAs to track patient anatomy position, such as one connected to patient tibia and one connected to patient femur. The system 900 may use standard navigated instruments for the registration and checks (e.g. a pointer similar to the one used in Globus ExcelsiusGPS system for spine surgery).

A particularly challenging task in navigated surgery is how to plan the position of an implant in spine, knee, and other anatomical structures where surgeons struggle to perform the task on a computer screen which is a 2D representation of the 3D anatomical structure. The system 900 could address this problem by using the XR headset 920 to display a three-dimensional (3D) computer generated representations of the anatomical structure and a candidate implant device. The computer generated representations are scaled and posed relative to each other on the display screen under guidance of the computer platform 910 and which can be manipulated by a surgeon while viewed through the XR headset 920. A surgeon may, for example, manipulate the displayed computer-generated representations of the anatomical structure, the implant, a surgical tool, etc., using hand gesture based commands and/or voice based commands that are sensed by the XR headset 920.

For example, a surgeon can view a displayed virtual handle on a virtual implant, and can manipulate (e.g., grab and move) the virtual handle to move the virtual implant to a desired pose and adjust a planned implant placement relative to a graphical representation of an anatomical structure. Afterward, during surgery, the computer platform 910 could display navigation information through the XR headset 920 that facilitates the surgeon's ability to more accurately follow the surgical plan to insert the implant and/or to perform another surgical procedure on the anatomical structure. When the surgical procedure involves bone removal, the progress of bone removal, e.g., depth of cut, can be displayed in real-time through the XR headset 920. Other features that may be displayed through the XR headset 920 can include, without limitation, gap or ligament balance along a range of joint motion, contact line on the implant along the range of joint motion, ligament tension and/or laxity through color or other graphical renderings, etc.

The computer platform 910, in some embodiments, can allow planning for use of standard surgical tools and/or implants, e.g., posterior stabilized implants and cruciate retaining implants, cemented and cementless implants, revision systems for surgeries related to, for example, total or partial knee and/or hip replacement and/or trauma.

Figure 10:
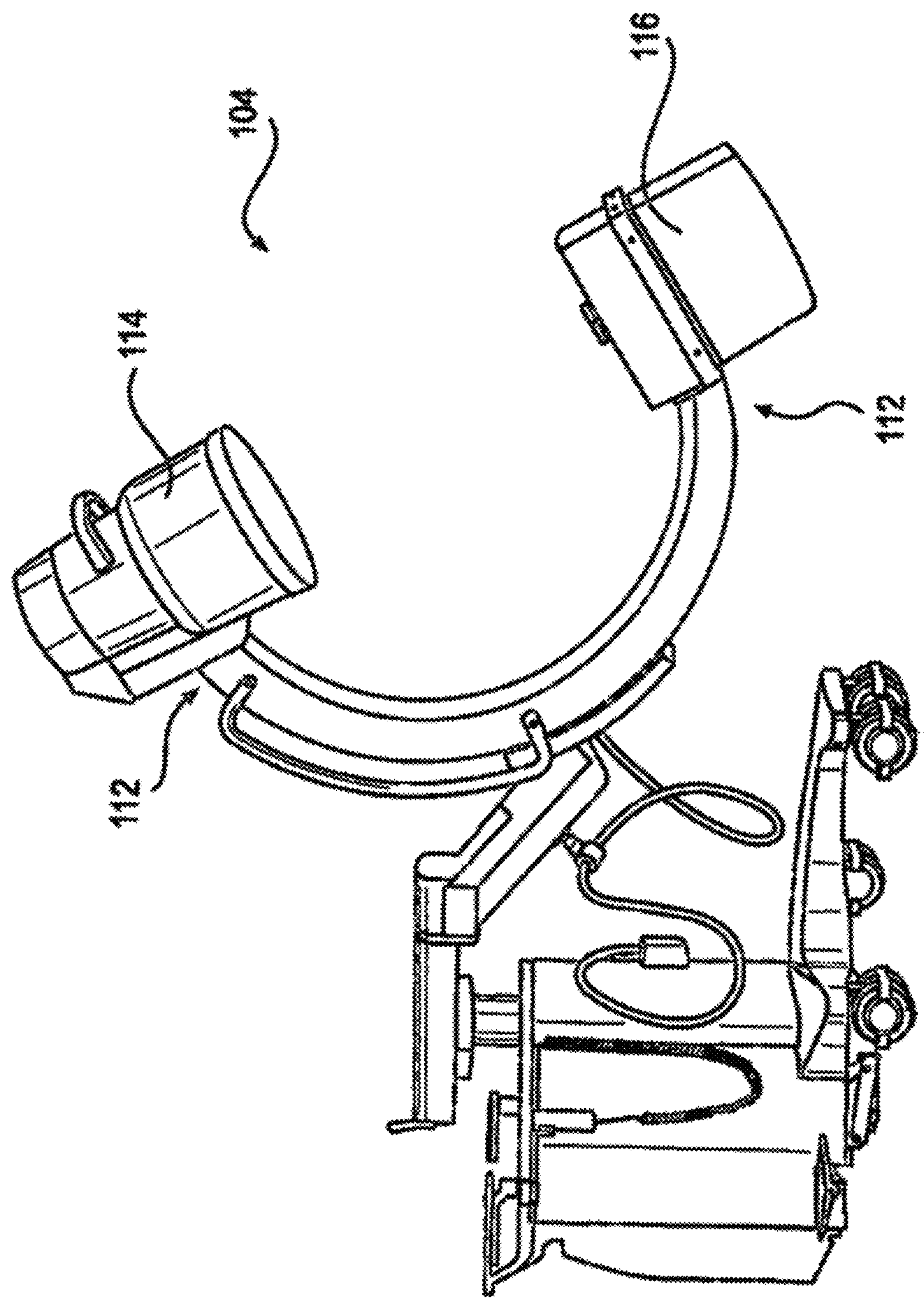
FIG. 10 illustrates an embodiment of a C-Arm imaging device that can be used in combination with the surgical robot in accordance with some embodiments of the present disclosure.

An automated imaging system can be used in conjunction with the computer platform 910 to acquire pre-operative, intra-operative, post-operative, and/or real-time image data of an anatomical structure. Example automated imaging systems are illustrated in FIGS. 10 and 11. In some embodiments, the automated imaging system is a C-arm 104 (FIG. 10) imaging device or an O-arm® 106 (FIG. 11). (O-arm® is copyrighted by Medtronic Navigation, Inc. having a place of business in Louisville, Colo., USA). It may be desirable to take x-rays of a patient from a number of different positions, without the need for frequent manual repositioning of the patient which may be required in an x-ray system. C-arm 104 x-ray diagnostic equipment may solve the problems of frequent manual repositioning and may be well known in the medical art of surgical and other interventional procedures. As illustrated in FIG. 10, a C-arm includes an elongated C-shaped member terminating in opposing distal ends 112 of the "C" shape. C-shaped member is attached to an x-ray source 114 and an image receptor 116. The space within C-arm 104 of the arm provides room for the physician to attend to the patient substantially free of interference from the x-ray support structure.

The C-arm is mounted to enable rotational movement of the arm in two degrees of freedom, (i.e. about two perpendicular axes in a spherical motion). C-arm is slidably mounted to an x-ray support structure, which allows orbiting rotational movement of the C-arm about its center of curvature, which may permit selective orientation of x-ray source 114 and image receptor 116 vertically and/or horizontally. The C-arm may also be laterally rotatable, (i.e. in a perpendicular direction relative to the orbiting direction to enable selectively adjustable positioning of x-ray source 114 and image receptor 116 relative to both the width and length of the patient). Spherically rotational aspects of the C-arm apparatus allow physicians to take x-rays of the patient at an optimal angle as determined with respect to the particular anatomical condition being imaged.

The O-arm® 106 illustrated in FIG. 11 includes a gantry housing 124 which may enclose an image capturing portion, not illustrated. The image capturing portion includes an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of the patient to be acquired from multiple directions or in multiple planes.

The O-arm® 106 with the gantry housing 124 has a central opening for positioning around an object to be imaged, a source of radiation that is rotatable around the interior of gantry housing 124, which may be adapted to project radiation from a plurality of different projection angles. A detector system is adapted to detect the radiation at each projection angle to acquire object images from multiple projection planes in a quasi-simultaneous manner. The gantry may be attached to a support structure O-arm® support structure, such as a wheeled mobile cart with wheels, in a cantilevered fashion. A positioning unit translates and/or tilts the gantry to a planned position and orientation, preferably under control of a computerized motion control system. The gantry may include a source and detector disposed opposite one another on the gantry. The source and detector may be secured to a motorized rotor, which may rotate the source and detector around the interior of the gantry in coordination with one another. The source may be pulsed at multiple positions and orientations over a partial and/or full three hundred and sixty degree rotation for multi-planar imaging of a targeted object located inside the gantry. The gantry may further comprise a rail and bearing system for guiding the rotor as it rotates, which may carry the source and detector. Both and/or either O-arm® 106 and C-arm 104 may be used as automated imaging system to scan a patient and send information to the surgical system 2.

Images captured by an imaging system can be displayed on the XR headset 920 and/or another display device of the computer platform 910, the surgical robot 4, and/or another component of the surgical system 900. The XR headset 920 may be connected to one or more of the imaging devices 104 and/or 106 and/or to the image database 950, e.g., via the computer platform 910, to display images therefrom. A user may provide control inputs through the XR headset 920, e.g., gesture and/or voice based commands, to control operation of one or more of the imaging devices 104 and/or 106 and/or the image database 950.

Figure 12:
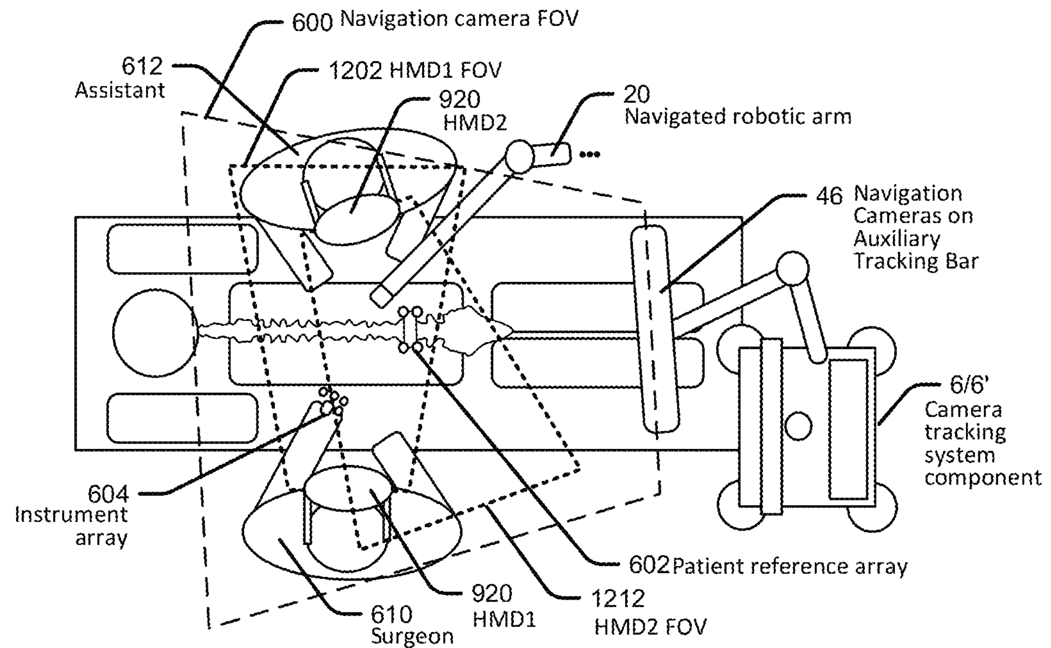
FIG. 12 illustrates a block diagram view of the components of a surgical system that includes a pair of XR headsets and an auxiliary tracking bar which operate in accordance with some embodiments of the present disclosure.
Figure 13:
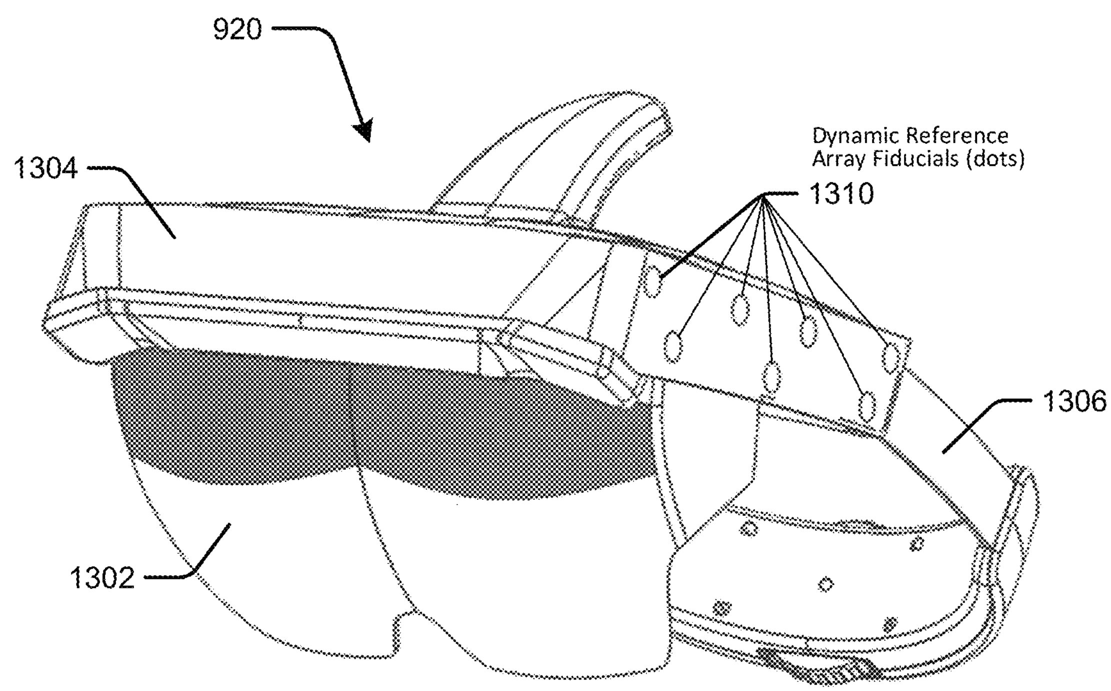
FIG. 13 illustrates an XR headset which is configured in accordance with some embodiments of the present disclosure.

FIG. 12 illustrates a block diagram view of the components of a surgical system that include a pair of XR headsets 920 (head-mounted displays HMD1 and HMD2), which may correspond to the XR headset 920 shown in FIG. 13 and operate in accordance with some embodiments of the present disclosure.

Referring to the example scenario of FIG. 12, the assistant 612 and surgeon 610 are both wearing the XR headsets 920, respectively. It is optional for the assistant 612 to wear the XR headset 920. The XR headsets 920 are configured to provide an interactive environment through which the wearers can view and interact with information related to a surgical procedure as will be described further below. This interactive XR based environment may eliminate a need for the tech personnel 614 shown in FIG. 6 to be present in the operating room and may eliminate a need for use of the display 34 shown in FIG. 6. Each XR headset 920 can include one or more cameras that are configured to provide an additional source of tracking of DRAs or other reference arrays attached to surgical tools, a patient's anatomical structure, the end effector 26, and/or other equipment. In the example of FIG. 12, XR headset 920 has a field-of-view (FOV) 1202 for tracking DRAs and other objects, XR headset 920 has a FOV 1212 partially overlapping FOV 1202 for tracking DRAs and other objects, and the tracking cameras 46 has another FOV 600 partially overlapping FOVs 1202 and 1212 for tracking DRAs and other objects.

If one or more cameras is obstructed from viewing a DRA attached to a tracked object, e.g., a surgical tool, but the DRA is in view of one or more other cameras the tracking subsystem 830 and/or navigation controller 828 can continue to track the object seamlessly without loss of navigation. Additionally, if there is partial occlusion of the DRA from the perspective of one camera, but the entire DRA is visible via multiple camera sources, the tracking inputs of the cameras can be merged to continue navigation of the DRA. One of the XR headsets and/or the tracking cameras 46 may view and track the DRA on another one of the XR headsets to enable the computer platform 910 (FIGS. 9 and 14), the tracking subsystem 830, and/or another computing component to determine the pose of the DRA relative to one or more defined coordinate systems, e.g., of the XR headsets 920, the tracking cameras 46, and/or another coordinate system defined for the patient, table, and/or room.

The XR headsets 920 can be operatively connected to view video, pictures, and/or other received information and/or to provide commands that control various equipment in the surgical room, including but not limited to neuromonitoring, microscopes, video cameras, and anesthesia systems. Data from the various equipment may be processed and displayed within the headset, for example the display of patient vitals or the microscope feed.

Example XR Headset Components and Integration to Navigated Surgery, Surgical Robots, and Other Equipment FIG. 13 illustrates an XR headset 920 which is configured in accordance with some embodiments of the present disclosure. The XR headset includes a headband 1306 configured to secure the XR headset to a wearer's head, an electronic component enclosure 1304 supported by the headband 1306, and a display screen 1302 that extends laterally across and downward from the electronic component enclosure 1304. The display screen 1302 may be a see-through LCD display device or a semi-reflective lens that reflects images projected by a display device toward the wearer's eyes. A set of DRA fiducials 1310, e.g., dots, are painted or attached in a spaced apart known arranged on one or both sides of the headset. The DRA on the headset enables the tracking cameras on the auxiliary tracking bar to track pose of the headset 920 and/or enables another XR headset to track pose of the headset 920.

The display screen 1302 operates as a see-through display screen, also referred to as a combiner, that reflects light from display panels of a display device toward the user's eyes. The display panels can be located between the electronic component enclosure and the user's head, and angled to project virtual content toward the display screen 1302 for reflection toward the user's eyes. The display screen 1302 is semi-transparent and semi-reflective allowing the user to see reflected virtual content superimposed on the user's view of a real-world scene. The display screen 1302 may have different opacity regions, such as the illustrated upper laterally band which has a higher opacity than the lower laterally band. Opacity of the display screen 1302 may be electronically controlled to regulate how much light from the real-world scene passes through to the user's eyes. A high opacity configuration of the display screen 1302 results in high-contrast virtual images overlaid on a dim view of the real-world scene. A low opacity configuration of the display screen 1302 can result in more faint virtual images overlaid on a clearer view of the real-world scene. The opacity may be controlled by applying an opaque material on a surface of the display screen 1302.

Figure 14:
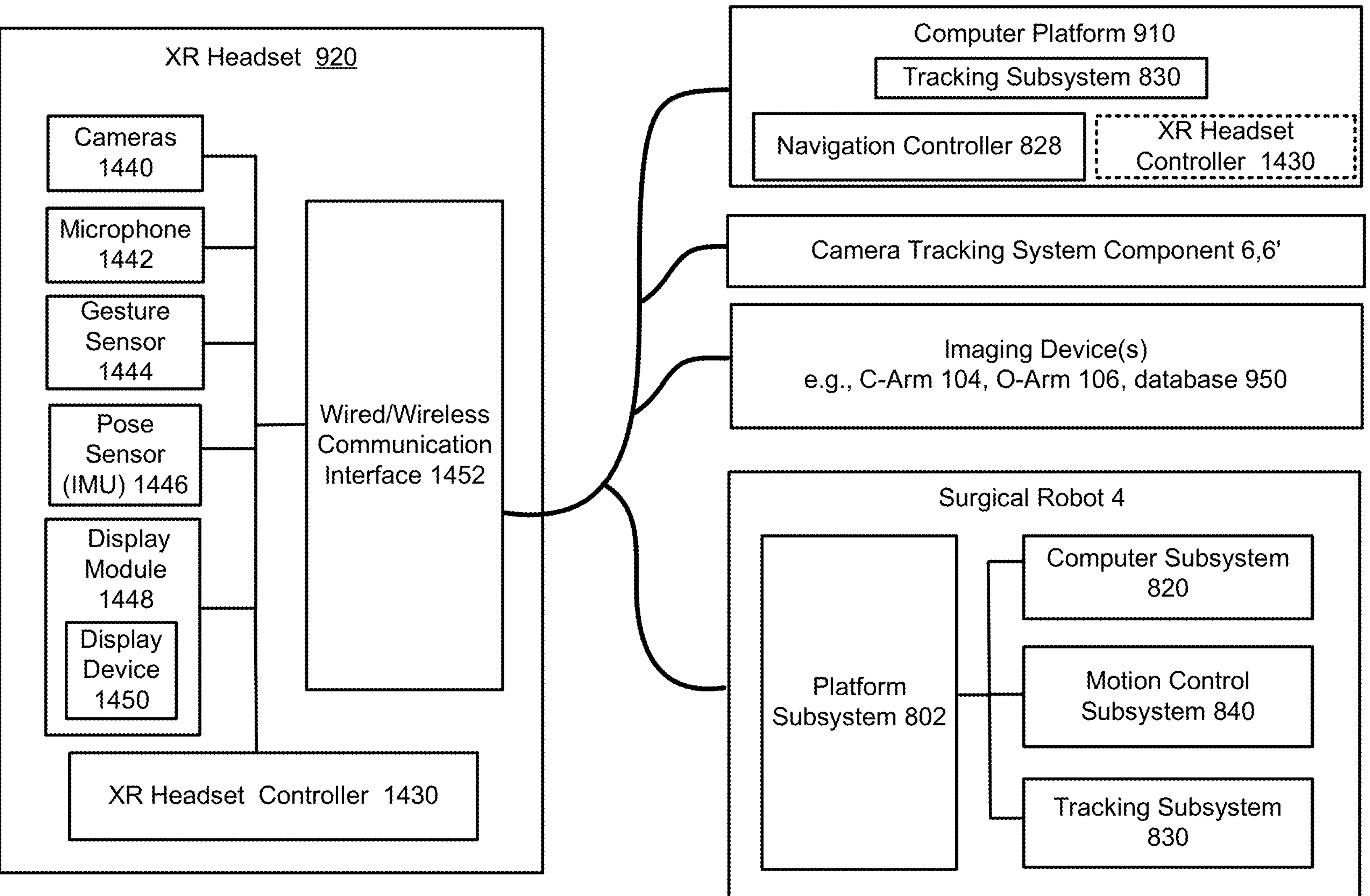
FIG. 14 illustrates electrical components of the XR headset that can be operatively connected to a computer platform, imaging device(s), and/or a surgical robot in accordance with some embodiments of the present disclosure.

According to some embodiments, the surgical system includes an XR headset 920 and an XR headset controller, e.g., controller 1430 in FIG. 14. The XR headset 920 is configured to be worn by a user during a surgical procedure and has a see-through display screen 1302 that is configured to display an XR image and to allow at least a portion of a real-world scene to pass therethrough for viewing by the user. The XR headset 920 also includes an opacity filter positioned between at least one of the user's eyes and the real-world scene when the see-through display screen 1302 is viewed by the user. The opacity filter is configured to provide opaqueness to light from the real-world scene. The XR headset controller is configured to communicate with a navigation controller, e.g., controller(s) 828A, 828B, and/or 828C in FIG. 14, to receive navigation information from the navigation controller which provides guidance to the user during the surgical procedure on an anatomical structure, and is further configured to generate the XR image based on the navigation information for display on the see-through display screen 1302.

Opacity of the display screen 1302 may be configured as a gradient having a more continuously changing opacity with distance downward from a top portion of the display screen 1302. The gradient's darkest point can be located at the top portion of the display screen 1302, and gradually becoming less opaque further down on the display screen 1302 until the opacity is transparent or not present. In an example further embodiment, the gradient can change from about 90% opacity to entirely transparent approximately at the mid-eye level of the display screen 1302. With the headset properly calibrated and positioned, the mid-eye level can correspond to the point where the user would look straight out, and the end of the gradient would be located at the "horizon" line of the eye. The darker portion of the gradient will allow crisp, clear visuals of the virtual content and help to block the intrusive brightness of the overhead operating room lights.

Using an opacity filter in this manner enables the XR headset 920 to provide virtual reality (VR) capabilities, by substantially or entirely blocking light from the real-world scene, along an upper portion of the display screen 1302 and to provide AR capabilities along a middle or lower portion of the display screen 1302. This allows the user to have the semi-translucence of AR where needed and allowing clear optics of the patient anatomy during procedures. Configuring the display screen 1302 as a gradient instead of as a more constant opacity band can enable the wearer to experience a more natural transition between a more VR type view to a more AR type view without experiencing abrupt changes in brightness of the real-world scene and depth of view that may otherwise strain the eyes such as during more rapid shifting between upward and downward views.

The display panels and display screen 1302 can be configured to provide a wide field of view see-through XR display system. In one example configuration they provide an 80° diagonal field-of-view (FOV) with 55° of vertical coverage for a user to view virtual content. Other diagonal FOV angles and vertical coverage angles can be provided through different size display panels, different curvature lens, and/or different distances and angular orientations between the display panels and curved display screen 1302.

FIG. 14 illustrates electrical components of the XR headset 920 that can be operatively connected to the computer platform 910, to one or more of the imaging devices, such as the C-arm imaging device 104, the O-arm imaging device 106, and/or the image database 950, and/or to the surgical robot 800 in accordance with various embodiments of the present disclosure.

The XR headset 920 provides an improved human interface for performing navigated surgical procedures. The XR headset 920 can be configured to provide functionalities, e.g., via the computer platform 910, that include without limitation any one or more of: identification of hand gesture based commands and/or voice based commands, display XR graphical objects on a display device 1450. The display device 1450 may be a video projector, flat panel display, etc., which projects the displayed XR graphical objects onto the display screen 1302. The user can view the XR graphical objects as an overlay anchored to particular real-world objects viewed through the display screen 1302 (FIG. 13). The XR headset 920 may additionally or alternatively be configured to display on the display screen 1450 video feeds from cameras mounted to one or more XR headsets 920 and other cameras.

Electrical components of the XR headset 920 can include a plurality of cameras 1440, a microphone 1442, a gesture sensor 1444, a pose sensor (e.g., inertial measurement unit (IMU)) 1446, a display module 1448 containing the display device 1450, and a wireless/wired communication interface 1452. As will be explained below, the cameras 1440 of the XR headset may be visible light capturing cameras, near infrared capturing cameras, or a combination of both.

The cameras 1440 may be configured operate as the gesture sensor 1444 by capturing for identification user hand gestures performed within the field of view of the camera(s) 1440. Alternatively the gesture sensor 1444 may be a proximity sensor and/or a touch sensor that senses hand gestures performed proximately to the gesture sensor 1444 and/or senses physical contact, e.g. tapping on the sensor or the enclosure 1304. The pose sensor 1446, e.g., IMU, may include a multi-axis accelerometer, a tilt sensor, and/or another sensor that can sense rotation and/or acceleration of the XR headset 920 along one or more defined coordinate axes. Some or all of these electrical components may be contained in the component enclosure 1304 or may be contained in another enclosure configured to be worn elsewhere, such as on the hip or shoulder.

As explained above, the surgical system 2 includes a camera tracking system component 6/6' and a tracking subsystem 830 which may be part of the computer platform 910. The surgical system may include imaging devices (e.g., C-arm 104, O-arm 106, and/or image database 950) and/or a surgical robot 4. The tracking subsystem 830 is configured to determine a pose of DRAs attached to an anatomical structure, an end effector, a surgical tool, etc. A navigation controller 828 is configured to determine a target pose for the surgical tool relative to an anatomical structure based on a surgical plan, e.g., from a surgical planning function performed by the computer platform 910 of FIG. 9, defining where a surgical procedure is to be performed using the surgical tool on the anatomical structure and based on a pose of the anatomical structure determined by the tracking subsystem 830. The navigation controller 828 may be further configured to generate steering information based on the target pose for the surgical tool, the pose of the anatomical structure, and the pose of the surgical tool and/or the end effector, where the steering information indicates where the surgical tool and/or the end effector of a surgical robot should be moved to perform the surgical plan. Various of the cameras 1440 of the XR headset 920 may be connected to the camera tracking system component 6/6' to track poses of DRAs, user's hand(s), etc.

The electrical components of the XR headset 920 can be operatively connected to the electrical components of the computer platform 910 through a wired/wireless interface 1452. The electrical components of the XR headset 920 may be operatively connected, e.g., through the computer platform 910 or directly connected, to various imaging devices, e.g., the C-arm imaging device 104, the I/O-arm imaging device 106, the image database 950, and/or to other medical equipment through the wired/wireless interface 1452.

The surgical system 2 further includes at least one XR headset controller 1430 (also referred to as "XR headset controller" for brevity) that may reside in the XR headset 920, the computer platform 910, and/or in another system component connected via wired cables and/or wireless communication links. Various functionality is provided by software executed by the XR headset controller 1430. The XR headset controller 1430 is configured to receive navigation information from the navigation controller 828 which provides guidance to the user during the surgical procedure on an anatomical structure, and is configured to generate an XR image based on the navigation information for display on the display device 1450 for projection on the see-through display screen 1302.

The configuration of the display device 1450 relative to the display screen (also referred to as "see-through display screen") 1302 is configured to display XR images in a manner such that when the user wearing the XR headset 920 looks through the display screen 1302 the XR images appear to be in the real world. The display screen 1302 can be positioned by the headband 1306 in front of the user's eyes.

The XR headset controller 1430 can be within a housing that is configured to be worn on a user's head or elsewhere on the user's body while viewing the display screen 1302 or may be remotely located from the user viewing the display screen 1302 while being communicatively connected to the display screen 1302. The XR headset controller 1430 can be configured to operationally process signaling from the cameras 1440, the microphone 142, and/or the pose sensor 1446, and is connected to display XR images on the display device 1450 for user viewing on the display screen 1302. Thus, the XR headset controller 1430 illustrated as a circuit block within the XR headset 920 is to be understood as being operationally connected to other illustrated components of the XR headset 920 but not necessarily residing within a common housing (e.g., the electronic component enclosure 1304 of FIG. 13) or being otherwise transportable by the user. For example, the XR headset controller 1430 may reside within the computer platform 910 which, in turn, may reside within a housing of the computer tracking system component 6' shown in FIGS. 3B and 3C.

Example XR Headset Component Optical Arrangement

Figure 15:
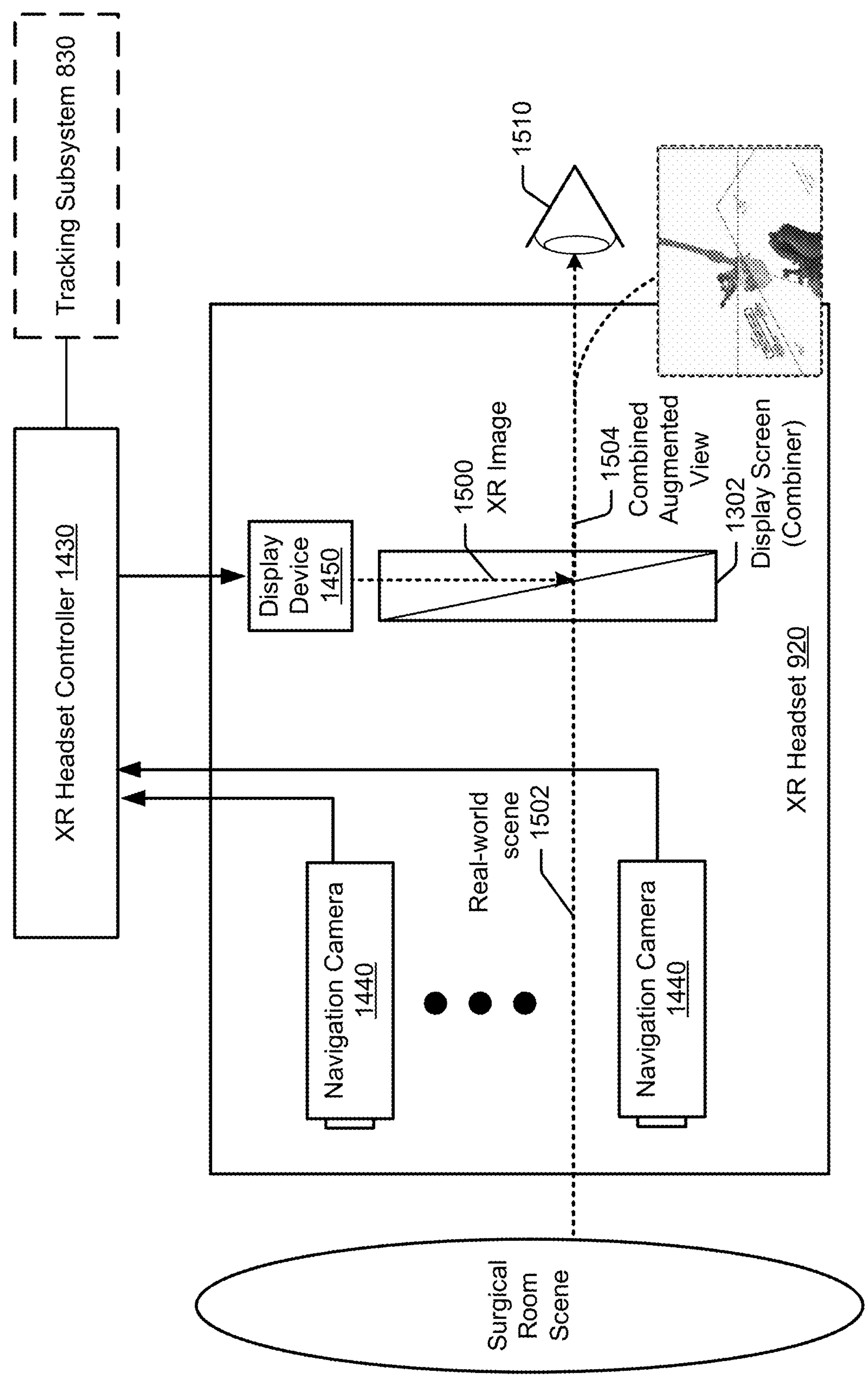
FIG. 15 illustrates a block diagram showing arrangement of optical components of the XR headset in accordance with some embodiments of the present disclosure.

FIG. 15 illustrates a block diagram showing arrange of optical components of the XR headset 920 in accordance with some embodiments of the present disclosure. Referring to FIG. 15, the display device 1450 is configured to display XR images generated by the XR headset controller 1430, light from which is projected as XR images 1500 toward the display screen 1302. The display screen 1302 is configured to combine light of the XR images 1500 and light from the real-world scene 1502 into a combined augmented view 1504 that is directed to the user's eye(s) 1510. The display screen 1302 configured in this manner operates as a see-through display screen. The XR headset 920 can include any plural number of tracking cameras 1440. The cameras 1440 may be visible light capturing cameras, near infrared capturing cameras, or a combination of both.

Example User Views Through the XR Headset

The XR headset operations can display both 2D images and 3D models on the display screen 1302. The 2D images may preferably be displayed in a more opaque band of the display screen 1302 (upper band) and the 3D model may be more preferably displayed in the more transparent band of the display screen 1302, otherwise known as the environmental region (bottom band). Below the lower band where the display screen 1302 ends the wearer has an unobstructed view of the surgical room. It is noted that where XR content is display on the display screen 1302 may be fluidic. It is possible that where the 3D content is displayed moves to the opaque band depending on the position of the headset relative to the content, and where 2D content is displayed can be placed in the transparent band and stabilized to the real world. Additionally, the entire display screen 1302 may be darkened under electronic control to convert the headset into virtual reality for surgical planning or completely transparent during the medical procedure. As explained above, the XR headset 920 and associated operations not only support navigated procedures, but also can be performed in conjunction with robotically assisted procedures.

Figure 16:
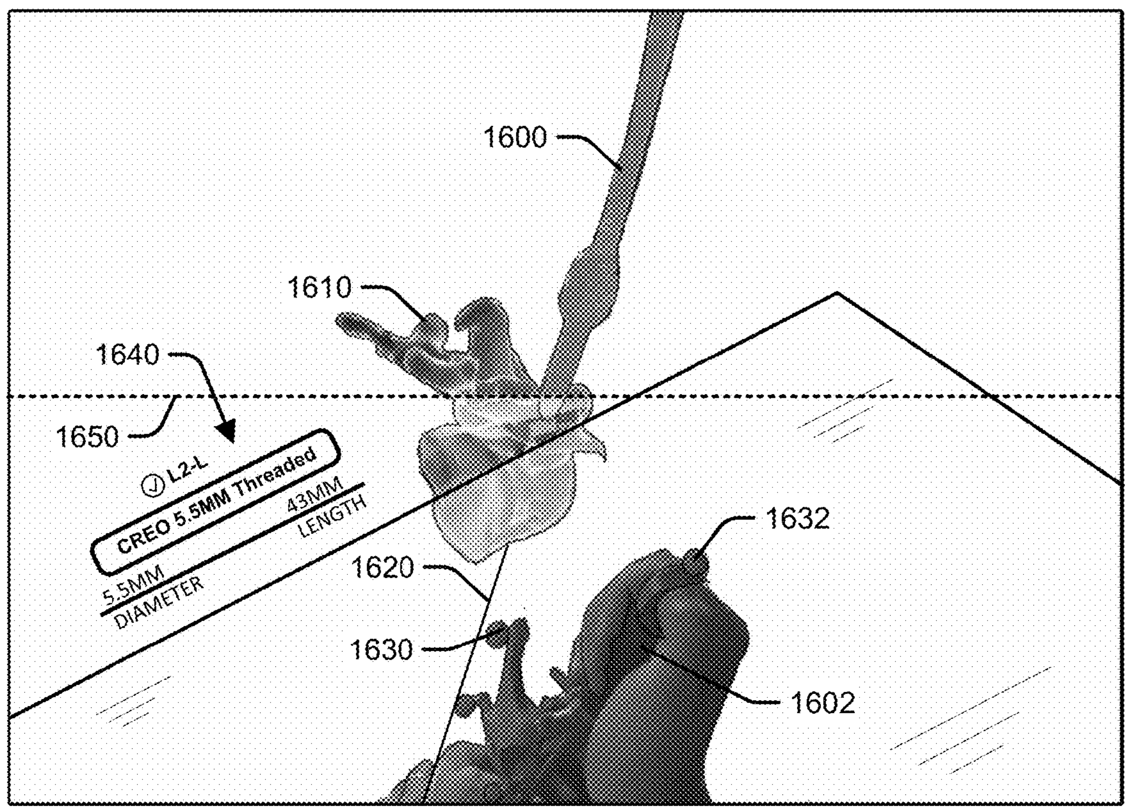
FIG. 16 illustrates an example view through the display screen of an XR headset for providing navigation assistance to manipulate a surgical tool during a medical procedure in accordance with some embodiments of the present disclosure.

FIG. 16 illustrates an example view through the display screen 1302 of the XR headset 920 for providing navigation assistance to a user who is manipulating a surgical tool 1602 during a medical procedure in accordance with some embodiments of the present disclosure. Referring to FIG. 16, when the surgical tool 1602 is brought in vicinity of a tracked anatomical structure so that dynamic reference arrays 1630 and 1632, connected to the surgical tool 1602, become within the field of view of the cameras 1440 (FIG. 15) and/or 46 (FIG. 6), a graphical representation 1600 of the tool can be displayed in 2D and/or 3D images in relation to a graphical representation 1610 of the anatomical structure. The user can use the viewed graphical representations to adjust a trajectory 1620 of the surgical tool 1602, which can be illustrated as extending from the graphical representation 2000 of the tool through the graphical representation 1610 of the anatomical structure. The XR headset 920 may also display textual information and other objects 1640. The dashed line 1650 extending across the viewed display screen represents an example division between different opacity level upper and lower bands.

Other types of XR images (virtual content) that can be displayed on the display screen 1302 can include, but are not limited to any one or more of:

I) 2D Axial, Sagittal and/or Coronal views of patient anatomy;

2) overlay of planned vs currently tracked tool and surgical implant locations;

3) gallery of preoperative images;

4) video feeds from microscopes and other similar systems or remote video conferencing;

5) options and configuration settings and buttons;

6) floating 3D models of patient anatomy with surgical planning information;

7) real-time tracking of surgical instruments relative to floating patient anatomy;

8) augmented overlay of patient anatomy with instructions and guidance; and 9) augmented overlay of surgical equipment.

Example Configuration of Cameras for Tracking System Component

Figure 17:
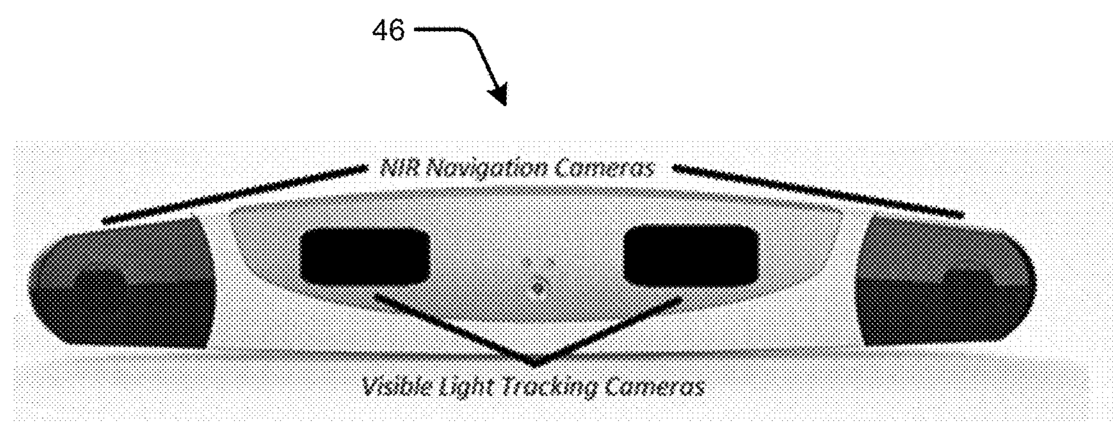
FIG. 17 illustrates an example configuration of an auxiliary tracking bar having two pairs of stereo cameras configured in accordance with some embodiments of the present disclosure.

FIG. 17 illustrates example configuration of an auxiliary tracking bar 46 having two pairs of stereo tracking cameras configured in accordance with some embodiments of the present disclosure. The auxiliary tracking bar 46 is part of the camera tracking system component of FIGS. 3A, 3B, and 3C. The stereo tracking cameras include a stereo pair of spaced apart visible light capturing cameras and another stereo pair of spaced apart near infrared capturing cameras, in accordance with one embodiment. Alternatively, only one stereo pair of visible light capturing cameras or only one stereo pair of near infrared capture cameras can used in the auxiliary tracking bar 46. Any plural number of near infrared and/or visible light cameras can be used.

Pose Measurement Chaining

As explained above, navigated surgery can include computer vision tracking and determination of pose (e.g., position and orientation in a six degree-of-freedom coordinate system) of surgical instruments, such as by determining pose of attached DRAs that include spaced apart fiducials, e.g., disks or spheres, arranged in a manner known to the camera tracking system. The computer vision uses spaced apart tracking cameras, e.g., stereo cameras, that are configured to capture near infrared and/or visible light. In this scenario, there are three parameters jointly competing for optimization: (1) accuracy, (2) robustness, and (3) user ergonomics during a surgical procedure.

Computer operations may combine (chain) measured poses in ways that can improve optimization of one or more of the above three parameters by incorporating additional tracking cameras mounted to one or more XR headsets. As shown in FIG. 17, a stereo pair of visible light tracking cameras and another stereo pair of near infrared tracking cameras can be attached to the auxiliary tracking bar of the camera tracking system component in accordance with some embodiments of the present disclosure. Operational algorithms are disclosed that analyze the pose of DRAs that are fully observed or partially observed (e.g., when less than all of the fiducials of a DRA are viewed by a pair of stereo cameras), and combine the observed poses or partial poses in ways that can improve accuracy, robustness, and/or ergonomics during navigated surgery.

As explained above, the XR headset may be configured to augment a real-world scene with computer generated XR images. The XR headset may be configured to provide an XR viewing environment by displaying the computer generated XR images on a see-through display screen that allows light from the real-world scene to pass therethrough for combined viewing by the user. Alternatively, the XR headset may be configured to provide a VR viewing environment by preventing or substantially preventing light from the real-world scene from being directly viewed by the user along the viewing path of the displayed XR images. An XR headset can be configured to provide both AR and VR viewing environments. In one embodiment, both AR and VR viewing environments are provided by lateral bands of substantially differing opacity arranged between the see-through display screen and the real-world scene, so that a VR viewing environment is provided for XR images aligned with a high opacity band and an AR viewing environment is provided for XR images aligned with the low opacity band. In another embodiment, both AR and VR viewing environments are provided by computer adjustable control of an opacity filter that variably constrains how much light from the real-world scene passes through a see-through display screen for combining with the XR images viewed by the user. Thus, the XR headset can also be referred to as an AR headset or a VR headset.

As was also explained above, the XR headset can include near infrared tracking cameras and/or visible light tracking cameras that are configured to track fiducials of DRAs connected to surgical instruments, patient anatomy, other XR headset(s), and/or a robotic end effector. Using near infrared tracking and/or visible light tracking on the XR headset provides additional tracking volume coverage beyond what cameras on a single auxiliary tracking bar can provide. Adding near infrared tracking cameras to the existing auxiliary tracking bar allows for the headset location to be tracked more robustly but less accurately than in visible light. Mechanically calibrating the visible and near infrared tracking coordinate systems enables the coordinate systems to be aligned sufficiently to perform 3D DRA fiducials triangulation operations using stereo matching to jointly identify pose of the DRA fiducials between the visible and near infrared tracking coordinate systems. Using both visible and near infrared tracking coordinate systems can enable any one or more of: (a) identifying tools that would not be identified using a single coordinate system; (b) increased pose tracking accuracy; (c) enabling a wider range of motion without losing tracking of surgical instruments, patient anatomy, and/or a robotic end effector; and (d) naturally track an XR headset in the same coordinate system as the navigated surgical instruments.

Figure 18:
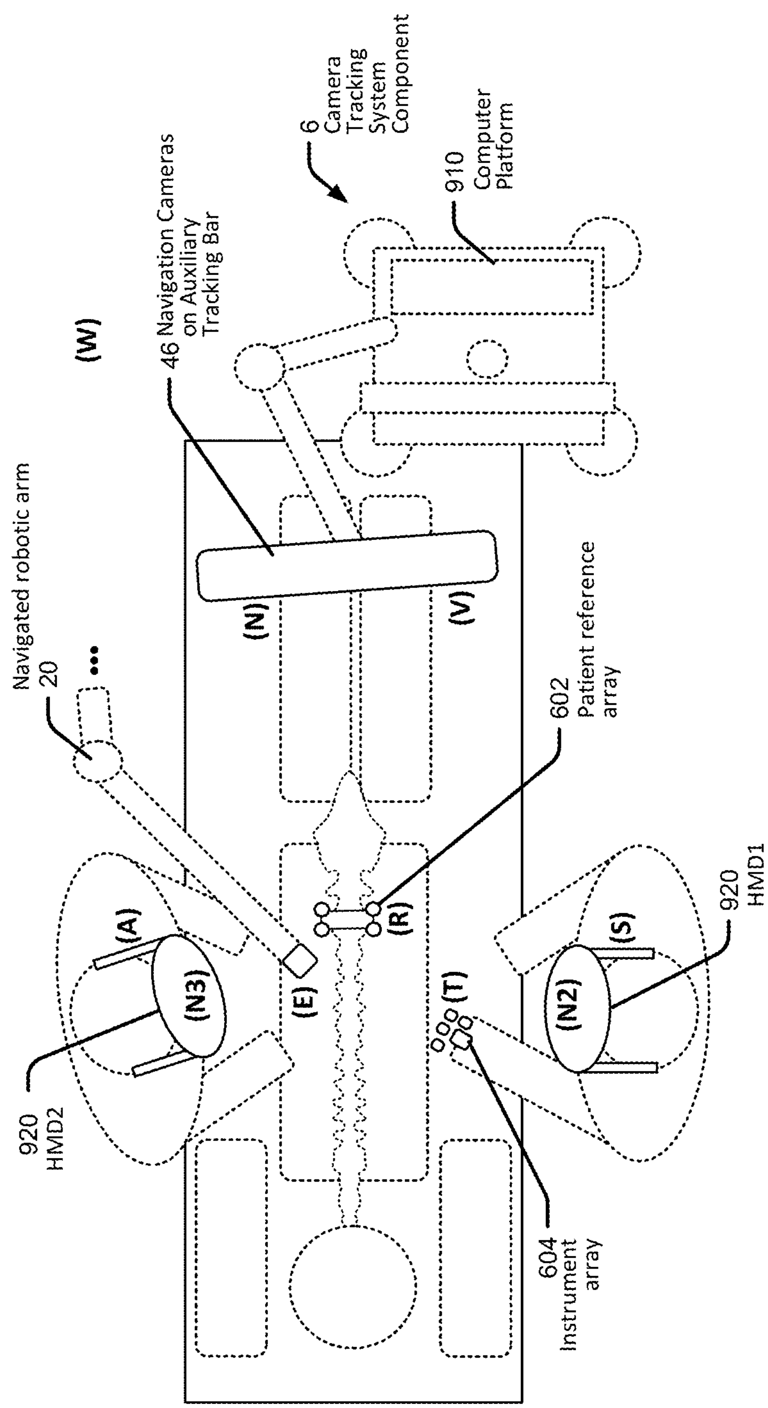
FIG. 18 illustrates a block diagram view of the components of a surgical system that includes tracking cameras in a pair of XR headsets and in an auxiliary tracking bar which collectively operate in accordance with some embodiments of the present disclosure.

FIG. 18 illustrates a block diagram view of the components of a surgical system that include tracking cameras in a pair of XR headsets 920 (head-mounted displays HMD1 and HMD2) and tracking cameras in a camera tracking bar in the camera tracking system component 6' which houses the computer platform 910. The computer platform 910 can include the tracking subsystem 830, the navigation controller 828, and the XR headset controller 1430 as was earlier shown in FIG. 14.

Referring to the surgical system of FIG. 18, a surgeon and an assistant are both wearing XR headsets HMD1 920 and HMD2 920, respectively, each if which includes tracking cameras that may be configured as shown in FIG. 13. It is optional for the assistant to wear the XR headset HMD2 920.

The combination of XR headsets HMD1 920 and HMD2 920 and the tracking cameras 46 on the auxiliary tracking bar can, in operation with the computer platform 910, more robustly track the example objects of a patient reference array (R), robotic end effector (E), and surgical tool (T) or instrument. The overlapping views from different perspectives that are provided by the XR headsets HMD1 920 and HMD2 920 and the tracking cameras 46 on the auxiliary tracking bar are shown in FIG. 12.

Each of the items labeled in FIG. 18 represent a unique coordinate system. Descriptions of the coordinate system labels are as follows:

- A=visible light coordinate system of second headset HMD2 920;
- N3=near infra-red (NIR) coordinate system of second headset HMD2 920;
- S=visible light coordinate system of primary headset HMD1 920;
- N2=NIR coordinate system of the primary headset HMD1 920;
- N=NIR coordinate system of the auxiliary navigation bar 46;
- V=visible light coordinate system of the auxiliary navigation bar 46;
- R=NIR coordinate system of a patient reference fiducial array 602;
- T=NIR coordinate system of a tracked tool 604;
- E=NIR coordinate system of a tracked robot end effector on robotic arm 20; and
- W=Inertially navigated world coordinate system with stable gravity vector.

The spatial relationships of some of these labeled objects (and by extension, coordinate systems) can be measured and calibrated during the manufacturing process, when the equipment is installed in an operating room, and/or before a surgical procedure is to be performed. In the disclosed system, the following coordinate systems are calibrated: $T_{N2}^{S}$; $T_{N3}^{A}$; $T_{N}^{V}$, where the term "T" is defined as a six degree-of-freedom (6 DOF) homogeneous transformation between the two indicated coordinates systems. Thus, for example, the term $T_{N2}^{S}$ is a 6 DOF homogeneous transformation between the visible light coordinate system of the primary headset HMD1 920 and the NIR coordinate system of the primary headset HMD1 920.

In one embodiment, the XR headsets HMD1 920 and HMD2 920 have passive visible light fiducials painted or otherwise attached to them (coordinate systems S and A), such as the reference array fiducials 1310 shown in FIG. 13. The tracking cameras are spatially calibrated to these passive fiducials (coordinate systems N2 and N3).

As explained above, the cameras on the XR headset HMD1 920 and HMD2 920 and the tracking cameras 46 on the auxiliary tracking bar have partially overlapping field of views. If one or more of the cameras on the XR headset HMD1 920 are obstructed from viewing a DRA attached to a tracked object, e.g., a tracked tool (T), but the DRA is in view of the cameras of the other XR headset HMD2 920 and/or the tracking cameras 46 on the auxiliary tracking bar, the computer platform 910 can continue to track the DRA seamlessly without loss of navigation. Additionally, if there is partial occlusion of the DRA from the perspective of the cameras on the XR headset HMD1 920, but the entire DRA is visible via cameras of the other XR headset HMD2 920 and/or the tracking cameras 46 on the auxiliary tracking bar, the tracking inputs of the cameras can be merged to continue navigation of the DRA.

More particularly, the various coordinate systems can be chained together by virtue of independent observations the various camera systems provided by the XR headsets HMD1 920 and HMD2 920 and the tracking cameras 46 on the auxiliary tracking bar. For example, each of the XR headsets HMD1 920 and HMD2 920 may require virtual augmentation of the robotic end effector (E). While one XR headset HMD1 920 (N2) and the tracking cameras 46 on the auxiliary tracking bar (N) are able to see (E), perhaps the other XR headset HMD2 920 (N3) cannot. The location of (E) with respect to (N3) can still be computed via one of several different operational methods. Operations according to one embodiment performing chaining of poses from a patient reference (R). If the patient reference (R) is seen by (N3) and either one of (N) or (N2), the pose of (E) with respect to (N3) can be solved directly by either one of the following two equations:

$$T_{N3}^{E}=T_{N2}^{E}T_{R}^{N2}T_{N3}^{R}\text{—or—}T_{N3}^{E}=T_{N}^{E}T_{R}^{N}T_{N3}^{R}$$

They key to this pose chaining is that the relationship between the frames at the end of each chain are inferred (circled and transported below). The chains can be arbitrarily long and are enabled by having more than one stereo camera system (e.g., N, N2, N3).

The camera tracking system can be configured to receive tracking information related to tracked objects from a first tracking camera (e.g., N3) and a second tracking camera (e.g., N2) during a surgical procedure. The camera tracking system can determine a first pose transform (e.g., $T_{N3}^{R}$) between a first object (e.g., R) coordinate system and the first tracking camera (e.g., N3) coordinate system based on first object tracking information from the first tracking camera (e.g., N3) which indicates pose of the first object (e.g., R). The camera tracking system can determine a second pose transform (e.g., $T_{R}^{N2}$) between the first object (e.g., R) coordinate system and the second tracking camera (e.g., N2) coordinate system based on first object tracking information from the second tracking camera (e.g., N2) which indicates pose of the first object (e.g., R). The camera tracking system can determine a third pose transform (e.g., $T_{N2}^{E}$) between a second object (e.g., E) coordinate system and the second tracking camera (e.g., N2) coordinate system based on second object tracking information from the second tracking camera (e.g., N2) which indicates pose of the second object (e.g., E). The camera tracking system can determine a fourth pose transform (e.g., $T_{N3}^{E}$) between the second object (e.g., E) coordinate system and the first tracking camera (e.g., N3) coordinate system based on combining the first, second, and third pose transforms.

In some further embodiments, the camera system can further determine pose of the second object (e.g., E) and the first tracking camera system (e.g., N3) coordinate system based on processing the tracking information through the fourth pose transform.

Because of the overlapping field of views of the various camera systems, the camera tracking system is capable of determining the pose of the second object (e.g., E) relative to first tracking camera (e.g., N3) when the first camera is blocked from seeing the second object (e.g., E). For example, in some embodiments the camera tracking system is further configured to determine the fourth pose transform (e.g., $T_{N3}^{E}$) between the second object (e.g., E) coordinate system and the first tracking camera (e.g., N3) coordinate system without use of any tracking information from the first tracking camera (e.g., N3) indicating pose of the second object (e.g., E).

The camera tracking system may achieve higher tracking accuracy by merging synchronized imagery from multiple camera systems. For example, the camera tracking system can determine pose of the second object (e.g., E) relative to first tracking camera (e.g., N3) by merging synchronized imagery of the second object (e.g., E) from multiple perspectives (first and second tracking cameras), and can use weighting which can be determined based on accuracy specs of the respective cameras. More particularly, the camera tracking system can be further configured to determine the fourth pose transform (e.g., $T_{N3}^{E}$) between the second object (e.g., E) coordinate system and the first tracking camera (e.g., N3) coordinate system based on second object tracking information from the first tracking camera (e.g., N3) which indicates pose of the second object (e.g., E) and further based on a result of the combining of the first, second, and third pose transforms.

The surgical system may be configured to display on the see-through display screen of an XR headset an XR image having a pose that is determined based on the fourth pose transform. The camera tracking system may be further configured to generate the XR image as a graphical representation of the second object (e.g., E) that is posed on the see-through display screen based on processing through the fourth pose transform the first object tracking information from the first and second tracking cameras and the second object tracking information from the second tracking camera.

As explained above, the camera tracking system can include a navigation controller 828 communicatively connected to the first tracking camera (e.g., N3) and the second tracking camera (e.g., N2) to receive the tracking information and configured to perform the determination of the first, second, third, and fourth pose transforms.

Registration of Surgical Tool Characteristics to a Reference Array Identified by Camera Tracking System During a surgical procedure, the camera tracking system can simultaneously track the poses of surgical tools which are being held or supported within the field-of-view of a set of tracking cameras, and can resume tracking of a surgical tool when it is moved from outside to inside that field-of-view, e.g., after being picked-up again. Many surgical tools require software configuration to track properly. Because the camera tracking system tracks poses of the reference arrays attached to or on the surgical tools, the camera tracking system should be informed of which surgical tool characteristics are registered to which of the tracked reference arrays. The navigation controller 828 (FIG. 14) can thereby operate with knowledge of the particular characteristics of the surgical tool. For example, registration of surgical tool characteristics of the distance from an identified reference array to a tip of the surgical tool enables the navigation controller 828 to navigate a surgeon's movement of the tool tip during a surgical procedure. Similarly, registration of a direction of curvature of a surgical tool relative to an identified reference array enables the navigation controller 828 to display an accurate graphical representation of the surgical tool through the XR headset 920 and accurately posed relative to a tracked anatomical structure during the surgical procedure.

The registration process is also referred to as a pairing process during which a user holds a surgical tool having a reference array in the field-of-view of the set of tracking cameras for identification of the reference array, and the user then define characteristics of that surgical tool, in accordance with some embodiments. The registration process is repeated for each combination of reference array and surgical tool characteristics that will be tracked during a surgical procedure, and can be further repeated when a reference array is detached from one type of surgical tool and attached to a different type of surgical tool. It can be important to enable a surgeon or other medical personnel wearing an XR headset to be able to time efficiently perform registration processes for a set of surgical tools, to assist the surgeon with avoiding making errors when registering surgical tool characteristics with reference arrays, and to reduce interruption of a surgeon's concentration before and during a surgical procedure.

Some further embodiments of the present disclosure are directed to using an XR headset during a registration process to register an identified reference array to characteristics of a surgical tool, and to display a representation of those characteristics through the XR headset so that a user can verify correctness of the registration. Using the XR headset during the registration process can provide a more intuitive, time efficient and reliable process for surgeons and other medical personnel (users) to register surgical tools with a camera tracking system before and/or during a surgical procedure.

The registration process may be automatically initiated responsive to a reference array being brought into the field-of-view of a set of tracking cameras and the camera tracking system determining that the identified reference array has not yet been registered as being paired with characteristics of a surgical tool.

In an embodiment, an XR headset includes a set of tracking cameras which may, for example, be contained in the electronic component enclosure 1304 of the XR headset 920 as shown in FIG. 13. The camera tracking system (e.g., system 6 in FIG. 18) identifies a reference array (e.g., physical reference array 1800 in FIGS. 21-22) which is tracked by the set of tracking cameras, such as by identifying reference array in video streams from the tracking cameras. The reference arrays can be uniquely identified based on the differing orientations between the sets of fiducials forming respective reference arrays. The camera tracking system determines whether the identified reference array is registered as being paired with characteristics of one of a plurality of surgical tools defined in a surgical tool database. Based on the reference array being determined to not be registered and based on receiving user input, the camera tracking system registers the reference array as being paired with characteristics of the surgical tool which is selected among the plurality of surgical tools based on the user input. The camera tracking system then provides a representation of the characteristics to a display device of the XR headset 920 for display to the user.

Thus, a user can initiate registration by raising the surgical tool into the field-of-view of the set of tracking cameras attached to the XR headset 920. When an unregistered reference array comes into the field-of-view of the tracking cameras, the camera tracking system can cause a visual prompt to be displayed through the XR headset 920 which prompts the user to perform registration of the reference array to characteristics of the associated surgical tool. The camera tracking system receives video from the tracking cameras, identifies the reference array based on the spacing and relative, and determines that the identified reference array has not yet been registered as being paired with any defined characteristics of a surgical tool defined in the surgical tool database. The camera tracking system receives user input identifying characteristics of the surgical tool, and registers the reference array as being paired with characteristics of the surgical tool.

Example surgical tool characteristics can include, without limitation, structural and/or operational characteristics of a drill, saw, screw driver, retractor, and implant such as a screw, spacer, interbody fusion device, plate, rod, etc.

Example Configuration of "Three Camera" Tracking for Tracking System Component If five or more three-dimensional (3D) points on an object can be identified, a single camera may be all that is needed to solve for the six degree-of-freedom (6DOF) position and orientation of the object relative to the camera. If two cameras are well calibrated together, the 6DOF pose can be solved for using only three 3D points via stereo triangulation. According to various embodiments of the present disclosure, a third camera is introduced and situated between but spaced apart from a line extending through the stereo camera pair. This third camera improves the accuracy by providing a third off-axis perspective of a 2D or 3D tracked object, edge, or point.

With two or more cameras, poses of objects such as surgical instruments or robotic end effectors are solved by correlating and triangulating features on the tracked objects to a database of feature locations. Accuracy is therefore a function of:

a. how accurately features are localized in 2D images;
b. how spread out the features of a tracked object are in 3D space;
c. how spread out and numerous the tracking cameras are; and
d. how well the cameras have been calibrated.

Adding a third camera reduces the errors in (a.) due to simple averaging of noise while directly impacting errors due to (c.). The third camera may also act as a verification of calibration accuracy of the other two cameras. If a stereo pair is out of calibration in heading and/or yaw, for example, the tracked object will appear well triangulated but be off in depth. This calibration error is directly observable with the addition of a third camera. Finally, by placing the third camera slightly above the other two and optionally angling it down, when all the cameras are visible light cameras, the third camera gains a new perspective on 3D geometry of objects not previously observable when using NIR cameras.

FIG. 20*a* illustrates a single point stereo camera triangulation using two tracking cameras (2010 and 2012). FIG. 20*b* illustrates a single point triangulation using three tracking cameras (2020, 2022, and 2024) in accordance with some embodiments of the present disclosure.

FIG. 19 illustrates an example configuration of a camera bar 1900 (e.g., auxiliary tracking bar of camera tracking system component 6/6' of FIGS. 6 and 18 or part of the XR headset 920) having three stereo tracking cameras configured in accordance with some embodiments of the present disclosure. The camera bar 1900 may be a part of the camera tracking system, and the camera tracking system may be within the camera tracking system component 6/6', may be at least partially in navigation controller 828, or may be within the XR headset 920. In this embodiment, the three tracking cameras may be visible light cameras and/or the tracking cameras may be configured for near infrared (NIR) light sensing.

The first and second tracking cameras (1910 and 1920) may be attached at spaced apart locations on the camera bar 1900. Centers of the first and second tracking cameras are spaced apart by a distance D1. The third tracking camera 1930 may be attached at a location on the camera bar 1900 that is between locations of the first and second tracking cameras (1910 and 1920) and spaced apart a distance D2 from a line 1940 extending through the centers of the first and second tracking cameras (1910 and 1920).

The distance D2 the third tracking camera 1930 is spaced apart from the line 1940 may be between one-quarter and one-half a distance D1 between the centers of the first and second tracking cameras (1910 and 1920). Additionally, the third tracking camera 1930 may be the same distance from the first tracking camera 1910 as the third tracking camera 1930 is from the second tracking camera 1920. The three tracking cameras may all be pointed downward and be angled such that the tracking cameras views converge towards a single point that is within a distance range for which the tracking cameras are configured to track objects, such as the anticipated furthest and closest distance between objects being tracked in a surgical environment and the location of the tracking cameras.

In this embodiment, the use of visible light cameras and high contrast tracked objects, which may be used in FIGS. 21-25, provides an alternative to NIR solutions (a) disk-based objects with geometrically encoded identification and (b) edge dominated objects with QR or barcode style identification.

Figure 21:
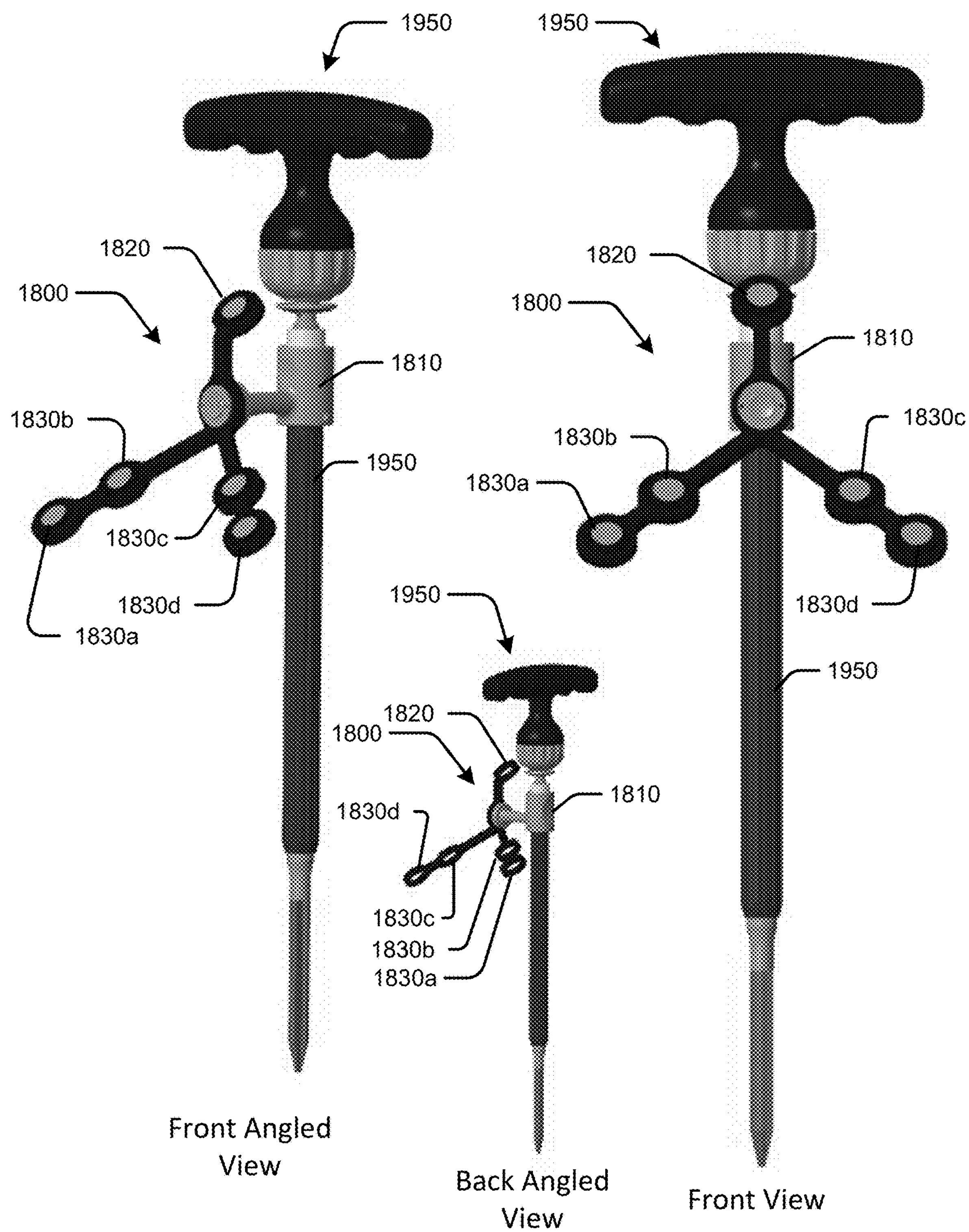
FIG. 21 illustrates examples of a surgical tool attached to a physical reference array with fiducial disks, in accordance with some embodiments of the present disclosure.
Figure 22:
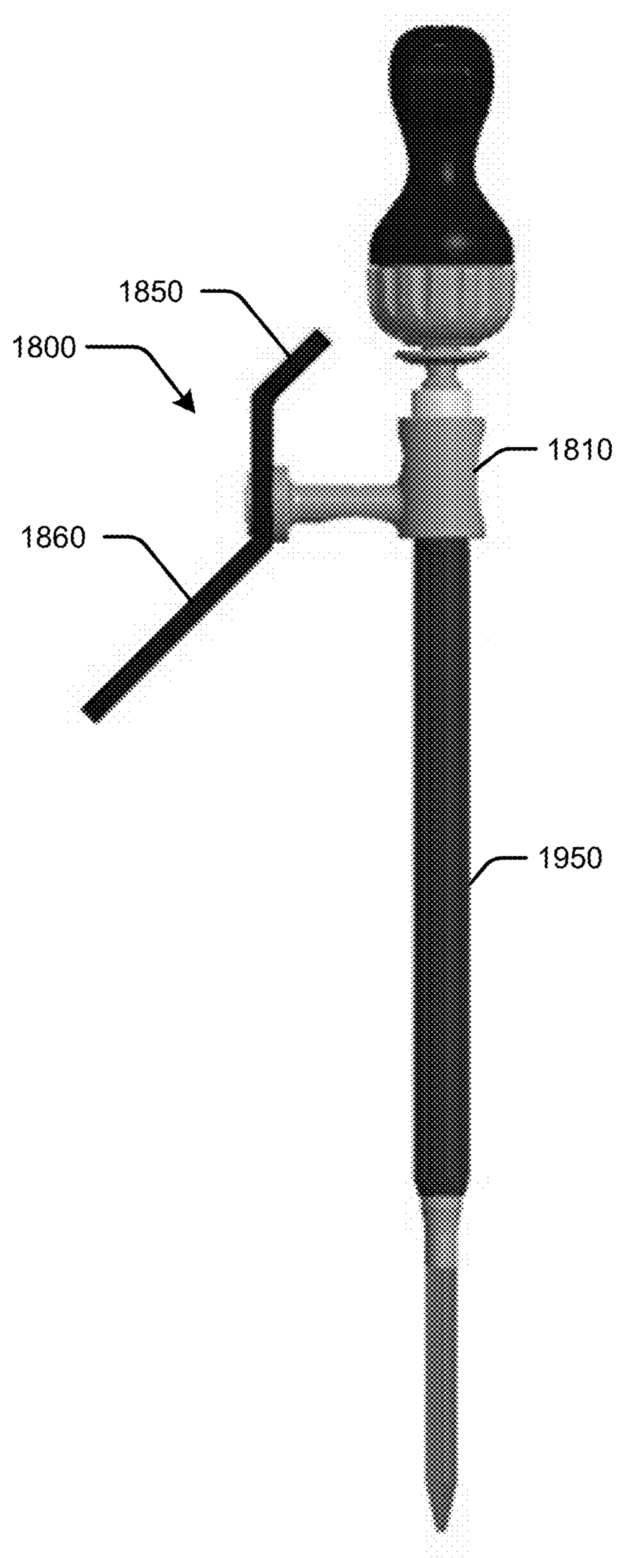
FIG. 22 Illustrates an example side view of the physical reference array attached to the surgical tool of FIG. 21, in accordance with some embodiments of the present disclosure.

FIGS. 21-22 illustrate a surgical tool 1950 attached to a physical reference array 1800 including fiducial disks arranged in two parallel planes, each containing positions for at least one passive fiducial disk. The array of passive fiducial disks can be simultaneously tracked by the multiple cameras at different angles. The arrangement of passive fiducial disks enables them to be visible to the tracking cameras even at steep trajectories.

FIG. 21 depicts different viewing angles of the surgical tool 1950 attached to an example physical reference array 1800 with five fiducial disks 1820 and 1830*a*-*d*. In FIG. 21, the fiducial disk 1820 is in a first plane that is parallel to and spaced apart from a plane that includes fiducial disks 1830*a*-*d*. In this example, fiducial disks 1820, 1830*a*, 1830*d* can be referred to as outer disks and their location may remain the same across numerous physical reference arrays. Fiducial disks 1830*b*, 1830*c* are inner disks and their position along their respective arms of the physical reference array may be different between different physical reference arrays and the difference may be detected to uniquely identify the physical reference array. Each physical reference array includes a coupling element 1810 for attaching to a surgical tool 1950 (e.g., a surgical tool). The tracking system can detect a unique pattern of the fiducial disks 1820, 1830*a*-*d*, recognize the specific physical reference array, and therefore, determine the location of the surgical tool 1950. Since the object identities are encoded in the 3D geometric distances between the fiducial disks, changing the relative locations of the two inner disks 1830*b* and 1830*c* relative to the rest of the array creates a different pattern and therefore changes the unique object identifier.

From the back angled view in FIG. 21, it can be seen that the fiducial disks may be detectable from a back view of the physical reference array 1800. This allows for the surgical tool 1950 to be detected, identified, and tracked while the physical reference array 1800 is not facing, or is not angled directly, toward a camera. Thus, doctors may use the instruments (e.g., surgical tool 1950) with greater freedom without having to adjust the instrument, or use the instrument, in a manner allowing for the physical reference array 1800 to be facing toward the tracking cameras.

In some embodiments, the disks must be at least 4 mm from center to center of adjacent disks to be detected as different disks and to be encoded as a unique pattern within the tracking software. These unique patterns will allow for tracking of multiple instruments at one time.

Using 5 disks can provide redundancy as observed when comparing FIGS. 21-22. For example, in FIG. 22, fiducial disk 1830*b* is obstructed by 1820, however, the distance between fiducial disk 1830*c* and fiducial disk 1830*d* can be used to identify the physical reference array. While only three disks are needed for pose recovery, four disks are required to uniquely identify an object. This allows for any one disk to be covered or obstructed without any loss of functionality.

These fiducial disks can either be inserted, painted, or laser etched onto the array. Since the arrays may not require sensitive electronics or retro-reflective beads, the array can be easily autoclaved.

In an additional or alternative embodiments, a different number of fiducial disks can be used. In some examples, a physical reference array may use only four fiducial disks and double the number of unique patterns that are available. A single inner fiducial disk can be used instead of two inner fiducial disks (e.g., fiducial disks 1830*b-c*) and the position of the single inner fiducial disk can be adjusted to be any position along either arm of the physical reference array.

In some embodiments, each of the disks are consistent in shape and size, where the outer 3 disks locations remain constant between patterns. In additional or alternative embodiments, the size, shape and location of the disk markers may be adjusted as long as the physical reference array includes at least two parallel planes that each include at least one fiducial disk.

In some embodiments, the disks are either retro-reflective or colored for visible light tracking. The disks may be replaceable, for example, using a snap-in/push-out method from the back or the array face or a threaded feature. The disks may be designed for visible light tracking and may also be machine washable. With visible light tracking, contrast can be important, so the disks may be replaced once their contrast has dissipated due to use and washing.

In some embodiments, parallel planes allow for tracking from multiple angles (e.g., top-down and side) depending on surgical field setup, which can reduce a risk of occlusion and loss of navigation. In additional or alternative embodiments, fiducial disks used in the tracking array can be designed for visible light and may be machine washable for multiple-case use. In additional or alternative embodiments, physical reference arrays can allow for optimized accuracy while allowing the surgical site to be visible from surgeon's point of view.

In some embodiments, a physical reference array can use any shape fiducials. For example, the physical reference array can include two or more parallel planes that each include at least one spherical fiducial. In additional or alternative embodiments, a number of fiducials used in the physical reference array can be predetermined to allow for either greater redundancy or a greater number of unique patterns to act as unique identifiers.

FIG. 22 illustrates a side view of the physical reference array 1800 attached to the surgical tool 1950. In this view, the fiducial disks are not viewable because they are on edge. The first plane 1850 containing fiducial disk 1820 is parallel to a second plane 1860 containing fiducial disks 1830*a-d*, and the first and second planes are spaced apart in a direction orthogonal to the planes.

Figure 26:
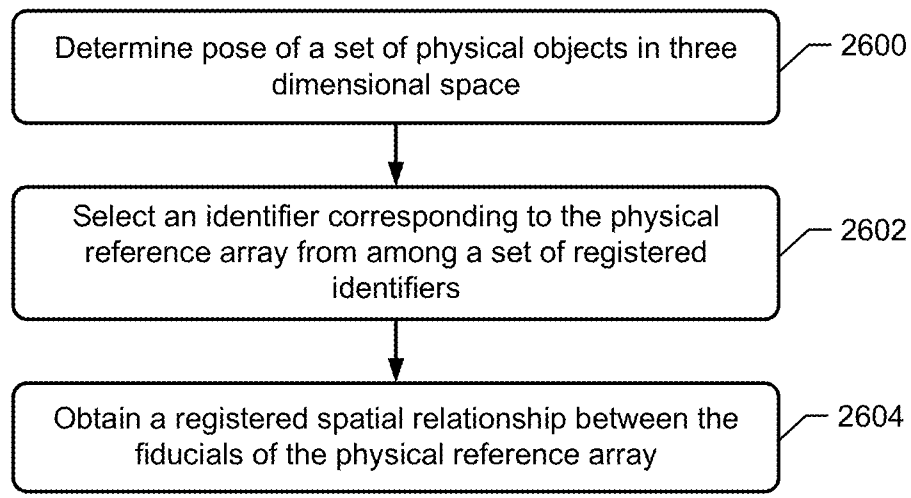
FIG. 26 illustrates a flowchart of operations performed by the camera tracking system, in accordance with some embodiments of the present disclosure.

FIG. 26 illustrates an example of processes performed by the camera tracking system, including the camera bar 1900 and tracking cameras (1910/1920/1930), in accordance with some embodiments. The camera tracking system, which includes camera bar 1900, may further include at least one processor operative to perform the processes of FIG. 26. The at least one processor may, at block 2600, determine pose of a set of physical objects in three dimensional space based on triangulating locations of the objects imaged in video streams from the first, second, and third tracking cameras (e.g., 1910/1920/1930) to locations of the first, second, and third tracking cameras spaced apart in the three dimensional space. The set of physical objects may be a physical reference array (e.g., physical reference array 1800) of spaced apart fiducials (e.g., fiducial disks 1820 and 1830*a-d*). Example operations for determining a pose are described above.

At block 2602, the at least one processor of the camera tracking system, may be further operative to select an identifier corresponding to the physical reference array from among a set of registered identifiers corresponding to a set of registered reference arrays defined in a database. The selection, of block 2602, may be based on correlating similarity of a pattern of distances between the fiducials of the physical reference array imaged in the video streams to a pattern of distances between the fiducials in one of the registered reference arrays defined in the databased and selecting the identifier corresponding to the one of the registered reference arrays.

The database, referenced here and below, may be stored in the camera tracking system, or the camera tracking system may be in communication with the database (e.g., database 950) through one or more networks (e.g., database stored in distributed cloud resources), such that the camera tracking system may be able to receive the registered reference array information necessary to perform these steps in the process.

At block 2604, the at least one processor may be further operative to obtain from the database a registered spatial relationship between the fiducials of the physical reference array based on the identifier that is selected (in block 2602), and determine the pose of the physical reference array (e.g., 1800) based on the registered spatial relationship and triangulation of locations of the fiducials (e.g., 1820 and 1830*a-d*) of the physical reference array imaged in the video streams from the first, second, and third tracking cameras to the locations of the first, second, and third tracking cameras spaced apart in the three dimensional space.

Figure 27:
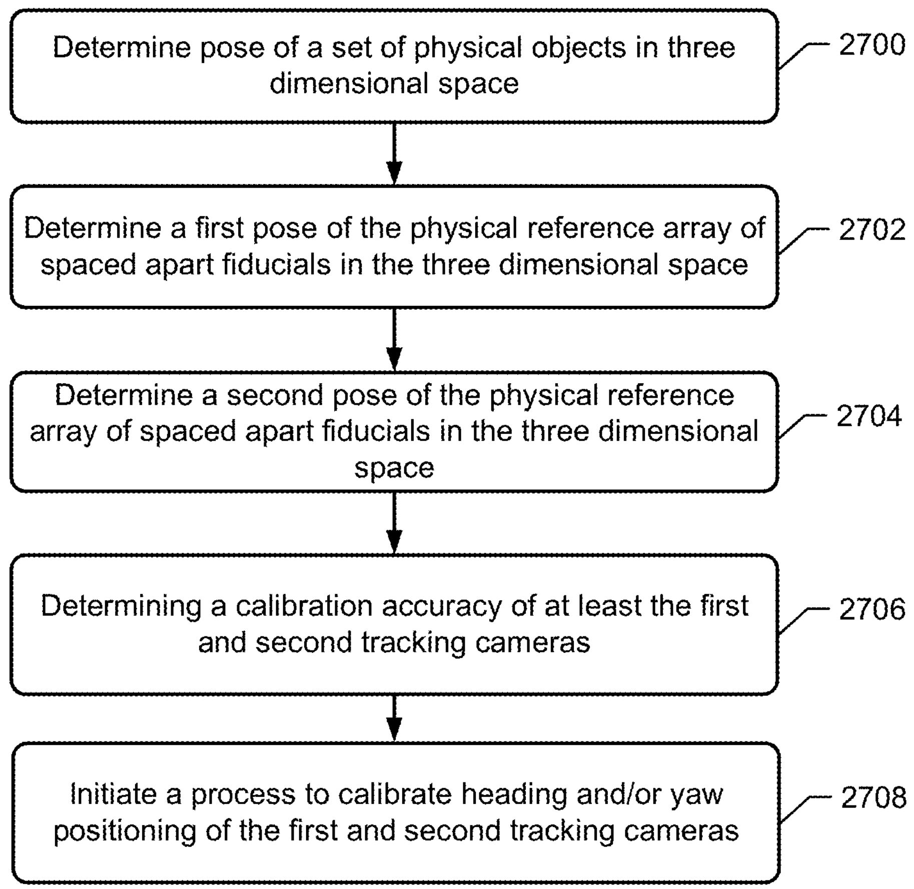
FIG. 27 illustrates another flowchart of operations performed by the camera tracking system, in accordance with some embodiments of the present disclosure.

FIG. 27 illustrates an additional or alternative example of processes performed by the camera tracking system, including the camera bar 1900 and tracking cameras (1910/1920/1930), in accordance with some embodiments.

The camera tracking system, which includes camera bar 1900, may further include at least one processor operative to perform the processes of FIG. 27. The at least one processor may, at block 2700, determine pose of a set of physical objects in three dimensional space based on triangulating locations of the objects imaged in video streams from the first, second, and third tracking cameras (e.g., 1910/1920/1930) to locations of the first, second, and third tracking cameras spaced apart in the three dimensional space. The set of physical objects may be a physical reference array (e.g., physical reference array 1800) of spaced apart fiducials (e.g., fiducial disks 1820 and 1830*a-d*).

Block 2700 may be performed in the same or similar manner as block 2600 above.

At block 2702, the at least one processor may be further operative to determine a first pose of the physical reference array of spaced apart fiducials in the three dimensional space based on triangulating locations of the fiducials imaged in the video streams from the first and second tracking cameras to locations of the first and second tracking cameras spaced apart in the three dimensional space.

At block 2704, the at least one processor may be further operative to determine a second pose of the physical reference array of spaced apart fiducials in the three dimensional space based on triangulating locations of the fiducials imaged in the video streams from the first and third tracking cameras to locations of the first and third tracking cameras spaced apart in the three dimensional space.

At block 2706, the at least one processor may be further operative to determining a calibration accuracy of at least the first and second tracking cameras based on comparison of the first and second poses.

During manufacturing, shipping, or implementation the tracking cameras may be inadvertently moved or adjusted. The calibration accuracy may indicate a level of precision or accuracy that the tracking cameras have. That is, how precise are the tracking cameras heading, yaw positioning, and/or spacing between the tracking cameras in 3D space.

At block 2708, the at least one processor may be further operative to initiate a process to calibrate heading and/or yaw positioning of the first and second tracking cameras responsive to the calibration accuracy not satisfying a defined rule. The defined rule may correspond to when the calibration accuracy is less than a defined threshold, which may indicate that one or more of the cameras have experienced excessive movement.

In one embodiment, the camera tracking system can make adjustments or indicate necessary adjustments that would correct/improve the calibration accuracy of the first and second tracking cameras.

Figure 28:
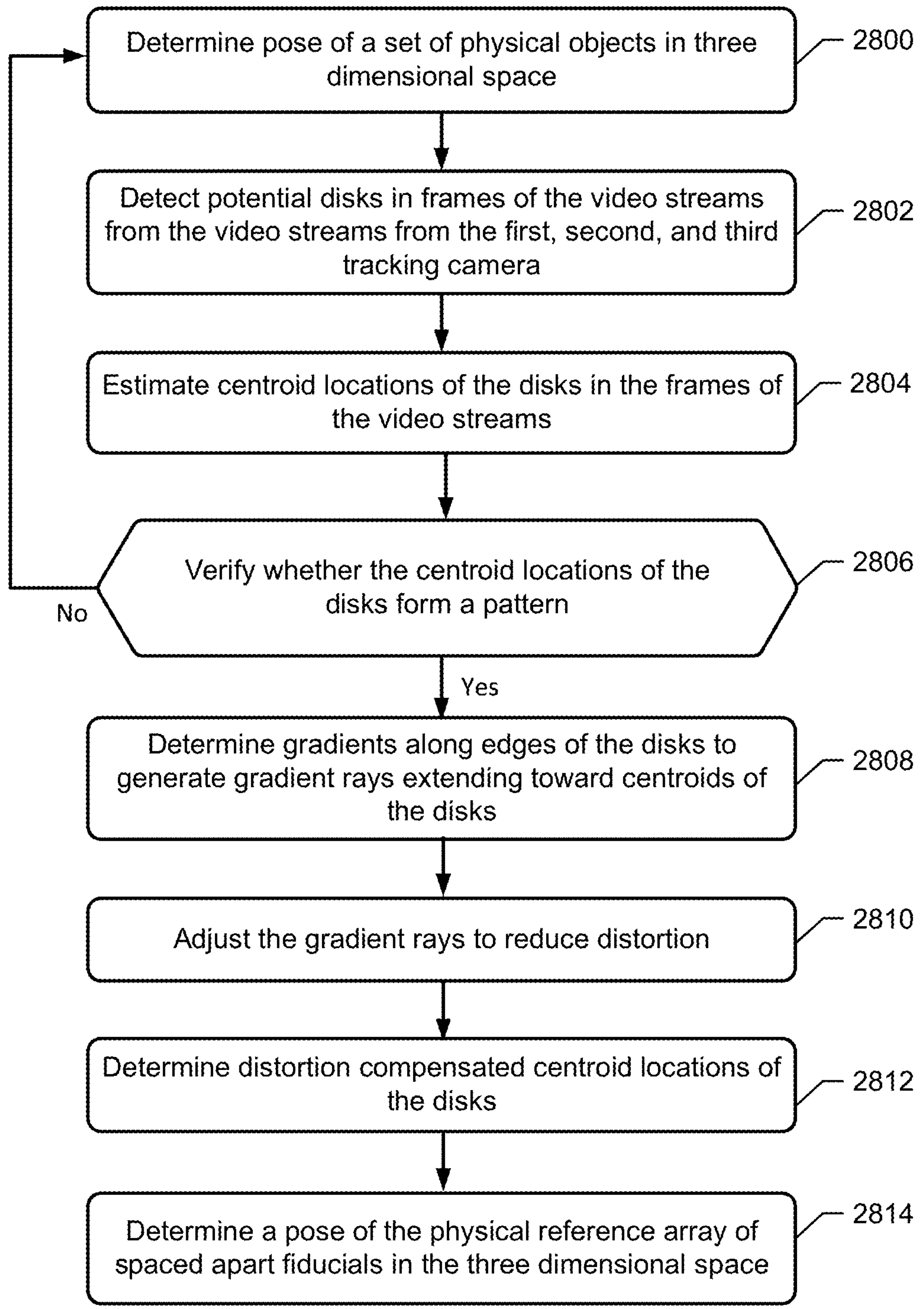
FIG. 28 illustrates another flowchart of operations performed by the camera tracking system, in accordance with some embodiments of the present disclosure.

FIG. 28 illustrates an additional or alternative example of processes performed by the camera tracking system, including the camera bar 1900 and tracking cameras (1910/1920/1930), in accordance with some embodiments.

The camera tracking system, which includes camera bar 1900, may further include at least one processor operative to perform the processes of FIG. 28. The at least one processor may, at block 2800, determine pose of a set of physical objects in three dimensional space based on triangulating locations of the objects imaged in video streams from the first, second, and third tracking cameras (e.g., 1910/1920/1930) to locations of the first, second, and third tracking cameras spaced apart in the three dimensional space. The set of physical objects may be a physical reference array (e.g., physical reference array 1800) of spaced apart fiducials (e.g., fiducials disks 1820 and 1830*a-d*).

Block 2800 may be performed in the same or similar manner as block 2600 above.

At block 2802, the at least one processor may be further operative to detect potential disks (e.g., fiducial disks 1820 and 1830*a-d*) in frames of the video streams from the video streams from the first, second, and third tracking cameras.

For example, in the instance of FIGS. 21-22, the process of block 2802 may be accomplished by taking the frames of the video streams, increasing the contrast of the frames, and having the computer tracking system search for fiducials such as fiducial disks 1820 and 1830*a-d*. By increasing the contrast of the frames, the computer tracking system may be able to more easily detect the black fiducial disks 1820 and 1830*a-d* on the physical reference array 1800. Optionally, the computer tracking system may additionally or alternatively invert the contrast in the frames, such that the computer tracking system looks for white disks that correspond to the fiducial disks 1820 and 1830*a-d.*

At block 2804, the at least one processor may be further operative to estimate centroid locations of the disks in the frames of the video streams.

At block 2806, the at least one processor may be further operative to verify whether the centroid locations of the disks form a pattern which corresponds to a pattern of disks of a registered reference array in a database.

In one embodiment, the computer tracking system compares the pattern formed by the centroid locations of the disks to a pattern of a registered reference array in a database. If a pattern of a registered reference array matches the pattern formed by the centroid locations of the disks, then the estimated centroid locations and the pattern those estimated locations form are verified.

Optionally, if the at least one processor is unable to verify at block 2806, then the process may go back to block 2800. However, if the at least one processor is able to verify at block 2806, then the process may continue to block 2808.

At block 2808, the at least one processor may be further operative to determine gradients along edges of the disks to generate gradient rays extending toward centroids of the disks. As stated above, the determination at block 2808 may be responsive to successful verification of the disks in block 2806.

In one embodiment, the gradient rays are rays that are generated to be orthogonal to tangents at spaced apart locations around the edge of a disk. Once a number of gradient rays are generated for a disk, the gradient rays may be determined to converge at a point, and this point may be determined to be the centroid of the disk.

At block 2810, the at least one processor may be further operative to adjust the gradient rays to reduce distortion based on defined intrinsic parameters of lenses of the first, second, and third tracking cameras, and output distortion compensated gradient rays.

The defined intrinsic parameters of the lenses of the tracking cameras may include the focal length of the lenses; the optical center (principal point) of the tracking camera; the lens distortion produced by each lens; the skew coefficient, which defines the angle between the x and y pixel axes; and/or the pixel coordinates.

At block 2812, the at least one processor may be further operative to perform a dual conic ellipse fitting on the distortion compensated gradient rays to determine distortion compensated centroid locations of the disks. The compensated centroid location of each disk may correspond to where the distortion compensated gradient rays for the disk converge.

At block 2814, the at least one processor may be further operative to determine a pose of the physical reference array of spaced apart fiducials in the three dimensional space. This determination, of block 2814, may be based on triangulating locations of the distortion compensated centroid locations of the disks in the video streams from the first, second, and third tracking cameras to locations of the first, second, and third tracking cameras spaced apart in the three dimensional space.

Figure 23:
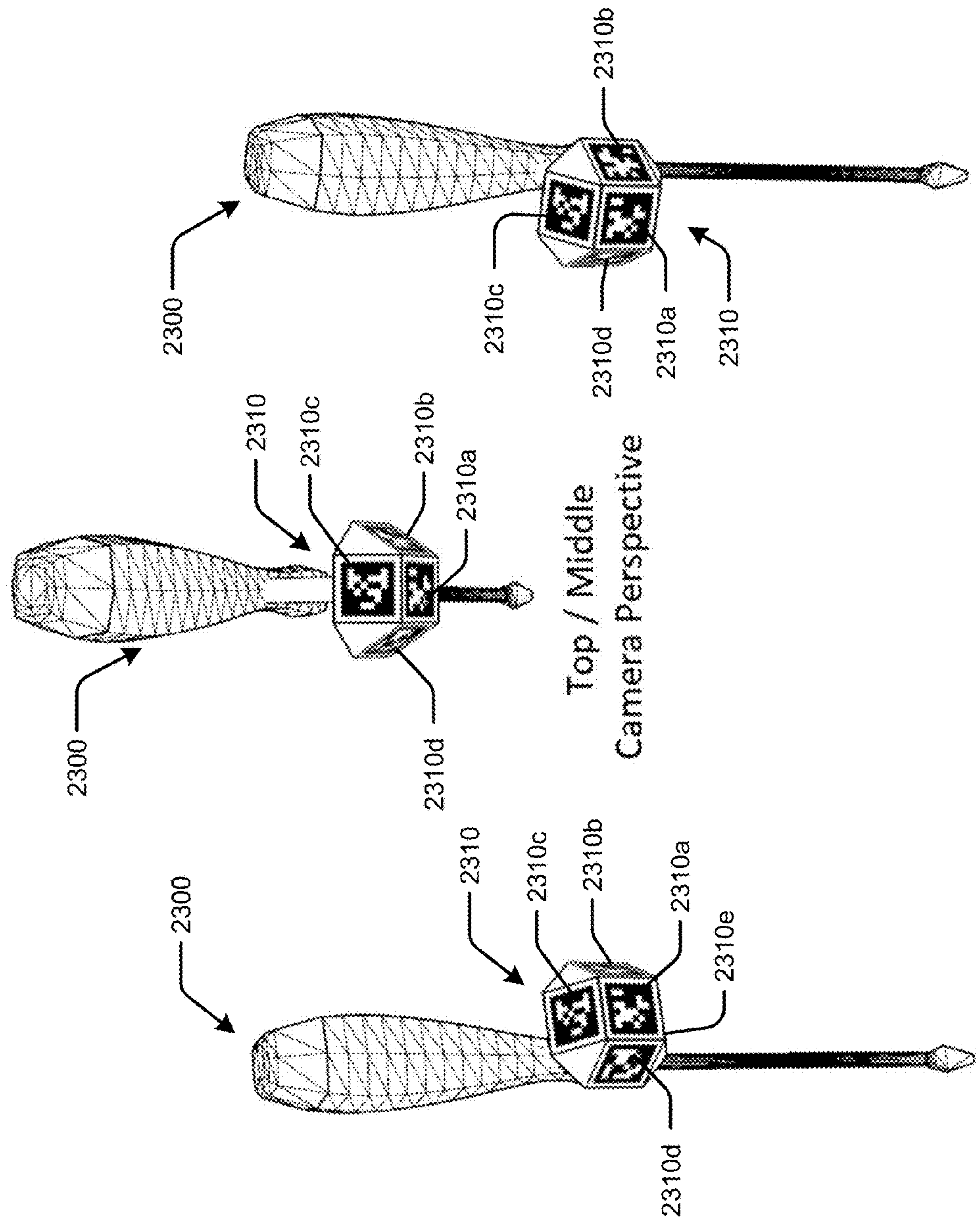
FIG. 23 illustrates an example of a surgical tool tracking array that includes a multi-faced reference array, in accordance with some embodiments of the present disclosure.

FIG. 23 illustrates an example of a surgical tool tracking array that includes a multi-faced reference array 2310. The surgical tool tracking array may include a tool holder that couples a portion of a surgical tool 2300 to the surgical tool tracking array. The multi-faced reference array 2310 may have a plurality of planar faces 2310*a-e*. The planar faces may include a front square planar face (e.g., 2310*a*) which may be configured to face away from the surgical tool 2300 when coupled to the tool holder. The planar faces may also include a plurality of side square planar faces each extending from different side edges of the front square planar face and angled toward the surgical tool when coupled to the tool holder. For example, in FIG. 23, the multi-faced reference array 2310 includes four side square planar faces 2310*b-e* each extending from different ones of the four side edges of the front square planar face 2310*a* and angled toward the surgical tool when coupled to the tool holder.

The planar faces 2310*a-e* may each include a same or different optically coded pattern. The optically coded patterns may include barcode patterns which optically encode planar face identifiers. The barcode patterns have the ability to encode a large number of potential identities by supporting an array of up to 6×6 black and white regions, each representing bits of information. The resulting 2^36 bits of information provides 6.8719E10 potential identification codes. This also allows for two bits of error correction and dividing by five faces per multi-faced reference array still allows for thousands of unique identification codes. The inclusion of multiple faces also allows for object recognition and identification from larger off-axis perspectives than a physical reference array (e.g., 1800) and the arrays are smaller and less obstructive.

While five planar faces are illustrated in this example, any number of planar faces may be used, and may be configured in any arrangement. Additionally, the planar faces may be other shapes other than a square and have optically coded patterns within the shape. For example, the planar faces may be a rectangle, triangle, oval, circle, etc.

Figure 24:
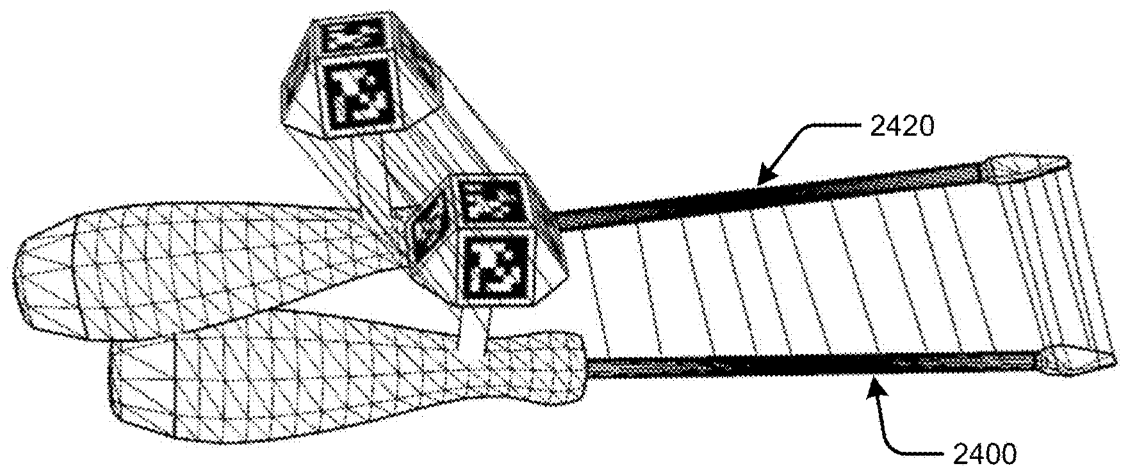
FIG. 24 illustrates an example of 2D image registration between undistorted image information and synthetic image information generated from the 3D model of the tool, in accordance with some embodiments of the present disclosure.

FIG. 24 illustrates an example of 2D image registration between undistorted image information and synthetic image information generated from the 3D model 2420 of a surgical tool. Once the object is reliably identified, a 3D model of the entire object (i.e., tools, robot end effectors, or other item types) can be loaded. The 3D model 2420 may be projected onto the 2D image plane 2400 of all tracking cameras in a location determined by fiducial pose recovery. Edges, corners and other prominent model features are then compared to the live undistorted camera image data and the model pose is iterated until all registration errors between the two objects (synthetic and real) are minimized. Assuming the tool or object is not defective, this optimized model pose represents an improved and more functionally relevant pose. In the event that a tool or object is bent, incorrectly assembled or otherwise defective, this process will fail to converge and trigger a safety warning. This process allows for confirmation that the 3D model 2420 is properly being projected onto the 2D images, an iterative method of adjusting the 3D model to a more accurate location on the 2D images, and provides an ability to detect tool or object deformities.

Figure 25:
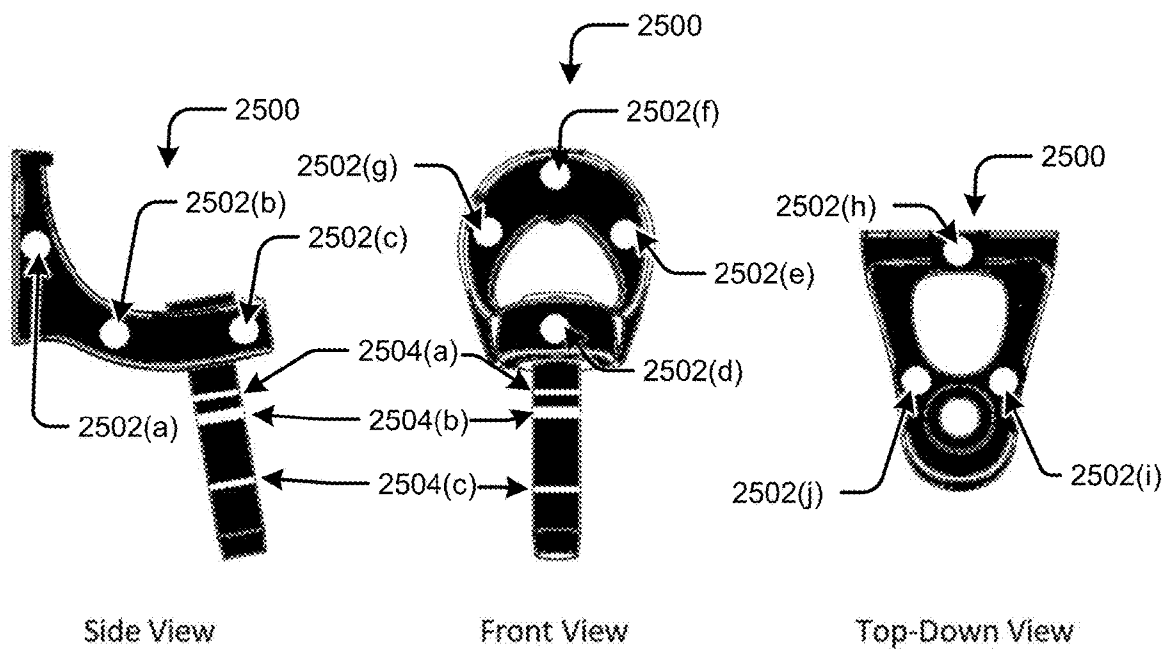
FIG. 25 illustrates an example of an end effector with fiducial disks, in accordance with some embodiments of the present disclosure.

FIG. 25 illustrates an example of an end effector 2500 with fiducial disks 2502*a-j*. The use of fiducial disks 2502*a-j* on the end effector may provide for reliable and robust identification and tracking from up to 80 degrees off-axis of any of the perspectives (side view, front view, and top-down view) shown in FIG. 25. Additionally, rings 2504*a-c* may be inserted, painted, or laser etched on the end effector's shaft for optional accuracy enhancement or directional verification of the end effector. The rings 2504*a-c* may be used to create a barcode or other machine readable optical code that provides identification information for the end effector 2500, or additionally or alternatively provide identification information for the shaft that the rings 2504*a-c* are located on. Additionally, the camera tracking system may generate tangential or perpendicular rays for the rings 2504*a-c* that may be used to determine a pose of the end effector. For example, by generating rays that are perpendicular to the rings 2504*a-c*, the computer tracking system may be able to determine information regarding the pose of the end effector such as the pose the end effector's shaft is pointing.

In one embodiment, the end effector 2500 is manufactured with metal that has gone through a black anodization process and has white fiducial disks thereon.

In another embodiment, the end effector 2500 is a white metal with black fiducial disks thereon; however, the camera tracking system has inverted the contrast such that the camera tracking system detects a black end effector with white fiducial disks thereon.

Figure 29:
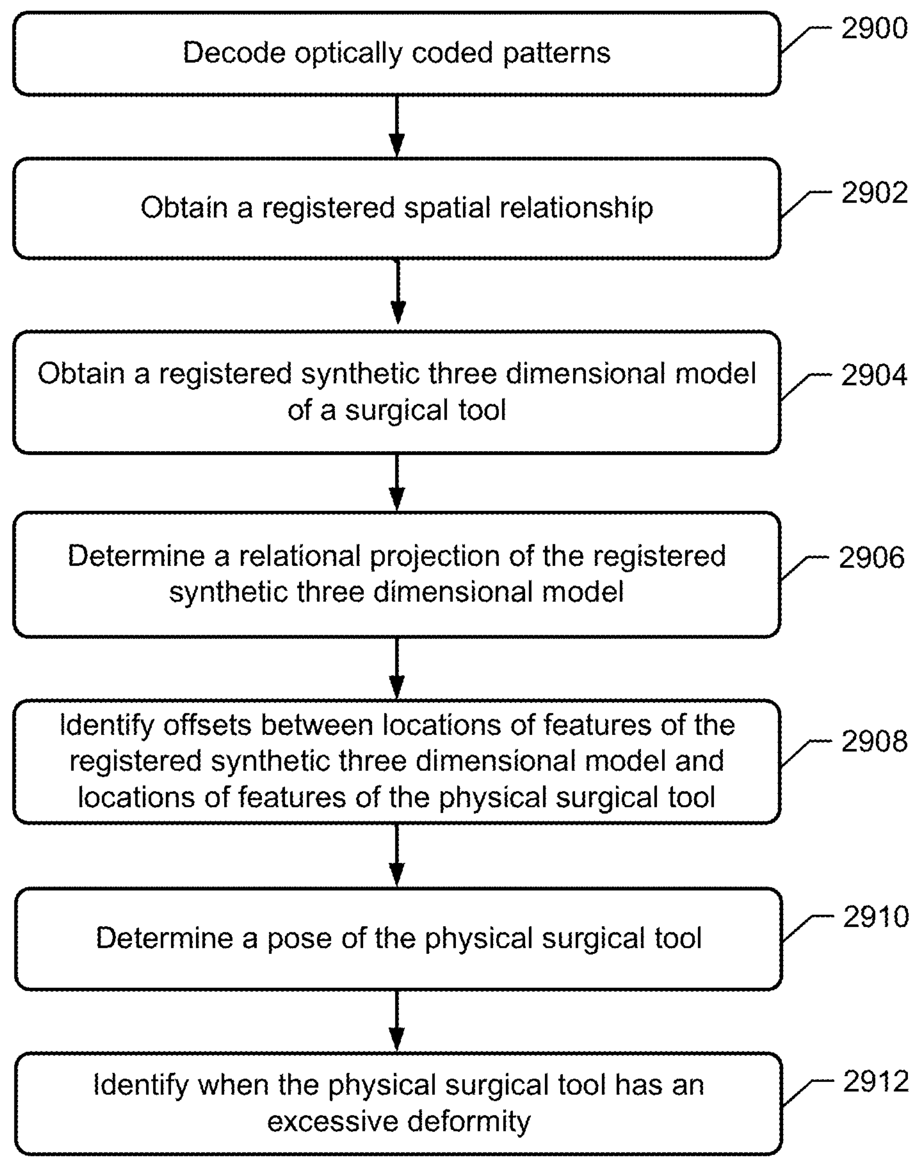
FIG. 29 illustrates another flowchart of operations performed by the camera tracking system, in accordance with some embodiments of the present disclosure.

FIG. 29 illustrates an example of processes performed by the camera tracking system, including the camera bar 1900 and tracking cameras (1910/1920/1930), in accordance with some embodiments. The camera tracking system, which includes camera bar 1900, may further include at least one processor operative to perform the processes of FIG. 29.

At block 2900, the at least one processor of the camera tracking system may be operative to decode optically coded patterns which are each on a different one of a plurality of different planar faces (e.g., 2310*a-e*) of a multi-faced reference array (e.g., 2310) attachable to a surgical tool (e.g., 2300) and imaged in video streams from the first, second, and third tracking cameras (e.g., 1910/1920/1930). Additionally, the at least one processor may determine one or more identifiers for corresponding one or more of the plurality of faces of the multi-faced reference array imaged in the video streams. The determining, of block 2900, may be based on decoding the optically coded patterns of the one or more of the plurality of faces of the multi-faced referenced array imaged in the video stream.

In an example where the optically coded patterns are two dimensional barcode patterns, the at least one processor may be further operative to decode the two dimensional barcode patterns.

At block 2902, the at least one processor may be further operative to obtain from a database a registered spatial relationship between corners and/or edges of the optically coded patterns of the one or more of the plurality of faces of the multi-faced reference array imaged in the video streams based on the one or more identifiers that are determined in block 2900. Additionally, the at least one processor may determine a pose of the multi-faced reference array based on the registered spatial relationship and triangulation of locations of the corners and/or edges of the optically coded patterns of the one or more of the plurality of faces of the multi-faced reference array imaged in the video streams to the locations of the first, second, and third tracking cameras spaced apart in the three dimensional space.

At block 2904, the at least one processor may be further operative to obtain from a database a registered synthetic three dimensional model of a surgical tool that has been registered as attached to the multi-faced reference array.

At block 2906, the at least one processor may be further operative to determine a relational projection of the registered synthetic three dimensional model onto a physical surgical tool imaged in a two dimensional plane of the frames in the video streams from the first, second, and third tracking cameras based on the determined pose of the multi-faced reference array, determined at block 2902.

At block 2908, the at least one processor may be further operative to identify offsets between locations of features of the registered synthetic three dimensional model and locations of features of the physical surgical tool imaged in a two dimensional plane of the frames in the video streams from the first, second, and third tracking cameras based on the determined relational projection of block 2906.

At block 2910, the at least one processor may be further operative to determine a pose of the physical surgical tool based on the identified offsets and the pose of the multi-faced reference array.

At block 2912, the at least one processor may be further operative to identify when the physical surgical tool has an excessive deformity based on the identified offsets satisfying a tool deformity rule. If an excessive deformity is identified, the at least one processor may trigger a safety warning.

Although various embodiments have been described in the context of using a set of tracking cameras on and XR headset, these and other embodiments can be used with any form of tracking cameras such as the set of tracking cameras on an auxiliary tracking bar and/or on another XR headset. Thus, in some embodiments, the set of tracking cameras are separate and spaced apart from the XR headset while the camera tracking system is receiving the tracking information from the set of tracking cameras. Various operations disclosed herein for pose chaining may be used to track poses of a reference array and/or a user's hand.

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, micro-code, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A camera tracking system for computer assisted navigation during surgery, comprising:

a camera bar;

first and second tracking cameras attached at spaced apart locations on the camera bar;

a third tracking camera attached at a location on the camera bar that is between locations of the first and second tracking cameras and spaced apart a distance from a line extending through centers of the first and second tracking cameras, at least one processor configured to execute saved instructions which cause the processor to determine a pose of physical objects in three dimensional space based on triangulating locations of the objects imaged in video streams from the first, second, and third tracking cameras to locations of the first, second, and third tracking cameras spaced apart in the three dimensional space wherein a set of physical objects are a physical reference array of spaced apart fiducials, wherein the at least one processor is further operative to:

determine a first pose of the physical reference array of spaced apart fiducials in the three dimensional space based on triangulating locations of the fiducials imaged in the video streams from the first and second tracking cameras to locations of the first and second tracking cameras spaced apart in the three dimensional space;

determine a second pose of the physical reference array of spaced apart fiducials in the three dimensional space based on triangulating locations of the fiducials imaged in the video streams from the first and third tracking cameras to locations of the first and third tracking cameras spaced apart in the three dimensional space; and determining a calibration accuracy of at least the first and second tracking cameras based on comparison of the first and second poses, wherein the calibration accuracy determines a precision of heading, yaw positioning, and/or spacing between tracking cameras in 3d space.

2. The camera tracking system of claim 1, wherein:

a first distance between the third tracking camera and the first tracking camera is equal to a second distance between the third tracking camera and the second tracking camera.

3. The camera tracking system of claim 1, wherein:

the distance the third tracking camera is spaced apart from the line is between one-quarter and one-half a distance measured between the centers of the first and second tracking cameras.

4. The camera tracking system of claim 1, wherein the physical reference array is spaced apart fiducial disks, wherein the at least one processor is further operative to:

detect potential disks in frames of the video streams from the video streams from the first, second, and third tracking cameras;

estimate centroid locations of the disks in the frames of the video streams;

verify whether the centroid locations of the disks form a pattern which corresponds to a pattern of disks of a registered reference array in a database;

responsive to successful verification of the disks, determine gradients along edges of the disks to generate gradient rays extending toward centroids of the disks;

adjust the gradient rays to reduce distortion based on defined intrinsic parameters of lenses of the first, second, and third tracking cameras, and output distortion compensated gradient rays;

perform a dual conic ellipse fitting on the distortion compensated gradient rays to determine distortion compensated centroid locations of the disks, wherein the compensated centroid location of each disk corresponds to where the distortion compensated gradient rays for the disk converge; and determine a pose of the physical reference array of spaced apart fiducials in the three dimensional space based on triangulating locations of the distortion compensated centroid locations of the disks in the video streams from the first, second, and third tracking cameras to locations of the first, second, and third tracking cameras spaced apart in the three dimensional space.

5. The camera tracking system of claim 1, further comprising:

at least one processor operative to decode optically coded patterns which are each on a different one of a plurality of different planar faces of a multi-faced reference array attachable to a surgical tool and imaged in video streams from the first, second, and third tracking cameras, and determine one or more identifiers for corresponding one or more of the plurality of faces of the multi-faced reference array imaged in the video streams based on decoding the optically coded patterns of the one or more of the plurality of faces of the multi-faced referenced array imaged in the video streams.

6. The camera tracking system of claim 5, wherein the at least one processor is further operative to:

obtain from a database a registered spatial relationship between corners and/or edges of the optically coded patterns of the one or more of the plurality of faces of the multi-faced reference array imaged in the video streams based on the one or more identifiers that are determined, and determine a pose of the multi-faced reference array based on the registered spatial relationship and triangulation of locations of the corners and/or edges of the optically coded patterns of the one or more of the plurality of faces of the multi-faced reference array imaged in the video streams to the locations of the first, second, and third tracking cameras spaced apart in the three dimensional space.

7. The camera tracking system of claim 5, wherein the optically coded patterns are two dimensional barcode patterns, and the at least one processor is further operative to decode the two dimensional barcode patterns.

8. The camera tracking system of claim 6, wherein the at least one processor is further operative to:

obtain from the database a registered synthetic three dimensional model of a surgical tool that has been registered as attached to the multi-faced reference array;

determining a relational projection of the registered synthetic three dimensional model onto a physical surgical tool imaged in a two dimensional plane of the frames in the video streams from the first, second, and third tracking cameras based on the determined pose of the multi-faced reference array;

identifying offsets between locations of features of the registered synthetic three dimensional model and locations of features of the physical surgical tool imaged in a two dimensional plane of the frames in the video streams from the first, second, and third tracking cameras based on the determining relational projection; and determine a pose of the physical surgical tool based on the identified offsets and the pose of the multi-faced reference array.

9. The camera tracking system of claim 8, wherein the at least one processor is further operative to:

identify when the physical surgical tool has an excessive deformity based on the identified offsets satisfying a tool deformity rule; and generating a safety notification to a user responsive to the tool deformity rule being satisfied.

10. The camera tracking system of claim 1, wherein the at least one processor is part of a navigation controller and is further operative to:

determine a pose of a surgical tool, which is attached to a set of physical objects, relative to a planned pose of the surgical tool when performing a surgical procedure on a patient;

generate steering information based on comparison of the determined pose of the surgical tool relative to the planned pose of the surgical tool, wherein the steering information indicates where the surgical tool needs to be moved and angularly oriented to become aligned with the planned pose when performing the surgical procedure; and provide the steering information to a display device.

11. A surgical system comprising:

a camera tracking system including a camera bar, first and second tracking cameras attached at spaced apart locations on the camera bar, a third tracking camera attached at a location on the camera bar that is between locations of the first and second tracking cameras and spaced apart a distance from a line extending through centers of the first and second tracking cameras, and at least one processor configured to execute saved instructions which cause the processor to be operative to determine a pose of a set of physical objects in three dimensional space based on triangulating locations of the objects imaged in video streams from the first, second, and third tracking cameras to locations of the first, second and third tracking cameras spaced apart in the three dimensional space, wherein the set of physical objects are a physical reference array of spaced apart fiducials, wherein the at least one processor is further operative to:

determine a first pose of the physical reference array of spaced apart fiducials in the three dimensional space based on triangulating locations of the fiducials imaged in the video streams from the first and second tracking cameras to locations of the first and second tracking cameras spaced apart in the three dimensional space;

determine a second pose of the physical reference array of spaced apart fiducials in the three dimensional space based on triangulating locations of the fiducials imaged in the video streams from the first and third tracking cameras to locations of the first and third tracking cameras spaced apart in the three dimensional space; and determine a calibration accuracy of at least the first and second tracking cameras based on comparison of the first and second poses;

wherein the calibration accuracy determines a precision of heading, yaw positioning, and/or spacing between tracking cameras in 3d space, a surgical robot including a robot base, a robot arm connected to the robot base, the robot arm configured to connect to an end effector which guides movement of a surgical tool, and at least one motor operatively connected to move the robot arm relative to the robot base; and at least one controller connected to the at least one motor and configured to determine a pose of the end effector relative to a planned pose of the end effector while guiding movement of the surgical tool to operate on a patient; and generate steering information based on comparison of the planned pose and the determined pose of the end effector, wherein the steering information indicates where the end effector needs to be moved to become aligned with the planned pose so the surgical tool will be guided by the end effector along a planned trajectory toward the patient.

* * * * *